US009828591B2

(12) United States Patent
Miasnikov et al.

(10) Patent No.: US 9,828,591 B2
(45) Date of Patent: Nov. 28, 2017

(54) THERMOSTABLE TRICHODERMA CELLULASE

(71) Applicant: Danisco US Inc., Palo Alto, CA (US)

(72) Inventors: Andrei Miasnikov, Union City, CA (US); Michael Schelle, San Francisco, CA (US); Michael Ward, San Francisco, CA (US)

(73) Assignee: DANISCO US INC CA (US)

( * ) Notice: Subject to any disclaimer, the term of this patent is extended or adjusted under 35 U.S.C. 154(b) by 0 days.

(21) Appl. No.: 14/831,763

(22) Filed: Aug. 20, 2015

(65) Prior Publication Data

US 2016/0040144 A1    Feb. 11, 2016

Related U.S. Application Data

(62) Division of application No. 13/276,467, filed on Oct. 19, 2011, now abandoned.

(60) Provisional application No. 61/394,946, filed on Oct. 20, 2010.

(30) Foreign Application Priority Data

Oct. 20, 2010   (EP) .................................... 10188285

(51) Int. Cl.
   *C12N 15/80*     (2006.01)
   *C12N 9/42*      (2006.01)
   *C07K 14/37*     (2006.01)
   *C12P 21/02*     (2006.01)

(52) U.S. Cl.
   CPC ............ *C12N 9/2437* (2013.01); *C07K 14/37* (2013.01); *C12N 15/80* (2013.01); *C12P 21/02* (2013.01); *C12Y 302/01004* (2013.01)

(58) Field of Classification Search
   None
   See application file for complete search history.

(56) References Cited

U.S. PATENT DOCUMENTS

| 5,650,322 A | 7/1997 | Clarkson et al. | |
|---|---|---|---|
| 2002/0165114 A1* | 11/2002 | Fowler ................. | C12N 9/2437 510/392 |
| 2007/0173431 A1* | 7/2007 | Day .................... | C11D 3/38645 510/320 |
| 2010/0151525 A1* | 6/2010 | Hedges ............... | C07K 14/375 435/71.1 |

FOREIGN PATENT DOCUMENTS

| WO | WO 94/26117 | 12/1994 |
|---|---|---|
| WO | WO 98/15619 | 4/1998 |
| WO | WO 02/12453 | 2/2002 |
| WO | WO 2005/001036 | 1/2005 |
| WO | WO 2005/093073 | 10/2005 |
| WO | WO 2008/118382 | 10/2008 |
| WO | WO 2008/148131 | 12/2008 |
| WO | WO 2009/076709 | * 6/2009 |
| WO | WO 2011/019686 | 2/2011 |

OTHER PUBLICATIONS

U.S. Appl. No. 61/469,067, filed Mar. 29, 2011, Heng, et al.
U.S. Appl. No. 61/475,933, filed Apr. 15, 2011, Michael W. Schelle.
Altschul, S.F., et al., "Basic Local Alignment Search Tool." *J. Mol. Biol.* 215: 403-410, 1990.
Altschul, S.F., et al., "Local Alignment Statistics." In *Methods in Enzymology*, vol. 266: pp. 460-480, 1993.
Aro, N., et al., "ACEII, a Novel Transcriptional Activator Involved in Regulation of Cellulase and Xylanase Genes of *Trichoderma reesei*." *J. Biol. Chem.* 276(26): 24309-24314, 2001.
Askolin, S. et al., "Overproduction, purification, and characterization of the *Trichoderma reesei* hydrophobin HFBI." *Applied Microbiology and Biotechnology* 57 (1-2): 124-130, 2001.
Devereux, J., et al., "A comprehensive set of sequence analysis programs for the VAX." *Nucleic Acids Res.* 12: 387-395, 1984.
Durand, P., et al., "Comparative study of cellulases and hemicellulases from four fungi: mesophiles *Trichoderma reesei* and *Penicillium* sp. and thermophiles *Thielvia terrestris* and *Sporotrichum cellulophilum*." *Enzyme and Microbial Technology* 6(4): 175-180, 1964.
Feng, D.-F., et al., "Progressive Sequence Alignment as a Prerequisite to Correct Phylogenetic Trees." *J. Mol. Evol.* 25: 351-360, 1987.
Freer, S.N., "Kinetic Characterization of a β-Glucosidase from a Yeast, *Candida wickerhamii*." *J. Biol. Chem.* 268(13): 9337-9342, 1993.
Henikoff, S., et al., "Amino acid substitution matrices from protein blocks." *Proc. Natl. Acad. Sci. USA* 89: 10915-10919, 1989.
Higgins, D.G., et al., "CLUSTAL: a package for performing multiple sequence alignment on a microcomputer." *Gene* 73: 237-244, 1988.
Higgins, D.G., et al., "Fast and sensitive multiple sequence alignments on a microcomputer." *CABIOS Communications* 5(2): 151-153, 1989.
Karlin, S., et al., "Applications and statistics for multiple high-scoring segments in molecular sequences." *Proc. Natl. Acad. Sci. USA* 90: 5873-5767, 1993.
Knowles, J., et al., "Cellulase families and their genes." *TIBTECH* 5: 255-261, 1987.
Linder, M.B., et al., "Hydrophobins: the protein-amphiphiles of filamentous fungi." *FEMS Microbiol Rev.* 29: 877-896, 2005.
Nakazawa, H., et al., "Directed evolution of endoglucanase III (Cel12A) from *Trichoderma reesei*." *Applied Microbiology and Biotechnology* 63(4): 649-657, 2009.
Needleman, S.B., et al., "A General Method Applicable to the Search for Similarities in the Amino Acid Sequence of Two Proteins." *J. Mol. Biol.* 48: 443-453, 1970.

(Continued)

*Primary Examiner* — Nancy Treptow

(57) ABSTRACT

Described are compositions and methods relating to the thermostable fungal cellulase enzyme, EGV, and *Trichoderma* host cells having a modification comprising or consisting essentially of disruption or deletion of nucleotide(s) for expression of this cellulose, whereby EGV expression is prevented.

13 Claims, 14 Drawing Sheets

(56) References Cited

OTHER PUBLICATIONS

Nevalainen, H, et al. "Molecular Biology of Cellulolytic Fungi." In *The Mycote, II Genetics and Biotechnology*. Kück, U., (ed.) pp. 303-319, Springer-Verlag, Berlin, Heidelberg, 1995.
Pearson, W.R., et al., "Improved tools for biological sequences comparison." *Proc. Natl. Acad. Sci. USA* 85: 2444-2448, 1988.
Saloheimo, A., et al., "A novel, small endoglucanase gene, egl5, from *Trichoderma reesei* isolated by expression in yeast." *Mol. Microbiol*. 13: 219-228, 1994.
Schulein, M., "Cellulases of *Trichoderma reesei*." In *Methods in Enzymology*. 160: 234-243, 1988.
International Search Report and the Written Opinion for PCT/US2011/56810 dated Feb. 16, 2012.

\* cited by examiner

```
AGCTTGGGGTGGTGGCCAATCAGCGGCCGCAGCGGGGGCGGGAGCTGGTGGCGGCGATATGAATTTCCGGGCGTTGC
TACAACAGGTACCACTTTGACCACCCATGGCTGCCGTCGCCCTGCTTGGAGCTTTCAGGTCGCTTCCGGGCGTTGGC
GAGGCAAGTTGGACGGTGGGGAAATGACGAAAAATGGTGCATCGCCTTTGTAGGTGTGTGTGAGTAGTAGTTCTACT
ATGAGGTACGTATGTAGCAGAAGGATCGAGCTAGAATCTGCCGGCATTGCAAAGGTTATCTGGAAAGAGGAAAAGGG
CCTGAACCGGCATATGGATGCATTCTTCGTACGAACTACTATCTGATAACAGTTAGGTACTGTTATCCATACAAAGA
GTCTTATAGAAACACTGCATCGTAATAAAATACTCGGTAGCTGCTTGAATATAGTAATAAGATCAACATCCTTTCAC
CTCTAGTCTCCGTGGATTCCAGTAAAAGCGCTCAATTCTGACTTCCGACTCTGTTGATGCCCCGTGTCTGCCCATCG
GGGTGGTCTAGACGCTGCCTCAACGCCCATGTACCGGCCTGATGGGGCCCTTGGGGGCACCACAAGTCCACTAAACG
AAGCACTGGGGACGGGACTCGATAGCCCTGAGCAGCAGCCGGTCTCAGCAGCCAACCAGCCCAGCTGGAAGCATCGG
CTAGGGGAGGGGGCCCAACTACTACGTGTACTACTAGGTACATAATGAATTGGATGGGACCCAGCCAGCCCAACCT
AACTTTCCAGCCTTTATAGCTGCAGCCTGCTTCCCCGTGCCTCACGCTTTTTGCTCCTCTGCTGGCCGGACTCGGAC
CTCTTGCGACCTCTGCTCGACCAACAATCCCTCTTGTTGCACCCTCTCGCTTTTGCTACCTCGACGCTCAATTCCTC
GCTGCCGCCTCACCTAACCGCGTGTGCTTGACTGCCCTCACGCTCGGCTCGCCTCCTGCTCCGCGAGCCTCCTTTTA
CACTTTTCAACAGCTACCCCGCCAGAATTCAAACATGTCGCCTTCCATGCAGACGCGGGCCTCCGTTGTCATCGACT
ACAATGTCGCACCTCCAAACCTATCCACTCTGCCCAATGGCTCCCTCTTCGAAACATGGCGTCCCCGCGCCCACGTC
CTGCCCCCCAACGGCCAGATCGGTGACCCCTGCCTGCATTACACCGATCCCTCCACGGGCCTCTTCCACGTCGGCTT
CCTTCACGATGGCAGCGGCATCTCCAGCGCCACCACTGATGATCTAGCCACCTACAAGGACCTCAACCAAGGCAACC
AAGTCATTGTTCCCGGGGGTATCAACGACCCCGTCGCCGTCTTCGATGGCTCCGTCATCCCCAGCGGCATCAACGGC
CTCCCCACTCTCCTCTACACCTCCGTCTCCTTCCTTCCCATCCACTGGTCCATCCCCTACACCCGGCAGTGAGAC
CCAATCCCTCGCTGTCTCCTCGGATGGCGGCAGCAACTTCACCAAGCTCGACCAGGGCCCCGTCATCCCTGGCCCTC
CCTTCGCCTACAACGTCACCGCATTCCGGGACCCCTACGTCTTCCAAAACCCCACCCTCGACTCCCTCCTGCACAGC
AAGAACAACACCTGGTATACCGTCATCTCCGGTGGTCTGCACGGCAAGGGCCCCGCCCAGTTCCTCTACCGCCAGTA
CGACCCGGACTTCCAGTACTGGGAGTTCCTCGGCCAATGGTGGCACGAGCCCACCAACTCCACTTGGGGTAACGGCA
CCTGGGCCGGCCGATGGGCCTTCAACTTCGAGACCGGCAACGTCTTCAGTCTCGACGAGTACGGATACAACCCCCAC
GGCCAGATCTTCTCCACGATCGGCACCGAGGGCTCTGACCAGCCCGTCGTGCCCCAGCTCACCAGCATCCACGACAT
GCTCTGGGTGTCCGGCAACGTCTCTCGCAATGGCTCTGTCTCGTTCACCCCGAACATGGCGGGCTTCCTCGACTGGG
GCTTCTCCTCTTACGCAGCTGCCGGAAAGGTCCTCCCCTCGACTTCTCTGCCCTCGACGAAGAGCGGCGCCCCGGAC
CGCTTCATCTCGTACGTCTGGCTGTCCGGTGACCTGTTCGAACAGGCCGAAGGGTTCCCCACGAACCAGCAGAATTG
GACCGGTACGCTGTTGCTTCCGCGAGAGTTGCGCGTGCTGTATATCCCCAATGTGGTGGACAATGCTCTGGCTCGGG
AATCTGGTGCCTCGTGGCAGGTCGTGAGCAGCGATAGCAGTGCGGGCACCGTGGAGCTGCAGACACTGGGTATCTCC
ATTGCCCGGGAAACCAAGGCCGCCTTGCTGTCGGGAACGTCGTTCACCGAGTCCGACCGTACTCTGAACAGCAGTGG
TGTTGTGCCGTTCAAGCGCTCCCCGTCCGAGAAGTTCTTTGTTTTGTCCGCGCAGCTGTCCTTCCCTGCTTCGGCTA
GGGGATCGGGACTCAAAAGTGGATTCCAGATCCTCTGCTCGGAGCTGGAAAGCACCACTGTCTACTACCAGTTCTCG
AATGAGTCGATTATTGTCGACCGCAGTAACACCAGTGCTGCGCGCGTACCACGGATGGTATCGATAGCAGTGCGGA
GGCTGGCAAGTTGCGCCTGTTTGACGTGTTGAATGGCGGAGAGCAGGCGATTGAGACGTTGGATTTGACTCTCGTGG
TGGATAACTCGGTATTGGAGATCTATGCCAATGGTCGGTTTGCGTTGAGTACTTGGGTTCGGTGAGTATCTTCCTAT
TTTATCAATGAAGTGTTTATGATGCTAACGTGGGGATAGTTCTTGGTACGCCAATTCCACGAACA.TCAGTTTCTTC
CAGAATGGCGTGGGTGGTGTTGCGTTCTCCAACGTGACCGTTTCCGAGGGCTTGTATGATGCTTGGCCGGATCGTCA
GTCTTAATCAGTCTTGAGGTGATGCCTAAGTAGTATCAAGGATCACTCCAGGTCAGGTCATACTGATCCGACAGTTA
ATGTCAGATGCATCGCGTTCAAGAAGAACGGCAGACATTAATCATGAGGTGCAGCAAAGAAGGGGCTCCCCGTTCTT
CGCAGCCCCTACCATGAACGCCGATGAGGCCGGGTCTATTGACAATATTATTTTCCTTCTTAACAACTGTTTTATTA
TATCACAAGAATCAAAGAAATCCAAGCCAGACTGCAATTCCGTCAACAATAACGCCATCGCTATGTAAATTGCCCCA
GTTGTTTTCCCTTCCCGATACTTTACTGAACTGATACACGATGAAGACTTGTACTCGACGTTCGCGGTGAAATATGA
CTCGGTCGGAGAGGAGCTACTCCCAGCTCGTCAATCTGCGGAACAGGCTTCCTTTGCCCGACAAGTTGCGCGGACCC
GTTCCCTGACTCTGAGGGTGCGGAATATGAATGTGCACGTGGTGCCTGTGGACCGGGGTACGCTACGATACTCCCCC
TCGCTGGCTGATCAGACACTGTCGAGTATGTGCTTAGTGGTTGATACTGAGCCGGCGGGGTCAATGTCGTAGCAGGT
GAAGTTTCGG
```

*FIG. 7*

```
CTAGAGGCCTAAATGGCCATGAGACAATAACCCTGATAAATGCTTCAATAATATTGAAAAAGGA
AGAGTATGAGTATTCAACATTTCCGTGTCGCCCTTATTCCCTTTTTTGCGGCATTTTGCCTTCC
TGTTTTTGCTCACCCAGAAACGCTGGTGAAAGTAAAAGATGCTGAAGATCAGTTGGGTGCACGA
GTGGGTTACATCGAACTGGATCTCAACAGCGGTAAGATCCTTGAGAGTTTTCGCCCCGAAGAAC
GTTTTCCAATGATGAGCACTTTTAAAGTTCTGCTATGTGGCGCGGTATTATCCCGTATTGACGC
CGGGCAAGAGCAACTCGGTCGCCGCATACACTATTCTCAGAATGACTTGGTTGAGTACTCACCA
GTCACAGAAAAGCATCTTACGGATGGCATGACAGTAAGAGAATTATGCAGTGCTGCCATAACCA
TGAGTGATAACACTGCGGCCAACTTACTTCTGACAACGATCGGAGGACCGAAGGAGCTAACCGC
TTTTTTGCACAACATGGGGGATCATGTAACTCGCCTTGATCGTTGGGAACCGGAGCTGAATGAA
GCCATACCAAACGACGAGCGTGACACCACGATGCCTGTAGCAATGGCAACAACGTTGCGCAAAC
TATTAACTGGCGAACTACTTACTCTAGCTTCCCGGCAACAATTAATAGACTGGATGGAGGCGGA
TAAAGTTGCAGGACCACTTCTGCGCTCGGCCCTTCCGGCTGGCTGGTTTATTGCTGATAAATCT
GGAGCCGGTGAGCGTGGGTCTCGCGGTATCATTGCAGCACTGGGGCCAGATGGTAAGCCCTCCC
GTATCGTAGTTATCTACACGACGGGGAGTCAGGCAACTATGGATGAACGAAATAGACAGATCGC
TGAGATAGGTGCCTCACTGATTAAGCATTGGTAACTGTCAGACCAAGTTTACTCATATATACTT
TAGATTGATTTAAAACTTCATTTTTAATTTAAAAGGATCTAGGTGAAGATCCTTTTTGATAATC
TCATGACCAAAATCCCTTAACGTGAGTTTTCGTTCCACTGAGCGTCAGACCCCGTAGAAAAGAT
CAAAGGATCTTCTTGAGATCCTTTTTTTCTGCGCGTAATCTGCTGCTTGCAAACAAAAAAACCA
CCGCTACCAGCGGTGGTTTGTTTGCCGGATCAAGAGCTACCAACTCTTTTTCCGAAGGTAACTG
GCTTCAGCAGAGCGCAGATACCAAATACTGTCCTTCTAGTGTAGCCGTAGTTAGGCCACCACTT
CAAGAACTCTGTAGCACCGCCTACATACCTCGCTCTGCTAATCCTGTTACCAGTGGCTGCTGCC
AGTGGCGATAAGTCGTGTCTTACCGGGTTGGACTCAAGACGATAGTTACCGGATAAGGCGCAGC
GGTCGGGCTGAACGGGGGGTTCGTGCACACAGCCCAGCTTGGAGCGAACGACCTACACCGAACT
GAGATACCTACAGCGTGAGCTATGAGAAAGCGCCACGCTTCCCGAAGGGAGAAAGGCGGACAGG
TATCCGGTAAGCGGCAGGGTCGGAACAGGAGAGCGCACGAGGGAGCTTCCAGGGGGAAACGCCT
GGTATCTTTATAGTCCTGTCGGGTTTCGCCACCTCTGACTTGAGCGTCGATTTTTGTGATGCTC
GTCAGGGGGCGGAGCCTATGGAAAAACGCCAGCAACGCTGCAGCATTTCCCCGAAAAGTGCCA
CCTGACGCGCCCTGTAGCGGCGCATTAAGCGCGGCGGGTGTGGTGGTTACGCGCAGCGTGACCG
CTACACTTGCCAGCGCCCTAGCGCCCGCTCCTTTCGCTTTCTTCCCTTCCTTTCTCGCCACGTT
CGCCGGCTTTCCCCGTCAAGCTCTAAATCGGGGGCTCCCTTTAGGGTTCCGATTTAGTGCTTTA
CGGCACCTCGACCCCAAAAAACTTGATTAGGGTGATGGTTCACGTAGTGGGCCATCGCCCTGAT
AGACGGTTTTTCGCCCTTTGACGTTGGAGTCCACGTTCTTTAATAGTGGACTCTTGTTCCAAAC
TGGAACAACACTCAACCCTATCTCGGTCTATTCTTTTGATTTATAAGGGATTTTGCCGATTTCG
GCCTATTGGTTAAAAAATGAGCTGATTTAACAAAAATTTAACGCGAATTTTAACAAAATATTAA
CGCTTACAATTTACGCGTTAAGATACATTGATGAGTTTGCGGCCGCT
```

*FIG. 8*

```
GCATTTCCCCGAAAAGTGCCACCTGACGCGCCCTGTAGCGGCGCATTAAGCGCGGCGGGTGTGGTGGTTACGCGCAG
CGTGACCGCTACACTTGCCAGCGCCCTAGCGCCCGCTCCTTTCGCTTTCTTCCCTTCCTTTCTCGCCACGTTCGCCG
GCTTTCCCCGTCAAGCTCTAAATCGGGGGCTCCCTTTAGGGTTCCGATTTAGTGCTTTACGGCACCTCGACCCCAAA
AAACTTGATTAGGGTGATGGTTCACGTAGTGGGCCATCGCCCTGATAGACGGTTTTTCGCCCTTTGACGTTGGAGTC
CACGTTCTTTAATAGTGGACTCTTGTTCCAAACTGGAACAACACTCAACCCTATCTCGGTCTATTCTTTTGATTTAT
AAGGGATTTTGCCGATTTCGGCCTATTGGTTAAAAAATGAGCTGATTTAACAAAAATTTAACGCGAATTTTAACAAA
ATATTAACGCTTACAATTTACGCGTTAAGATACATTGATGAGTTTGCGGCCGCAATTCAGATATTCCAAATCATCTT
GCACGACGTCTGAACGAATTAATGAAGCAAAATAGAGTATTTTCACAGGTAAAGTGAGGTCAGCAGGTAATGTGTAG
ATACGCTTCTCGGAACTTGAAGAGCCCAAGCCAAATTGAAAGTCGAATCAGCCCGCTCCTCTTTGCCGCAGCCAATA
GAGACGTGCAGCCTCCATGCATGTAAAGCGGGCGAATGTCACCCAACCAACCAACCGCATCAAGCCACCAAATCCGA
GCATTGCCGGCCGAAATTCGACTCAAGTCTCACTGACCATAAAAACCCCCAACATCCCTCTTCTCGACAAAGAGATT
CAAACAGCAAAAAAAAATGCAAAAAAACATACAACAGCCGGTGTTCGCCAGTGGTCACCCACCTGACTACTAATCTG
CCGGTTAGTGGCTTGTCTATGGGGGAGCAGACGGGACCCCGAATTCTCCACTACCTATGGTCGTATGTGCTTGGATC
TCTGTGGAATGGCTTCATATTGATGGCAGGACGCATATCTTGATCAGTGCTTGTGTTCGGCCGATGGCGGCCATGCG
TTGCTAGAGCATGCTGTTCTCAGGCCTCTGCTCCTTGTCATTACCTGTAAGGTATAGAAGCTGATAGGTCCCACCTC
TGCGGACTACACATGGCCTTGAATCCTATGGATAGGGGTGCAACGACACTCTACAAGTCAGAAGAGTAATAGCGAG
ATTGGAGGCGAGCGCCCTGCAACACTCTTCTCGAATCCTATCGGGATATCATATACCAATTAGCCTGTTCCAAGGTA
GTATACGTTCACGGAAAGAGCTTTAGCAATTACAGGTGCAAACATCAGCCTGTCTGGTAGGTAATTAGCCTGTTGCT
GTAAACCTGAAGCGTTGACCCTGGCAATAGCCTGTTGCTATAAACCTGAGGCGTTGACCCTGGCAATAGCCTGTTGT
TCATTTGCCCCTGGCGTTGCAAGCCGCGTACAACTGCCCTTTTACCTAGTCTCGAGTTTATAAGTGACAACATGCTC
TCAAAGCGCTCATGGCTGGCACAAGCCTGGAAAGAACCAACACAAAGCATACTGCAGCAAATCAGCTGAATTCGTCA
CCAATTAAGTGAACATCAACCTGAAGGCAGAGTATGAGGCCGAAGCACATCTGGATCGCAGATCATGGATTGCCCC
TCTTGTTGAAGATGAGAATCTAGAAAGATGGCGGGGTATGAGATAAGAGCGATGGGGGGGCACATCATCTTCCAAGA
CAAACAACCTTTGCAGAGTCAGGCAATTTTTCGTATAAGAGCAGGAGGAGGGAGTCCAGTCATTTCATCAGCGGTAA
AATCACTCTAGACAATCTTCAAGATGAGTTCTGCCTTGGGTGACTTATAGCCATCATCATACCTAGACAGAAGCTTG
TGGGATACTAAGACCAACGTACAAGCTCGCACTGTACGCTTTGACTTCCATGTGAAAACTCGATACGGCGCGCCTCT
AAATTTTATAGCTCAACCACTCCAATCCAACCTCTGCATCCCTCTCACTCGTCCTGATCTACTGTTCAAATCAGAGA
ATAAGGACACTATCCAAATCCAACAGAATGGCTACCACCTCCCAGCTGCCTGCCTACAAGCAGGACTTCCTCAAATC
CGCCATCGACGGCGGCGTCCTCAAGTTTGGCAGCTTCGAGCTCAAGTCCAAGCGGATATCCCCCTACTTCTTCAACG
CGGGCGAATTCCACACGGCGCGCCTCGCCGGCGCCATCGCCTCCGCCTTTGCAAAGACCATCATCGAGGCCCAGGAG
AAGGCCGGCCTAGAGTTCGACATCGTCTTCGGCCCGGCCTACAAGGGCATCCCGCTGTGCTCCGCCATCACCATCAA
GCTCGGCGAGCTGGCGCCCCAGAACCTGGACCGCGTCTCCTACTCGTTTGACCGCAAGGAGGCCAAGGACCACGGCG
AGGGCGGCAACATCGTCGGCGCTTCGCTCAAGGGCAAGAGGGTCCTGATTGTCGACGACGTCATCACCGCCGGCACC
GCCAAGAGGGACGCCATTGAGAAGATCACCAAGGAGGGCGGCATCGTCGCCGGCATCGTCGTGGCCCTGGACCGCAT
GGAGAAGCTCCCCGCTGCGGATGGCGACGACTCCAAGCCTGGACCGAGTGCCATTGGCGAGCTGAGGAAGGAGTACG
GCATCCCCATCTTTGCCATCCTCACTCTGGATGACATTATCGATGGCATGAAGGGCTTTGCTACCCCTGAGGATATC
AAGAACACGGAGGATTACCGTGCCAAGTACAAGGCGACTGACTGATTGAGGCGTTCAATGTCAGAAGGGAGAGAAAG
ACTGAAAAGGTGGAAAGAAGAGGCAAATTGTTGTTATTATTATTATTCTATCTCGAATCTTCTAGATCTTGTCGTAA
ATAAACAAGCGTAACTAGCTAGCCTCCGTACAACTGCTTGAATTTGATACCCGTATGGAGGGCAGTTATTTTATTTT
GTTTTTCAAGATTTTCCATTCGCCGTTGAACTCGTCTCACATCGCGTGTATTGCCCGGTTGCCCATGTGTTCTCCTA
CTACCCCAAGTCCCTCACGGGTTGTCTCACTTTCTTTCTCCTTTATCCTCCCTATTTTTTTTCAAGTCAGCGACAGA
GCAGTCATATGGGGATACGTGCAACTGGGACTCACAACAGGCCATCTTATGGCCTAATAGCCGGCGTTGGATCCACT
AGAGCCGACGAGTATCGTGGGGCAATTGCTTTTCTTCTGGGGGACGCGAGTTCGTATGTCACTGGGACGGATCTGCG
GATTGACGGAGGATCGACGGGGTGGTGAGAACGTATTCGAAGATGGCTTCACACTCAATTATCACATCGTGTATCGA
TTTTGTGCATAGTTTTGAAGTAGGTAGCTAATGAAAGAGCTTGACATGTGATATCTGAGTCGTCCCTCACCGAGGTT
CACTCTCACGGTCTTCGTCAACAGACTCTCTCACGCCCCGAATCACCGGCTGCCTCTTCCAATGCAACACCTATCAA
GAAACAATCAGCAAAGAAGAATAAAGAAGAAACAGGCGCATCATATCAAGAAACAGAATGATACTCACCCGTAAA
```

*FIG. 9A*

```
TAGACTCCCACATACAGCACCAAAAGTACCGCATACCCAATCCTCCTGAGGAAAAACATCCCTGATCCCGAGAACAC
GCACAAGAAGACCCACGTCAGAGAAGACAAAGCGAAGATATCCGGCGCCTTAATGAATTCAGATATTCCAAATCATC
TTGCACGACGTCGAGCTCCGGCGCATTCCCGTGGCAGGTAAACATTCGACCTTGTCTGGGGCAAGGGACTCGTCACT
TACATCCTCTCTCTCTCTGCAGCTCGGCATCGGCAACGGAGTCTACACGGCTGCCGGCTCCCAGGCTCTCTTCGACA
CGGCCGGAGCTTCATGGTGCGGCGCCGGCTGCGGTAAATGCTACCAGCTCACCTCGACGGGCCAGGCGCCCTGCTCC
AGCTGCGGCACGGGCGGTGCTGCTGGCCAGAGCATCATCGTCATGGTGACCAACCTGTGCCCGAACAATGGGAACGC
GCAGTGGTGCCCGGTGGTCGGCGGCACCAACCAATACGGCTACAGCTACCATTTCGACATCATGGCGCAGAACGAGA
TCTTTGGAGACAATGTCGTCGTCGACTTTGAGCCCATTGCTTGCCCCGGGCAGGCTGCCTCTGACTGGGGGACGTGC
CTCTGCGTGGGACAGCAAGAGACGGATCCCACGCCCGTCCTCGGCAACGACACGGGCTCAACTCCTCCCGGGAGCTC
GCCGCCAGCGACATCGTCGAGTCCGCCGTCTGGCGGCGGCCAGCAGACGCTCTATGGCCAGTGTGGAGGTGCCGGCT
GGACGGGACCTACGACGTGCCAGGCCCCAGGGACCTGCAAGGTTCAGAACCAGTGGTACTCCCAGTGTCTTCCTTGA
GAAGGCCCAAGATAGCCATGTCTCTCTAGCATTCTTCCGGCGTCAGTCTGATCTGCCTATTTAATCAGGTCAGTCAA
TATGTATCCAGAGATAATAAATTATGTATATTATAGCAGTACTGTATCATTGCTGCTGTCTGCCTGACTTCAATGCT
GCTTCCCCTATTCTCGTTGCAGTAGCGTTGGCGATATGGGGCAGTTGAATAGTAAGCGGAAGCGAACATCAGGAGAT
CTCATCTATAACCGACTGTCGCCTAATGAGCGCCAAGCAATTCCGCCGGCACTTGCATTTGGCCGATGTATTATGCC
GTACGATCCCATGGCCTAAATGGCCATGAGACAATAACCCTGATAAATGCTTCAATAATATTGAAAAAGGAAGAGTA
TGAGTATTCAACATTTCCGTGTCGCCCTTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGGTTACATCGAACTGGATCTCAACAGCGG
TAAGATCCTTGAGAGTTTTCGCCCCGAAGAACGTTTTCCAATGATGAGCACTTTTAAAGTTCTGCTATGTGGCGCGG
TATTATCCCGTATTGACGCCGGGCAAGAGCAACTCGGTCGCCGCATACACTATTCTCAGAATGACTTGGTTGAGTAC
TCACCAGTCACAGAAAAGCATCTTACGGATGGCATGACAGTAAGAGAATTATGCAGTGCTGCCATAACCATGAGTGA
TAACACTGCGGCCAACTTACTTCTGACAACGATCGGAGGACCGAAGGAGCTAACCGCTTTTTTGCACAACATGGGGG
ATCATGTAACTCGCCTTGATCGTTGGGAACCGGAGCTGAATGAAGCCATACCAAACGACGAGCGTGACACCACGATG
CCTGTAGCAATGGCAACAACGTTGCGCAAACTATTAACTGGCGAACTACTTACTCTAGCTTCCCGGCAACAATTAAT
AGACTGGATGGAGGCGGATAAAGTTGCAGGACCACTTCTGCGCTCGGCCCTTCCGGCTGGCTGGTTTATTGCTGATA
AATCTGGAGCCGGTGAGCGTGGGTCTCGCGGTATCATTGCAGCACTGGGGCCAGATGGTAAGCCCTCCCGTATCGTA
GTTATCTACACGACGGGGAGTCAGGCAACTATGGATGAACGAAATAGACAGATCGCTGAGATAGGTGCCTCACTGAT
TAAGCATTGGTAACTGTCAGACCAAGTTTACTCATATATACTTTAGATTGATTTAAAACTTCATTTTTAATTTAAAA
GGATCTAGGTGAAGATCCTTTTTGATAATCTCATGACCAAAATCCCTTAACGTGAGTTTTCGTTCCACTGAGCGTCA
GACCCCGTAGAAAAGATCAAAGGATCTTCTTGAGATCCTTTTTTTCTGCGCGTAATCTGCTGCTTGCAAACAAAAAA
ACCACCGCTACCAGCGGTGGTTTGTTTGCCGGATCAAGAGCTACCAACTCTTTTTCCGAAGGTAACTGGCTTCAGCA
GAGCGCAGATACCAAATACTGTCCTTCTAGTGTAGCCGTAGTTAGGCCACCACTTCAAGAACTCTGTAGCACCGCCT
ACATACCTCGCTCTGCTAATCCTGTTACCAGTGGCTGCTGCCAGTGGCGATAAGTCGTGTCTTACCGGGTTGGACTC
AAGACGATAGTTACCGGATAAGGCGCAGCGGTCGGGCTGAACGGGGGGTTCGTGCACACAGCCCAGCTTGGAGCGAA
CGACCTACACCGAACTGAGATACCTACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTCCAGGGGGAAACGCCTGGTATCTTTA
TAGTCCTGTCGGGTTTCGCCACCTCTGACTTGAGCGTCGATTTTTGTGATGCTCGTCAGGGGGGCGGAGCCTATG
GAAAAACGCCAGCAACGCTGCA
```

*FIG. 9B*

```
1     cgtatcttac acaagggcgc tgcaactaat tgacttgatc ttccatctcg tgtcttgctt
61    gtaaccatcg tgaccatgaa ggcaactctg gttctcggct ccctcattgt aggcgccgtt
121   tccgcgtaca aggccaccac cacggcaagt ctacatgctt ccaggtcaca acgtctgctc
181   aacaacctct aaccgaaagg ccagcgctac tacgatgggc aggagggtgc ttgcggatgc
241   ggctcgagct ccggcgcatt cccgtggcag gtaaacattc gaccttgtct ggggcaaggg
301   actcgtcact tacatcctct ctctctctgc agctcggcat cggcaacgga gtctacacgg
361   ctgccggctc ccaggctctc ttcgacacgg ccggagcttc atggtgcggc gccggctgcg
421   gtaaatgcta ccagctcacc tcgacgggcc aggcgccctg ctccagctgc ggcacgggcg
481   gtgctgctgg ccagagcatc atcgtcatgg tgaccaacct gtgcccgaac aatgggaacg
541   cgcagtggtg cccggtggtc ggcggcacca accaatacgg ctacagctac catttcgaca
601   tcatggcgca gaacgagatc tttggagaca atgtcgtcgt cgactttgag cccattgctt
661   gccccgggca ggctgcctct gactggggga cgtgcctctg cgtgggacag caagagacgg
721   atcccacgcc cgtcctcggc aacgacacgg gctcaactcc tccgggagc tcgccgccag
781   cgacatcgtc gagtccgccg tctggcggcg gccagcagac gctctatggc cagtgtggag
841   gtgccggctg gacgggacct acgacgtgcc aggcccagg gacctgcaag gttcagaacc
901   agtggtactc ccagtgtctt ccttgagaag gccaagata gccatgtctc tctagcattc
961   ttccggcgtc agtctgatct gcctatttaa tcaggtcagt caatatgtat ccagagataa
1021  taaattatgt atattatagc agtactgtat cattgctgct gtctgcctga cttcaatgct
1081  gcttccccta ttctcgttgc agtagcgttg gcgatatggg gcag
```

*FIG. 10*

MKATLVLGSLIVGAVSAYKATTTRYYDGQEGACGCGSSSGAFPWQLGIGNGVYTAAG
SQALFDTAGASWCGAGCGKCYQLTSTGQAPCSSCGTGGAAGQSIIVMVTNLCPNNGNA
QWCPVVGGTNQYGYSYHFDIMAQNEIFGDNVVVDFEPIACPGQAASDWGTCLCVGQQ
ETDPTPVLGNDTGSTPPGSSPPATSSSPPSGGGQQTLYGQCGGAGWTGPTTCQAPGTCK
VQNQWYSQCLP

*FIG. 11*

```
   1 CTAGAGGCCA TTTAGGCCGT TGCTGGCGTT TTTCCATAGG CTCCGCCCCC CTGACGAGCA TCACAAAAAT CGACGCTCAA GTCAGAGGTG GCGAAACCCG
 101 ACAGGACTAT AAAGATACCA GGCGTTTCCC CCTGGAAGCT CCCTCGTGCG CTCTCCTGTT CCGACCCTGC CGCTTACCGG ATACCGTCC GCCTTTCTCC
 201 CTTCGGGAAG CGTGGCGCTT TCTCATAGCT CACGCTGTAG GTATCTCAGT TCGGTGTAGG TCGTTCGCTC CAAGCTGGGC TGTGTGCACG AACCCCCGT
 301 TCAGCCCGAC CGCTGCGCCT TATCCGTCTT GAGTCCAACC CGGTAAGACA CGACTTATCG CCACTGGCAG CAGCCACTGG TAACAGGATT
 401 AGCAGAGCGA GGTATGTAGG CGGTGCTACA GAGTTCTTGA AGTGGTGGCC TAACTACGGC TACACTAGAA GGACAGTATT TGGTATCTGC GCTCTGCTGA
 501 AGCCAGTTAC CTTCGGAAAA AGAGTTGGTA GCTCTTGATC CGGCAAACAA ACCACCGCTG GTAGCGGTGG TTTTTTTGTT TGCAAGCAGC AGATTACGCG
 601 CAGAAAAAAG GGATCTCAAG AAGATCCTTT GATCTTTTCT ACGGGGTCTG ACGCTCAGTG GAACGAAAAC TCACGTTAAG GGATTTTGG CCGATTTTGG
 701 TCATGAGATT TTAATCAGTG TTAATTGTAA TGACCACTAT CTCAGCGATC ATGATACCCG GATCCGTAT GTCCACGATA AGCATCCA GGTCTGACAG
 801 TTACCAATGC TTAATCAGTG AGGCACCTAT CTCAGCGATC ATGATACCCG AGATACCGGG AAATTAAAAA TGAAGTTTTA AATCAATCTA AAGTATATAT GAGTAAACTT TACGATACGG
 901 GAGGGCTTAC CATCTGGCCC CAGTGCTGCA ACTTTATCCG CCTCCATCCA GTCTATTAAT TGTTGCCGGG AAGCTAGAGT CTCACCCGCT CCAGATTTAT AGTTGCTCA CCAGCCAGCC GGAAGGGCCG
1001 AGCGCAGAAG TGGTCCTGCA ACTTTATCCG CCTCCATCCA GTCTATTAAT TGTTGCCGGG AAGCTAGAGT AAGTAGTTCG CCAGTAATAA CCAGCCAGCC GTTTGCGCAA
1101 CGTTGTTGCC ATTGCTACAG GCATCGTGGT GTCACGCTCG TCGTTTGGTA TGGCTTCATT CAGCTCCGGT TCCCAACGAT CAAGGCGAGT TACATGATCC
1201 CCCATGTTGT GCAAAAAAGC GGTTAGCTCC TTCGGTCCTC CGATCGTTGT CAGAAGTAAG TTGGCCGCAG TGTTATCACT CATGGTATG GCAGCACTGC
1301 ATAATTCTCT TACTGTCATG GATGCTTTTC TGTGACTGGT GAGTACTCAA CCAAGTCATT CTGAGAATAG AAACGTTCTT CGGGCGAAA GACCGAGTTG
1401 CTCTTGCCCG GCGTCAATAC GGGATAATAC CGCGCCACAT AGCAGAACTT TAAAAGTGCT CATCATTGGA CTTTCACCAG CGTTCTGGG ACTCTCAAGG
1501 ATCTTACCGC TGTTGAGATC CAGTTCGATG TAACCCACTC GTGCACCCAA CTGATCTTCA GCATCTTTTA CTTTCACCAG CGTTTCTGGG TGAGCAAAAA
1601 CAGGAAGGCA AAATGCCGCA AAAAAGGGAA TAAGGGCGAC ACGGAAATGT TGAATACTCA TACTCTTCCT TTTTCAATAT TATTGAAGCA TTTATCAGGG
1701 TTATTGTCTC ATGAGCGGAT ACATATTTGA ATGTATTTAG AAAAATAAAC AAATAGGGGT TCCGCGCACA TTTCCCCGAA AAGTGCCACC TGACGTCTAA
1801 GAAACCATTA TTATCATGAC ATTAACCTAT AAAAATAGGC GTATCACGAG GCCCTTTCGT CTTCAAGAA
```

FIG. 13A

```
3301 CTGGCTGCTG TCTGCCCTAC CGGCCTCTCT TCCAACCCTC TGTGCTGTGC CACCAACGTC CTCGACCTCA TTGGCGTTGA CTGCAAGACC CGTATGTTGA
3401 ATTCCAATCT CTGGGCATCC TGACATTGGA CGATACAGTT GCTGCGTTGC GACTTACACG ATGCTTTACA GCTACCATCG CCGTCGACAC TGGCGGCATC TTCCAGGCTC
3501 ACTGTGCCAG CAAGGGCTCC AAGCCTCTTT GCTGCGTTGC TCTCCGTTGC TCCCGTTGTA AGTAGTGCTC GCAATGGCAA AGAAGTAAAA AGACATTTGG GCCTGGGATC
3601 GCTAACTCTT GATATCAAGG CCGACCAGGC CCCAGCTTTC TTGTACAAAG CAGAAGGCCA TCGGCACCTT GCCAGCTCCG TGCCAAAGCC GCCTTGCTTT ACTGCCGGCA GTCTTTGAGA
3701 ACTAAGGGTG GGCGCGGCGA CCCAGCTTTC CTACATGGCC CGGGTGATT TATTTTTTT GTATCTACTT CTGACCCTTT TCAAATATAC GCCTTGCTTT ACTGCCGGCA GGTGAGCCCG
3801 TATCATGACG GCGGCGGCAG CTACATGGCC CGGGTGATT TATTTTTTT GTATCTACTT CTGACCCTTT TCAAATATAC GGTCAACTCA TGAGATTCTT TCTTTCACTG
3901 GAGATGCCGC CTGCTTGGTA TTGCGATGTT GTCAGCTTGG CAAATTGTGG CTTTCGAAAA CACAAAACGA TTCCTTAGTA GCCATGCATT TTAAGATAAC
4001 GGAATAGAAG AAAGAGGAAA TTAAAAAAAA AAAAAAAACA AACATCCCGT TCATAACCCG TAGAATCGCC GTCTTTCGTG TATCCAGTA CCAGTTTATT
4101 TTGAATAGCT CGCCCGTTGG AGAGCATCCT GAATGCAAGT GAGGCTGACA CGGCAGGTGT TGCTAGGGAG CGTCGTGTTC TACAAGGCCA
4201 GACGTCTTCG CGGTGATAT ATATGTATGT TTGACTGCAG GCTGCTCAGC GACGACAGTC AAGTTCGCCC TCGCTGCTTG TGCAATAATC GCAGTGGGGA
4301 AGCCACACCG TGACTCCCAT CTTTCAGTAA AGCTCTGTTG GTGTTTATCA GCAATACACG TAATTTAAAC TCGTTAGCAT GGGGCTGATA GCTTAATTAC
4401 CGTTTACCAG TGCCATGGTT CTGCAGCTTT CCTTGGCCCG TAAAATTCGG CGAAGCCAGC CAATCACCAG CTAGGCACCA GCTAAACCCT ATAATTAGTC
4501 TCTTATCAAC ACCATCCGCT CCCCCGGGAT CAATGAGGAG AATGAGGGGC AAAGAAGCCT ACATAACCCT CATGCCAACT CCCAGTTTAC
4601 ACTCCTCGAG CCAAACATCCT GACTATAAGC TAACACAGAA TGCCTCAATC CTGGGAAGAA CTGGCCGCTG ATAAGCGCGC CCGCCTCGCA AAAACCATCC
4701 CTGATGAATG GAAAGTCCAG ACGCTGCCTG CGGAAGACAG CGTTATTGAT TTCCCAAAGA AATCGGGGAT CCTTTCAGAG GCCGAACTGA AGATCACAGA
4801 GGCCTCCGCT GCAGATCTTG TGTCCAAGCT GGCGGCCGGA GAGTTGACCT CGGTGGAAGT TTCTGTAAAC TACGCTAGCA GGGCAGCAAT CGCCCAGCAG
4901 TTAGTAGGGT CCCCTCTTAC TCTCAGGGAG ATGTAACAAC GCCACCTTAT GGGACTATCA AGCTGACGCT GGCTTCGTG CAGACAAACT GCGCCACGA
5001 GTTCTTCCCT GACGCCGCTC TCCGCCAGGC AAGGGAACTC GATGAATACT CAAGAAAGCA CAAGAGACCC GTTCGTCCAC TCCATGCCT CCCATCTCT
5101 CTCAAAGACC AGCTTCAGT CAAGGTACAC CGTTGCCCCT AAGTCGTTAG ATGTCAGCTA TTGTCAGCTA CCAGGCCTAC GAAACATCAA
5201 TGGGCTACAT CTCATGGCTA AACAAGTACG ACGAAGGGGA CTCGGTTCTG ACAACCATGC TCCGCAAAGC CGGTGCCGTC TTCTACGTCA AGACCTCTGT
5301 CCCAGAGACC CTGATGGTCT GCCAGACAGT CAACAACATC ATCGGGCGCA CCGTCAACCC ACGCAACAAG AACTGGTCGT GCCGGCCAG TTCTGGTGGT
5401 GAGGGTGCGA TCGTTGGGAT TCGTGGTGGC GTCATCGGTG TAGGAACGGA TATCGGTGGC GAGGGTGCA TCGGTTGTC GCCGGCCGC GTTCAACTTC CTGTACGGTC
5501 TAAGGCCGAG TCATGGGCGG CTGCCGTATG CAAAGATGGC TCCACTGTCC GAGGGTCAGG CAGCGGTGCA CAGCGTTGTC GGGCCGATTA CGCACTCTGT
5601 TGAGGGTGAG TCCTTCGCCT CTTCCTTCTT TTCCTGCTCT ATACCAGGCC TCCACTGTCC TCCTTTCTTG CTTTTATAC TATATACGAG ACCGGCAGTC
5701 ACTGATGAAG TATGTTAGAC CTCCGCCTCT TCACCAAATC CGTCCTCGGT GGAGGCCAT GAAATACGA CTCCAAGGTC ATCCCCATGC CCTGGCGCCA
5801 GTCCGAGTCG GACATTATTG CCTCCAAGAT CAAGAACGGC CTCACCACCG TCGGCTACTA CAACTTCGAC GGCAATGTCC TTCCACACCC TCCTATCCTG
5901 CGGGCGTGG AAACCACCGT CGCGCACTC GCCGCCAAGG AAACCCCGT GACCCCGTGG ACGCCATACA AGCCGATTT CGGCCACGAT CTCATCTCCC
6001 ATATCTACGC GGCTGACGGC AGCTCTGGGA TAATGCGCGA TATCAGTGCA TCCGGAGAGC GGCCGATTCC AATATATCAA GACCTACTGA ACCCGAACAT
6101 CAAAGCTGTT AACATGAACG AGCTCTGGGA ACGGCATCTC CAGAAGTGGA ATTACCAGAT GGAGTACCTT GAGAAATGGC GGGAGGCTGA AGAAAAGCC
6201 GGGAAGGAAC TGGACCCCAT CTTCGCGCCG ATTACGCCTA CCGGCATGAC CAGTTCCGGT ACTATGGGTA TGCCCTCGTG AGAGGCCTGA AGAAAAGCC
6301 TGGATTTCAC GAGCGTGGTT GTTCCGGTTA CCTTTGCGGA TAAGAACATC GATAAGAAGA GATGAGTTT CAAGGCCGTT AGTGAGCTTG ATGCCCTCGT
6401 GCAGGAAGAG TATGATCCGG AGGCGTACCA TGGGCACCG GTTCAGTGC AGTTATCGG ACGAGACTC AGTGAAGAGA GGACGTTGC GATTGCAGAG
6501 GAAGGTATGG AATGTTGGTG ACTCCATAGC TAATAGTGT CAGATAGCA TTTGCACACG AAATCAATAC CAGCACTGT AAATAAGCGC
6601 TGAGTGACC ATGCCATGCT ACGAAAGAGC CTGCCTAGA ACCGAAGAGA TATGACACGC TTCCATCTCT CAAAGAAGA ATCCCTTCAG
6701 GGTTGCGTTT CCAGT
```

FIG. 13A Continued

```
   1 ATTAAGGCCA TTTAGGCCGT TGCTGGCCGT TTTCCATAGG CTCCGCCCCC CTGACGAGCA TCACAAAAAT CGACGCTCAA GTCAGAGGTG GCGAAACCCG
 101 ACAGGACTAT AAAGATACCA GGCGTTTCCC CCTGGAAGCT CCCTCGTGCG CTCTCCTGTT CCGACCCTGC CGCTTACCGG ATACCTGTCC GCCTTTCTCC
 201 CTTCGGGAAG CGTGGCGCTT TCTCATAGCT CACGCTGTAG GTATCTCAGT TCGGTGTAGG TCGTTCGCTC CAAGCTGGGC TGTGTGCACG AACCCCCCGT
 301 TCAGCCCGAC CGCTGCGCCT TATCCGGTAA CTATCGTCTT GAGTGCAAGC CGGTAAGACA CGACTTATCG CCACTGGCAG CAGCCACTGG TAACAGGATT
 401 AGCAGAGCGA GGTATGTAGG CGGTGCTACA GAGTTCTTGA AGTGGTGGCC CGGCAAACAA ACCACCGCTG GTAGCGGTGG TTTTTTTGT TGCAAGCAGC AGATTACGCG
 501 AGCCAGTTAC CTTCGGAAAA AGAGTTGGTA GCTCTTGATC GATCTTTCT ACGGGGTCTG AACGAAAAC TCACGTTAAG GCCTGCAGGG CCGATTTTGG
 601 CAGAAAAAAA GGATCTCAAG AAGATCCTTT GATCTTTTCT ACGTATAAGC TGAAGTTTTA AATCAATCTA AAGTATATAT GAGTAAACTT GGTCTGACAG
 701 TCATGAGATT ATCAAAAAGG ATCTTCACCT AGATCCTTT AAATTAAAAA TGAAGTTTTA AATCAATCTA AAGTATATAT GAGTAAACTT GGTCTGACAG
 801 TTACCAATGC TTAATCAGTG AGGCACCTAT CTCAGCGATC TGTCTATTTC GTTCATCCAT AGTTGCCTGA CTCCCCGTCG TGTAGATAAC TACGATACGG
 901 GAGGGCTTAC CATCTGGCCC CAGTGCTGCA ATGATACCGC GAGACCCACG CTCACCGGCT CCAGATTTAT CAGCAATAAA CCAGCCAGCC GGAAGGGCCG
1001 AGCGCAGAAG TGGTCCTGCA ACTTTATCCG CCTCCATCCA GTCTATTAAT TGTTGCCGGG AAGCTAGAGT AAGTAGTTCG CCAGTTAATA GTTTGCGCAA
1101 CGTTGTTGCC ATTGCTACAG GCATCGTGGT GTCACGCTCG TCGTTTGGTA TGGCTTCATT CAGCTCCGGT TCCCAACGAT CAAGGCGAGT TACATGATCC
1201 CCCATGTTGT GCAAAAAAGC GGTTAGCTCC TTCGGTCCTC CGATCGTTGT CAGAAGTAAG TTGGCCGCAG TGTTATCACT CATGGTTATG GCAGCACTGC
1301 ATAATTCTCT TACTGTCATG CCATCCGTAA GATGCTTTTC TGTGACTGGT GAGTACTCAA CCAAGTCATT CTGAGAATAG TGTATGCGGC GACCGAGTTG
1401 CTCTTGCCCG GCGTCAATAC GGGATAATAC CGCGCCACAT GGCGCCACAT AAAAGTGCT CATCATTGGA AAACGTTCTT CGGGGCGAAA ACTCTCAAGG
1501 ATCTTACCGC TGTTGAGATC CAGTTCGATG TAACCCACTC GTGCACCCAA CTGATCTTCA GCATCTTTTA CTTTCACCAG CGTTTCTGGG TGAGCAAAAA
1601 CAGGAAGGCA AAATGCCGCA AAAAAGGGAA TAAGGGCGAC ACGGAAATGT TGAATACTCA TACTCTTCCT TTTTCAATAT TATTGAAGCA TTTATCAGGG
1701 TTATTGTCTC ATGAGCGGAT ACATATTTGA ATGTATTTAG AAAAATAAAC AAATAGGGGT TCCGCGCACA TTTCCCCGAA AAGTGCCACC TGACGTCTAA
1801 GAAACCATTA TTATCATGAC ATTAACCTAT AAAAATAGGC GTATCACGAG GCCCTTTCGT CTTCAAGAAT TCCACCATAT
```

*FIG. 13B*

```
3301 CTGGCTGCTG TCTGCCCTAC CGGCCTCTTC TCCAACCCTC TGTGCTGTGC CACCAAGTTC CTCGACCTCA TTGGCGTTGA CTGCAAGACC CGTATGTTGA
3401 ATTCCAATCT CTGGGCATCC TGACAATTGGA CGATACAGTT GACTTACACG ATGCTTTACA GCTACCATCG CCGTCGACAC TGGCGCCATC TTCCAGGCTC
3501 ACTGTGCCAG CAAGGGCTCC AAGCCTCTTT GCTGCGTTGC TCCGTTGGTA AGTAGTGCTC GCAATGCCAA AGAAGTAAAA AGACATTTGG GCCTGGGATC
3601 GCTAACTCTT GATATCAAGG CCGACCAGGC TCTCCTGTGC CAGAAGGCCA TCGGCACCTT CTAAAGCAAT GGCTTGCTTT ACTGCCGGCA GTCTTTGAGA
3701 ACTAAGGGTG GGCGCGCCGA CCCAGCTTTC TTGTACAAAG TGGTGATCGC GCCAAAGCC TGACGCACCG TGACGCACCG TGAGATTCTT GGTGAGCCCG
3801 TATCATGACG GCGGCGGGAG CTACATGGCC CTACATGGCC TATTTTTTTT GTATTCTACTT TCAAATATAC GGTCAACTCA TCTTTCACTG
3901 GAGATGCGGC CTGCTTGGTA TTGCGATGTT GTCAGCTTGG CAAATTGTGG CTTTCGAAAA CACAAAACGA TCCTTAGTA GCCATGCATT TTAAGATAAC
4001 GGAATAGAAG AAAGAGGAAA TTAAAAAAAA GAATAATAAT AACATCCCGT TCATAACCCG TAGAATCGCC GCTCTTCGGC TAGCTAGTTA CGCTTGTTTA
4101 TTTACGACAA GATCTAGAAG ATTCGAGATA GCCTTGTACT TGGCACGGTA ATCCTCCGTG TCTTTGATAT CCTCAGGGGT TTTTCAGTCT TACTCCCCT TCTGACATTG
4201 AACGCCTCCA TCAGTCAGTC GCCTTGTACT TGGCACGGTA ATCCTCCGTG TCTTTGATAT CCTCAGGGGT AGCAAAGCCC TTCATGCCAT CGATAATGTC
4301 ATCCAGAGTG AGGATGGCAA AGATGGGCAT GCCGTACTCC TTCCCAGCT CGCCAATGGC ACTCGGTCCA GGCTTGGAGT CGTCGCCATC CGCAGCGGGG
4401 AGCTTCTCCA TGCGGTCCAG GGCCACGACG ATGCCGGCGA CGATGCGCGCC CTCCTTGGTG ATCTTCTCAA TGGCGTCCCT CTTGGCGGTG CCGGCGGTGA
4501 TGACGTCGTC GACAATCAGG ACCCTCTTGC CCTTGAGCGA AGCCCCGACG AGCCCCGACG ATGTTGCCGC CCTCGCCGTG GTCCTTGCGT TCCTTGGCC CAAACGAGTA
```

*FIG. 13B Continued*

SEQUENCE LISTING

```
<160> NUMBER OF SEQ ID NOS: 35

<210> SEQ ID NO 1
<211> LENGTH: 3551
<212> TYPE: DNA
<213> ORGANISM: Artificial Sequence
<220> FEATURE:
<223> OTHER INFORMATION: synthetic sequence

<400> SEQUENCE: 1
agcttggggt ggtggccaat cagcggccgc agcgggggcg ggagctggtg gcggcgatat      60
gaatttccgg gcgttgctac aacaggtacc actttgacca cccatggctg ccgtcgccct     120
gcttggagct ttcaggtcgc ttccgggcgt tggcgaggca agttggacgg tggggaaatg     180
```

```
acgaaaaatg gtgcatcgcc tttgtaggtg tgtgtgagta gtagttctac tatgaggtac    240
gtatgtagca gaaggatcga gctagaatct gccggcattg caaaggttat ctggaaagag    300
gaaaagggcc tgaaccggca tatggatgca ttcttcgtac gaactactat ctgataacag    360
ttaggtactg ttatccatac aaagagtctt atagaaacac tgcatcgtaa taaaatactc    420
ggtagctgct tgaatatagt aataagatca acatcctttc acctctagtc tccgtggatt    480
ccagtaaaag cgctcaattc tgacttccga ctctgttgat gccccgtgtc tgcccatcgg    540
ggtggtctag acgctgcctc aacgcccatg taccggcctg atggggccct tggggcacc    600 acaagtccac taaacgaagc actggggacg ggactcgata gccctgagca gcagccggtc    660
tcagcagcca accagcccag ctggaagcat cggctagggg agggggccc aactactacg    720 tgtactacta ggtacataat gaattggatg ggacccagcc agcccaacct aactttccag    780
cctttatagc tgcagcctgc ttccccgtgc ctcacgcttt ttgctcctct gctggccgga    840
ctcggacctc ttgcgacctc tgctcgacca caatccctc ttgttgcacc ctctcgcttt    900
tgctacctcg acgctcaatt cctcgctgcc gcctcaccta accgcgtgtg cttgactgcc    960
ctcacgctcg gctcgcctcc tgctccgcga gcctcctttt acacttttca acagctaccc   1020
cgccagaatt caaacatgtc gccttccatg cagacgcggg cctccgttgt catcgactac   1080
aatgtcgcac ctccaaacct atccactctg cccaatggct ccctcttcga acatggcgt   1140 ccccgcgccc acgtcctgcc ccccaacggc cagatcggtg acccctgcct gcattacacc   1200
gatccctcca cgggcctctt ccacgtcggc ttccttcacg atggcagcgg catctccagc   1260
gccaccactg atgatctagc cacctacaag gacctcaacc aaggcaacca agtcattgtt   1320
cccgggggta tcaacgaccc cgtcgccgtc ttcgatggct ccgtcatccc cagcggcatc   1380 aacgcctcc ccactctcct ctacacctcc gtctccttcc ttcccatcca ctggtccatc   1440
ccctacaccc gcggcagtga cccaatcc ctcgctgtct cctcggatgg cggcagcaac   1500
ttcaccaagc tcgaccaggg ccccgtcatc cctggccctc ccttcgccta caacgtcacc   1560
gcattccggg accctacgt cttccaaaac cccacctcg actccctcct gcacagcaag   1620
aacaacacct ggtataccgt catctccggt ggtctgcacg gcaagggccc cgcccagttc   1680
ctctaccgcc agtacgaccc ggacttccag tactgggagt tcctcggcca atggtggcac   1740
gagcccacca actccacttg gggtaacggc acctgggccg gccgatgggc cttcaacttc   1800
gagaccggca acgtcttcag tctcgacgag tacggataca accccacgg ccagatcttc   1860 tccacgatcg gcaccgaggg ctctgaccag cccgtcgtgc cccagctcac cagcatccac   1920
gacatgctct gggtgtccgg caacgtctct cgcaatggct ctgtctcgtt caccccgaac   1980
atggcgggct cctcgactg gggcttctcc tcttacgcag ctgccggaaa ggtcctcccc   2040
tcgacttctc tgccctcgac gaagagcggc gccccggacc gcttcatctc gtacgtctgg   2100
ctgtccggtg acctgttcga acaggccgaa gggttcccca cgaaccagca gaattggacc   2160
ggtacgctgt tgcttccgcg agagttgcgc gtgctgtata tccccaatgt ggtggacaat   2220
gctctggctc gggaatctgg tgcctcgtgg caggtcgtga gcagcgatag cagtgcgggc   2280
accgtggagc tgcagacact gggtatctcc attgcccggg aaaccaaggc cgccttgctg   2340
tcgggaacgt cgttcaccga gtccgaccgt actctgaaca gcagtggtgt tgtgccgttc   2400
aagcgctccc cgtccgagaa gttctttgtt ttgtccgcgc agctgtcctt ccctgcttcg   2460
gctaggggat cgggactcaa aagtggattc cagatcctct cgtcggagct ggaaagcacc   2520
actgtctact accagttctc gaatgagtcg attattgtcg accgcagtaa caccagtgct   2580
```

```
gcggcgcgta ccacggatgg tatcgatagc agtgcggagg ctggcaagtt gcgcctgttt    2640
gacgtgttga atggcggaga gcaggcgatt gagacgttgg atttgactct cgtggtggat    2700
aactcggtat tggagatcta tgccaatggt cggtttgcgt tgagtacttg ggttcggtga    2760
gtatcttcct attttatcaa tgaagtgttt atgatgctaa cgtggggata gttcttggta    2820
cgccaattcc acgaacatca gtttcttcca gaatggcgtg gtggtgttg cgttctccaa     2880 cgtgaccgtt tccagggct tgtatgatgc ttggccggat cgtcagtctt aatcagtctt     2940
gaggtgatgc ctaagtagta tcaaggatca ctccaggtca ggtcatactg atccgacagt    3000
taatgtcaga tgcatcgcgt tcaagaagaa cggcagacat taatcatgag gtgcagcaaa    3060 gaagggctc cccgttcttc gcagcccta ccatgaacgc cgatgaggcc gggtctattg      3120
acaatattat tttccttctt aacaactgtt ttattatatc acaagaatca aagaaatcca    3180
agccagactg caattccgtc aacaataacg ccatcgctat gtaaattgcc ccagttgttt    3240
tcccttcccg atactttact gaactgatac acgatgaaga cttgtactcg acgttcgcgg    3300
tgaaatatga ctcggtcgga gaggagctac tcccagctcg tcaatctgcg aacaggctt     3360 cctttgcccg acaagttgcg cggacccgtt ccctgactct gagggtgcgg aatatgaatg    3420
tgcacgtggt gcctgtggac cggggtacgc tacgatactc ccctcgctg gctgatcaga     3480 cactgtcgag tatgtgctta gtggttgata ctgagccggc ggggtcaatg tcgtagcagg    3540
tgaagtttcg g                                                         3551

<210> SEQ ID NO 2
<211> LENGTH: 2223
<212> TYPE: DNA
<213> ORGANISM: Artificial Sequence
<220> FEATURE:
<223> OTHER INFORMATION: synthetic pFIX plasmid

<400> SEQUENCE: 2
ctagaggcct aaatggccat gagacaataa ccctgataaa tgcttcaata atattgaaaa    60
aggaagagta tgagtattca acatttccgt gtcgccctta ttccctttt tgcggcattt      120 tgccttcctg ttttgctca cccagaaacg ctggtgaaag taaaagatgc tgaagatcag      180
ttgggtgcac gagtgggtta catcgaactg gatctcaaca gcggtaagat ccttgagagt     240
tttcgccccg aagaacgttt tccaatgatg agcactttta aagttctgct atgtggcgcg     300
gtattatccc gtattgacgc cgggcaagag caactcggtc gccgcataca ctattctcag     360
aatgacttgg ttgagtactc accagtcaca gaaaagcatc ttacggatgg catgacagta     420
agagaattat gcagtgctgc cataaccatg agtgataaca ctgcggccaa cttacttctg    480
acaacgatcg gaggaccgaa ggagctaacc gcttttttgc acaacatggg gatcatgta     540 actcgccttg atcgttggga accggagctg aatgaagcca taccaaacga cgagcgtgac    600
accacgatgc ctgtagcaat ggcaacaacg ttgcgcaaac tattaactgg cgaactactt    660
actctagctt cccggcaaca attaatagac tggatggagg cggataaagt tgcaggacca    720
cttctgcgct cggcccttcc ggctggctgg tttattgctg ataaatctgg agccggtgag    780
cgtgggtctc gcggtatcat tgcagcactg gggccagatg gtaagccctc ccgtatcgta    840
gttatctaca cgacggggag tcaggcaact atggatgaac gaaatagaca gatcgctgag    900
ataggtgcct cactgattaa gcattggtaa ctgtcagacc aagtttactc atatatactt    960
tagattgatt taaaacttca ttttttaatttt aaaaggatct aggtgaagat cctttttgat    1020
```

```
aatctcatga ccaaaatccc ttaacgtgag ttttcgttcc actgagcgtc agaccccgta    1080
gaaaagatca aaggatcttc ttgagatcct ttttttctgc gcgtaatctg ctgcttgcaa    1140
acaaaaaaac caccgctacc agcggtggtt tgtttgccgg atcaagagct accaactctt    1200
tttccgaagg taactggctt cagcagagcg cagataccaa atactgtcct tctagtgtag    1260
ccgtagttag gccaccactt caagaactct gtagcaccgc ctacatacct cgctctgcta    1320
atcctgttac cagtggctgc tgccagtggc gataagtcgt gtcttaccgg gttggactca    1380
agacgatagt taccggataa ggcgcagcgg tcgggctgaa cggggggttc gtgcacacag    1440
cccagcttgg agcgaacgac ctacaccgaa ctgagatacc tacagcgtga gctatgagaa    1500
agcgccacgc ttcccgaagg gagaaaggcg gacaggtatc cggtaagcgg cagggtcgga    1560
acaggagagc gcacgaggga gcttccaggg ggaaacgcct ggtatcttta tagtcctgtc    1620
gggtttcgcc acctctgact tgagcgtcga tttttgtgat gctcgtcagg gggcggagc     1680 ctatggaaaa acgccagcaa cgctgcagca tttccccgaa aagtgccacc tgacgcgccc    1740
tgtagcggcg cattaagcgc ggcgggtgtg gtggttacgc gcagcgtgac cgctacactt    1800
gccagcgccc tagcgcccgc tcctttcgct ttcttccctt cctttctcgc cacgttcgcc    1860
ggctttcccc gtcaagctct aaatcggggg ctccctttag ggttccgatt tagtgcttta    1920
cggcacctcg accccaaaaa acttgattag ggtgatggtt cacgtagtgg gccatcgccc    1980
tgatagacgg ttttcgccc tttgacgttg gagtccacgt tctttaatag tggactcttg     2040
ttccaaactg gaacaacact caaccctatc tcggtctatt cttttgattt ataagggatt    2100
ttgccgattt cggcctattg gttaaaaaat gagctgattt aacaaaaatt taacgcgaat    2160
tttaacaaaa tattaacgct tacaatttac gcgttaagat acattgatga gtttgcggcc    2220
gct                                                                  2223

<210> SEQ ID NO 3
<211> LENGTH: 6486
<212> TYPE: DNA
<213> ORGANISM: Artificial Sequence
<220> FEATURE:
<223> OTHER INFORMATION: synthetic sequence

<400> SEQUENCE: 3
gcatttcccc gaaaagtgcc acctgacgcg ccctgtagcg cgcattaag cgcggcgggt      60 gtggtggtta cgcgcagcgt gaccgctaca cttgccagcg ccctagcgcc cgctcctttc    120
gctttcttcc cttcctttct cgccacgttc gccggctttc cccgtcaagc tctaaatcgg    180
gggctccctt tagggttccg atttagtgct ttacggcacc tcgaccccaa aaaacttgat    240
tagggtgatg gttcacgtag tgggccatcg ccctgataga cggttttttcg ccctttgacg    300 ttggagtcca cgttctttaa tagtggactc ttgttccaaa ctggaacaac actcaaccct    360
atctcggtct attcttttga tttataaggg attttgccga tttcggccta ttggttaaaa    420
aatgagctga tttaacaaaa atttaacgcg aattttaaca aaatattaac gcttacaatt    480
tacgcgttaa gatacattga tgagtttgcg gccgcaattc agatattcca atcatcttg     540 cacgacgtct gaacgaatta atgaagcaaa atagagtatt tcacaggta agtgaggtc     600 agcaggtaat gtgtagatac gcttctcgga acttgaagag cccaagccaa attgaaagtc    660
gaatcagccc gctcctcttt gccgcagcca atagagacgt gcagcctcca tgcatgtaaa    720
gcgggcgaat gtcaccccaac caaccaaccg catcaagcca ccaaatccga gcattgccgg    780
ccgaaattcg actcaagtct cactgaccat aaaaaccccc aacatccctc ttctcgacaa    840
```

| | | | | |
|---|---|---|---|---|
| agagattcaa | acagcaaaaa | aaaatgcaaa | aaaacataca | acagccggtg ttcgccagtg | 900 |
| gtcacccacc | tgactactaa | tctgccggtt | agtggcttgt | ctatggggga gcagacggga | 960 |
| ccccgaattc | tccactacct | atggtcgtat | gtgcttggat | ctctgtggaa tggcttcata | 1020 |
| ttgatggcag | gacgcatatc | ttgatcagtg | cttgtgttcg | gccgatggcg gccatgcgtt | 1080 |
| gctagagcat | gctgttctca | ggcctctgct | ccttgtcatt | acctgtaagg tatagaagct | 1140 |
| gataggtccc | acctctgcgg | actacacatg | gccttgaatc | ctatggatag ggggtgcaac | 1200 |
| gacactctac | aagtcagaag | agtaatagcg | agattggagg | cgagcgccct gcaacactct | 1260 |
| tctcgaatcc | tatcgggata | tcatatacca | attagcctgt | tccaaggtag tatacgttca | 1320 |
| cggaaagagc | tttagcaatt | acaggtgcaa | acatcagcct | gtctggtagg taattagcct | 1380 |
| gttgctgtaa | acctgaagcg | ttgaccctgg | caatagcctg | ttgctataaa cctgaggcgt | 1440 |
| tgaccctggc | aatagcctgt | tgttcatttg | ccctggcgt | tgcaagccgc gtacaactgc | 1500 |
| cctttacct | agtctcgagt | ttataagtga | caacatgctc | tcaaagcgct catggctggc | 1560 |
| acaagcctgg | aaagaaccaa | cacaaagcat | actgcagcaa | atcagctgaa ttcgtcacca | 1620 |
| attaagtgaa | catcaacctg | aaggcagagt | atgaggccag | aagcacatct ggatcgcaga | 1680 |
| tcatggattg | ccctcttgt | tgaagatgag | aatctagaaa | gatggcgggg tatgagataa | 1740 |
| gagcgatggg | ggggcacatc | atcttccaag | acaaacaacc | tttgcagagt caggcaattt | 1800 |
| ttcgtataag | agcaggagga | gggagtccag | tcatttcatc | agcggtaaaa tcactctaga | 1860 |
| caatcttcaa | gatgagttct | gccttgggtg | acttatagcc | atcatcatac ctagacagaa | 1920 |
| gcttgtggga | tactaagacc | aacgtacaag | ctcgcactgt | acgctttgac ttccatgtga | 1980 |
| aaactcgata | cggcgcgcct | ctaaatttta | tagctcaacc | actccaatcc aacctctgca | 2040 |
| tccctctcac | tcgtcctgat | ctactgttca | aatcagagaa | taaggacact atccaaatcc | 2100 |
| aacagaatgg | ctaccacctc | ccagctgcct | gcctacaagc | aggacttcct caaatccgcc | 2160 |
| atcgacggcg | gcgtcctcaa | gtttggcagc | ttcgagctca | gtccaagcg gatatccccc | 2220 |
| tacttcttca | acgcgggcga | attccacacg | gcgcgcctcg | ccggcgccat cgcctccgcc | 2280 |
| tttgcaaaga | ccatcatcga | ggcccaggag | aaggccggcc | tagagttcga catcgtcttc | 2340 |
| ggcccggcct | acaagggcat | cccgctgtgc | tccgccatca | ccatcaagct cggcgagctg | 2400 |
| gcgcccccaga | acctggaccg | cgtctcctac | tcgtttgacc | gcaaggaggc caaggaccac | 2460 |
| ggcgagggcg | gcaacatcgt | cggcgcttcg | ctcaagggca | agagggtcct gattgtcgac | 2520 |
| gacgtcatca | ccgccggcac | cgccaagagg | gacgccattg | agaagatcac caaggagggc | 2580 |
| ggcatcgtcg | ccggcatcgt | cgtggccctg | gaccgcatgg | agaagctccc cgctgcggat | 2640 |
| ggcgacgact | ccaagcctgg | accgagtgcc | attggcgagc | tgaggaagga gtacggcatc | 2700 |
| cccatctttg | ccatcctcac | tctggatgac | attatcgatg | gcatgaaggg ctttgctacc | 2760 |
| cctgaggata | tcaagaacac | ggaggattac | cgtgccaagt | acaaggcgac tgactgattg | 2820 |
| aggcgttcaa | tgtcagaagg | gagagaaaga | ctgaaaaggt | ggaaagaaga ggcaaattgt | 2880 |
| tgttattatt | attattctat | ctcgaatctt | ctagatcttg | tcgtaaataa acaagcgtaa | 2940 |
| ctagctagcc | tccgtacaac | tgcttgaatt | tgatacccgt | atggagggca gttatttat | 3000 |
| tttgttttc | aagattttcc | attcgccgtt | gaactcgtct | cacatcgcgt gtattgcccg | 3060 |
| gttgccatg | tgttctccta | ctaccccaag | tccctcacgg | ttgtctcac tttctttctc | 3120 |
| ctttatcctc | cctatttttt | ttcaagtcag | cgacagagca | gtcatatggg gatacgtgca | 3180 |

```
actgggactc acaacaggcc atcttatggc ctaatagccg gcgttggatc cactagagcc  3240
gacgagtatc gtggggcaat tgcttttctt ctgggggacg cgagttcgta tgtcactggg  3300
acggatctgc ggattgacgg aggatcgacg gggtggtgag aacgtattcg aagatggctt  3360
cacactcaat tatcacatcg tgtatcgatt ttgtgcatag ttttgaagta ggtagctaat  3420
gaaagagctt gacatgtgat atctgagtcg tccctcaccg aggttcactc tcacggtctt  3480
cgtcaacaga ctctctcacg ccccgaatca ccggctgcct cttccaatgc aacacctatc  3540
aagaaacaat cagcaaagaa gaataaagaa gaaacaggcg catcatatca agaaacagaa  3600
tgatactcac ccgtaaatag actcccacat acagcaccaa aagtaccgca tacccaatcc  3660
tcctgaggaa aaacatccct gatcccgaga acacgcacaa gaagacccac gtcagagaag  3720
acaaagcgaa gatatccggc gccttaatga attcagatat tccaaatcat cttgcacgac  3780
gtcgagctcc ggcgcattcc cgtggcaggt aaacattcga ccttgtctgg ggcaagggac  3840
tcgtcactta catcctctct ctctctgcag ctcggcatcg gcaacggagt ctacacggct  3900
gccggctccc aggctctctt cgacacggcc ggagcttcat ggtgcggcgc cggctgcggt  3960
aaatgctacc agctcacctc gacgggccag gcgccctgct ccagctgcgg cacgggcggt  4020
gctgctggcc agagcatcat cgtcatggtg accaacctgt gcccgaacaa tgggaacgcg  4080
cagtggtgcc cggtggtcgg cggcaccaac caatacggct acagctacca tttcgacatc  4140
atggcgcaga acgagatctt tggagacaat gtcgtcgtcg actttgagcc cattgcttgc  4200
cccgggcagg ctgcctctga ctgggggacg tgcctctgcg tgggacagca agagacggat  4260
cccacgcccg tcctcggcaa cgacacgggc tcaactcctc ccgggagctc gccgccagcg  4320
acatcgtcga gtccgccgtc tggcggcggc cagcagacgc tctatggcca gtgtggaggt  4380
gccggctgga cgggacctac gacgtgccag gccccaggga cctgcaaggt tcagaaccag  4440
tggtactccc agtgtcttcc ttgagaaggc ccaagatagc catgtctctc tagcattctt  4500
ccggcgtcag tctgatctgc ctatttaatc aggtcagtca atatgtatcc agagataata  4560
aattatgtat attatagcag tactgtatca ttgctgctgt ctgcctgact tcaatgctgc  4620
ttcccctatt ctcgttgcag tagcgttggc gatatgggc agttgaatag taagcggaag  4680
cgaacatcag gagatctcat ctataaccga ctgtcgccta atgagcgcca agcaattccg  4740
ccggcacttg catttggccg atgtattatg ccgtacgatc ccatggccta aatggccatg  4800
agacaataac cctgataaat gcttcaataa tattgaaaaa ggaagagtat gagtattcaa  4860
catttccgtg tcgcccttat tccctttttt gcggcatttt gccttcctgt ttttgctcac  4920
ccagaaacgc tggtgaaagt aaaagatgct gaagatcagt tgggtgcacg agtgggttac  4980
atcgaactgg atctcaacag cggtaagatc cttgagagtt ttcgccccga gaacgttttt  5040
ccaatgatga gcacttttaa agttctgcta tgtggcgcgg tattatcccg tattgacgcc  5100
gggcaagagc aactcggtcg ccgcatacac tattctcaga atgacttggt tgagtactca  5160
ccagtcacag aaaagcatct tacggatggc atgacagtaa gagaattatg cagtgctgcc  5220
ataaccatga gtgataacac tgcggccaac ttacttctga caacgatcgg aggaccgaag  5280
gagctaaccg cttttttgca caacatgggg gatcatgtaa ctcgccttga tcgttgggaa  5340
ccggagctga atgaagccat accaaacgac gagcgtgaca ccacgatgcc tgtagcaatg  5400
gcaacaacgt tgcgcaaact attaactggc gaactactta ctctagcttc ccggcaacaa  5460
ttaatagact ggatggaggc ggataaagtt gcaggaccac ttctgcgctc ggcccttccg  5520
gctggctggt ttattgctga taaatctgga gccggtgagc gtgggtctcg cggtatcatt  5580
```

```
gcagcactgg ggccagatgg taagccctcc cgtatcgtag ttatctacac gacggggagt    5640
caggcaacta tggatgaacg aaatagacag atcgctgaga taggtgcctc actgattaag    5700
cattggtaac tgtcagacca agtttactca tatatacttt agattgattt aaaacttcat    5760
ttttaattta aaaggatcta ggtgaagatc cttttgata atctcatgac caaatccct     5820 taacgtgagt tttcgttcca ctgagcgtca gaccccgtag aaaagatcaa aggatcttct    5880
tgagatcctt tttttctgcg cgtaatctgc tgcttgcaaa caaaaaaacc accgctacca    5940
gcggtggttt gtttgccgga tcaagagcta ccaactcttt ttccgaaggt aactggcttc    6000
agcagagcgc agataccaaa tactgtcctt ctagtgtagc cgtagttagg ccaccacttc    6060
aagaactctg tagcaccgcc tacatacctc gctctgctaa tcctgttacc agtggctgct    6120
gccagtggcg ataagtcgtg tcttaccggg ttggactcaa gacgatagtt accggataag    6180
gcgcagcggt cgggctgaac ggggggttcg tgcacacagc ccagcttgga gcgaacgacc    6240
tacaccgaac tgagatacct acagcgtgag ctatgagaaa gcgccacgct tcccgaaggg    6300
agaaaggcgg acaggtatcc ggtaagcggc agggtcggaa caggagagcg cacgagggag    6360
cttccagggg gaaacgcctg gtatctttat agtcctgtcg gtttcgcca cctctgactt     6420 gagcgtcgat ttttgtgatg ctcgtcaggg gggcggagcc tatggaaaaa cgccagcaac    6480
gctgca                                                              6486

<210> SEQ ID NO 4
<211> LENGTH: 40
<212> TYPE: DNA
<213> ORGANISM: Artificial Sequence
<220> FEATURE:
<223> OTHER INFORMATION: synthetic primer

<400> SEQUENCE: 4
ggaattcaaa catgtcgcct tccatgcaga cgcgggcctc                          40

<210> SEQ ID NO 5
<211> LENGTH: 36
<212> TYPE: DNA
<213> ORGANISM: Artificial Sequence
<220> FEATURE:
<223> OTHER INFORMATION: synthetic primer

<400> SEQUENCE: 5
gttggcgcgc ctggatcccg aaacttcacc tgctac                              36

<210> SEQ ID NO 6
<211> LENGTH: 27
<212> TYPE: DNA
<213> ORGANISM: Artificial Sequence
<220> FEATURE:
<223> OTHER INFORMATION: synthetic primer

<400> SEQUENCE: 6
cgataagcga ttggcgagcg agctttg                                        27

<210> SEQ ID NO 7
<211> LENGTH: 33
<212> TYPE: DNA
<213> ORGANISM: Artificial Sequence
<220> FEATURE:
<223> OTHER INFORMATION: synthetic primer

<400> SEQUENCE: 7
```
ggtgaattct ggcggggtag ctgttgaaaa gtg                                          33

<210> SEQ ID NO 8
<211> LENGTH: 54
<212> TYPE: DNA
<213> ORGANISM: Artificial Sequence
<220> FEATURE:
<223> OTHER INFORMATION: synthetic primer

<400> SEQUENCE: 8
gtttcggcca tttaggccgg atccacacct tgctcctgtc gcatgcgtat ctgg              54

<210> SEQ ID NO 9
<211> LENGTH: 49
<212> TYPE: DNA
<213> ORGANISM: Artificial Sequence
<220> FEATURE:
<223> OTHER INFORMATION: synthetic primer

<400> SEQUENCE: 9
gtttgcggcc gcggatcctg ctcagcacaa tgtccagaaa ctcctggtg                   49

<210> SEQ ID NO 10
<211> LENGTH: 30
<212> TYPE: DNA
<213> ORGANISM: Artificial Sequence
<220> FEATURE:
<223> OTHER INFORMATION: synthetic primer

<400> SEQUENCE: 10
gccggatcca caccttgctc ctgtcgcatg                                              30

<210> SEQ ID NO 11
<211> LENGTH: 30
<212> TYPE: DNA
<213> ORGANISM: Artificial Sequence
<220> FEATURE:
<223> OTHER INFORMATION: synthetic primer

<400> SEQUENCE: 11
gcaggatccg cggccgcaaa ctcatcaatg                                              30

<210> SEQ ID NO 12
<211> LENGTH: 29
<212> TYPE: DNA
<213> ORGANISM: Artificial Sequence
<220> FEATURE:
<223> OTHER INFORMATION: synthetic primer

<400> SEQUENCE: 12
gcgtggtttc agcagcccac tggtgagtg                                               29

<210> SEQ ID NO 13
<211> LENGTH: 29
<212> TYPE: DNA
<213> ORGANISM: Artificial Sequence
<220> FEATURE:
<223> OTHER INFORMATION: synthetic primer

<400> SEQUENCE: 13
gccagactgc aattccgtca acaataacg                                               29

<210> SEQ ID NO 14
<211> LENGTH: 29
<212> TYPE: DNA
<213> ORGANISM: Artificial Sequence
<220> FEATURE:
<223> OTHER INFORMATION: synthetic primer

<400> SEQUENCE: 14
agccggcacg gatctgagtg ggcagtttg                              29

<210> SEQ ID NO 15
<211> LENGTH: 29
<212> TYPE: DNA
<213> ORGANISM: Artificial Sequence
<220> FEATURE:
<223> OTHER INFORMATION: synthetic primer

<400> SEQUENCE: 15
ggtttggagg tgcgacattg tagtcgatg                              29

<210> SEQ ID NO 16
<211> LENGTH: 39
<212> TYPE: DNA
<213> ORGANISM: Artificial Sequence
<220> FEATURE:
<223> OTHER INFORMATION: synthetic primer

<400> SEQUENCE: 16
gttgcggccg caattcagat attccaaatc atcttgcac                   39

<210> SEQ ID NO 17
<211> LENGTH: 40
<212> TYPE: DNA
<213> ORGANISM: Artificial Sequence
<220> FEATURE:
<223> OTHER INFORMATION: synthetic primer

<400> SEQUENCE: 17
gtggccattt aggccatggg atcgtacggc ataatacatc                  40

<210> SEQ ID NO 18
<211> LENGTH: 50
<212> TYPE: DNA
<213> ORGANISM: Artificial Sequence
<220> FEATURE:
<223> OTHER INFORMATION: synthetic primer

<400> SEQUENCE: 18
gttactagtc tcgagttttc tagagccgac gagtatcgtg gggcaattgc       50

<210> SEQ ID NO 19
<211> LENGTH: 34
<212> TYPE: DNA
<213> ORGANISM: Artificial Sequence
<220> FEATURE:
<223> OTHER INFORMATION: synthetic primer

<400> SEQUENCE: 19
gttgtcgacg tcgtgcaaga tgatttggaa tatc                        34

<210> SEQ ID NO 20
<211> LENGTH: 40
<212> TYPE: DNA
<213> ORGANISM: Artificial Sequence
<220> FEATURE:
<223> OTHER INFORMATION: synthetic primer

<400> SEQUENCE: 20
agtactagtc aattgctcga gtttataagt gacaacatgc                  40

<210> SEQ ID NO 21
<211> LENGTH: 44
<212> TYPE: DNA
<213> ORGANISM: Artificial Sequence
<220> FEATURE:
<223> OTHER INFORMATION: synthetic primer

<400> SEQUENCE: 21
ttgcaattga ctagtggatc caacgccggc tattaggcca taag        44

<210> SEQ ID NO 22
<211> LENGTH: 30
<212> TYPE: DNA
<213> ORGANISM: Artificial Sequence
<220> FEATURE:
<223> OTHER INFORMATION: synthetic primer

<400> SEQUENCE: 22
aattaatgaa gcaaaataga gtattttcac        30

<210> SEQ ID NO 23
<211> LENGTH: 30
<212> TYPE: DNA
<213> ORGANISM: Artificial Sequence
<220> FEATURE:
<223> OTHER INFORMATION: synthetic primer

<400> SEQUENCE: 23
gatcgtacgg cataatacat cggccaaatg        30

<210> SEQ ID NO 24
<211> LENGTH: 31
<212> TYPE: DNA
<213> ORGANISM: Artificial Sequence
<220> FEATURE:
<223> OTHER INFORMATION: synthetic primer

<400> SEQUENCE: 24
cctagatccg ggaattccca tgggatcgta c        31

<210> SEQ ID NO 25
<211> LENGTH: 31
<212> TYPE: DNA
<213> ORGANISM: Artificial Sequence
<220> FEATURE:
<223> OTHER INFORMATION: synthetic primer

<400> SEQUENCE: 25
ctgacagcga gctaccttac atgtacataa g        31

<210> SEQ ID NO 26
<211> LENGTH: 32
<212> TYPE: DNA
<213> ORGANISM: Artificial Sequence
<220> FEATURE:
<223> OTHER INFORMATION: synthetic primer

<400> SEQUENCE: 26
ggcgcatcat atcaagaaac agaatgatac tc        32

<210> SEQ ID NO 27
<211> LENGTH: 31
<212> TYPE: DNA
<213> ORGANISM: Artificial Sequence
<220> FEATURE:
<223> OTHER INFORMATION: synthetic primer

```
<400> SEQUENCE: 27
cacaagaaga cccacgtcag agaagacaaa g                              31

<210> SEQ ID NO 28
<211> LENGTH: 30
<212> TYPE: DNA
<213> ORGANISM: Artificial Sequence
<220> FEATURE:
<223> OTHER INFORMATION: synthetic primer

<400> SEQUENCE: 28
ggaagaagcc atgctcaagc gcatttctac                                30

<210> SEQ ID NO 29
<211> LENGTH: 30
<212> TYPE: DNA
<213> ORGANISM: Artificial Sequence
<220> FEATURE:
<223> OTHER INFORMATION: synthetic primer

<400> SEQUENCE: 29
atcgccacgc caatgaccca gcagtttctc                                30

<210> SEQ ID NO 30
<211> LENGTH: 30
<212> TYPE: DNA
<213> ORGANISM: Artificial Sequence
<220> FEATURE:
<223> OTHER INFORMATION: synthetic primer

<400> SEQUENCE: 30
gaaaaggtgg aaagaagagg caaattgttg                                30

<210> SEQ ID NO 31
<211> LENGTH: 30
<212> TYPE: DNA
<213> ORGANISM: Artificial Sequence
<220> FEATURE:
<223> OTHER INFORMATION: synthetic primer

<400> SEQUENCE: 31
gagttttcac atggaagtca aagcgtacag                                30

<210> SEQ ID NO 32
<211> LENGTH: 1124
<212> TYPE: DNA
<213> ORGANISM: Trichoderma reesei

<400> SEQUENCE: 32
cgtatcttac acaagggcgc tgcaactaat tgacttgatc ttccatctcg tgtcttgctt    60
gtaaccatcg tgaccatgaa ggcaactctg gttctcggct ccctcattgt aggcgccgtt   120
tccgcgtaca aggccaccac cacggcaagt ctacatgctt ccaggtcaca acgtctgctc   180
aacaacctct aaccgaaagg ccagcgctac tacgatgggc aggagggtgc ttgcggatgc   240
ggctcgagct ccggcgcatt cccgtggcag gtaaacattc gaccttgtct ggggcaaggg   300
actcgtcact tacatcctct ctctctctgc agctcggcat cggcaacgga gtctacacgg   360
ctgccggctc ccaggctctc ttcgacacgg ccggagcttc atggtgcggc gccggctgcg   420
gtaaatgcta ccagctcacc tcgacgggcc aggcgccctg ctccagctgc ggcacgggcg   480
gtgctgctgg ccagagcatc atcgtcatgg tgaccaacct gtgcccgaac aatgggaacg   540
```

```
cgcagtggtg cccggtggtc ggcggcacca accaatacgg ctacagctac catttcgaca    600
tcatggcgca gaacgagatc tttggagaca atgtcgtcgt cgactttgag cccattgctt    660
gccccgggca ggctgcctct gactggggga cgtgcctctg cgtgggacag caagagacgg    720
atcccacgcc cgtcctcggc aacgacacgg gctcaactcc tcccgggagc tcgccgccag    780
cgacatcgtc gagtccgccg tctggcggcg gccagcagac gctctatggc cagtgtggag    840
gtgccggctg gacgggacct acgacgtgcc aggcccagg gacctgcaag gttcagaacc    900
agtggtactc ccagtgtctt ccttgagaag gcccaagata gccatgtctc tctagcattc    960
ttccggcgtc agtctgatct gcctatttaa tcaggtcagt caatatgtat ccagagataa    1020
taaattatgt atattatagc agtactgtat cattgctgct gtctgcctga cttcaatgct    1080
gcttccccta ttctcgttgc agtagcgttg gcgatatggg gcag                    1124
```

<210> SEQ ID NO 33
<211> LENGTH: 242
<212> TYPE: PRT
<213> ORGANISM: Trichoderma reesei

<400> SEQUENCE: 33

```
Met Lys Ala Thr Leu Val Leu Gly Ser Leu Ile Val Gly Ala Val Ser
1               5                   10                  15

Ala Tyr Lys Ala Thr Thr Thr Arg Tyr Tyr Asp Gly Gln Glu Gly Ala
            20                  25                  30

Cys Gly Cys Gly Ser Ser Ser Gly Ala Phe Pro Trp Gln Leu Gly Ile
        35                  40                  45

Gly Asn Gly Val Tyr Thr Ala Ala Gly Ser Gln Ala Leu Phe Asp Thr
    50                  55                  60

Ala Gly Ala Ser Trp Cys Gly Ala Gly Cys Gly Lys Cys Tyr Gln Leu
65                  70                  75                  80

Thr Ser Thr Gly Gln Ala Pro Cys Ser Ser Cys Gly Thr Gly Gly Ala
                85                  90                  95

Ala Gly Gln Ser Ile Ile Val Met Val Thr Asn Leu Cys Pro Asn Asn
            100                 105                 110

Gly Asn Ala Gln Trp Cys Pro Val Val Gly Gly Thr Asn Gln Tyr Gly
        115                 120                 125

Tyr Ser Tyr His Phe Asp Ile Met Ala Gln Asn Glu Ile Phe Gly Asp
    130                 135                 140

Asn Val Val Asp Phe Glu Pro Ile Ala Cys Pro Gly Gln Ala Ala
145                 150                 155                 160

Ser Asp Trp Gly Thr Cys Leu Cys Val Gly Gln Glu Thr Asp Pro
                165                 170                 175

Thr Pro Val Leu Gly Asn Asp Thr Gly Ser Thr Pro Gly Ser Ser
            180                 185                 190

Pro Pro Ala Thr Ser Ser Pro Ser Gly Gly Gly Gln Gln Thr
        195                 200                 205

Leu Tyr Gly Gln Cys Gly Gly Ala Gly Trp Thr Gly Pro Thr Thr Cys
    210                 215                 220

Gln Ala Pro Gly Thr Cys Lys Val Gln Asn Gln Trp Tyr Ser Gln Cys
225                 230                 235                 240

Leu Pro
```

<210> SEQ ID NO 34
<211> LENGTH: 6715
<212> TYPE: DNA

<213> ORGANISM: Artificial Sequence
<220> FEATURE:
<223> OTHER INFORMATION: synthetic pTrex3gM(Hfb2) plasmid

<400> SEQUENCE: 34

```
ctagaggcca tttaggccgt tgctggcgtt tttccatagg ctccgccccc ctgacgagca      60
tcacaaaaat cgacgctcaa gtcagaggtg gcgaaacccg acaggactat aaagatacca     120
ggcgttcc cctggaagct ccctcgtgcg ctctcctgtt ccgaccctgc cgcttaccgg       180
atacctgtcc gcctttctcc cttcgggaag cgtggcgctt tctcatagct cacgctgtag    240
gtatctcagt tcggtgtagg tcgttcgctc caagctgggc tgtgtgcacg aaccccccgt     300
tcagcccgac cgctgcgcct tatccggtaa ctatcgtctt gagtccaacc cggtaagaca    360
cgacttatcg ccactggcag cagccactgg taacaggatt agcagagcga ggtatgtagg    420
cggtgctaca gagttcttga agtggtggcc taactacggc tacactagaa ggacagtatt    480
tggtatctgc gctctgctga agccagttac cttcggaaaa agagttggta gctcttgatc    540
cggcaaacaa accaccgctg gtagcggtgg ttttttgtt tgcaagcagc agattacgcg     600
cagaaaaaaa ggatctcaag aagatccttt gatcttttct acggggtctg acgctcagtg    660
gaacgaaaac tcacgttaag gcctgcaggg ccgattttgg tcatgagatt atcaaaaagg    720
atcttcacct agatcctttt aaattaaaaa tgaagtttta atcaatcta aagtatatat     780
gagtaaactt ggtctgacag ttaccaatgc ttaatcagtg aggcacctat ctcagcgatc    840
tgtctatttc gttcatccat agttgcctga ctccccgtcg tgtagataac tacgatacgg    900
gagggcttac catctggccc cagtgctgca atgataccgc gagacccacg ctcaccggct    960
ccagatttat cagcaataaa ccagccagcc ggaagggccg agcgcagaag tggtcctgca   1020
actttatccg cctccatcca gtctattaat tgttgccggg aagctagagt aagtagttcg   1080
ccagttaata gtttgcgcaa cgttgttgcc attgctacag gcatcgtggt gtcacgctcg   1140
tcgtttggta tggcttcatt cagctccggt tcccaacgat caaggcgagt tacatgatcc   1200
cccatgttgt gcaaaaaagc ggttagctcc ttcggtcctc cgatcgttgt cagaagtaag   1260
ttggccgcag tgttatcact catggttatg gcagcactgc ataattctct tactgtcatg   1320
ccatccgtaa gatgcttttc tgtgactggt gagtactcaa ccaagtcatt ctgagaatag   1380
tgtatgcggc gaccgagttg ctcttgcccg gcgtcaatac gggataatac cgcgccacat   1440
agcagaactt taaaagtgct catcattgga aaacgttctt cggggcgaaa actctcaagg   1500
atcttaccgc tgttgagatc cagttcgatg taacccactc gtgcacccaa ctgatcttca   1560
gcatctttta ctttcaccag cgtttctggg tgagcaaaaa caggaaggca aaatgccgca   1620
aaaaagggaa taaggcgac acggaaatgt tgaatactca tactcttcct ttttcaatat   1680
tattgaagca tttatcaggg ttattgtctc atggccattt aggcctctag agttgtgaag   1740
tcggtaatcc cgctgtatag taatacgagt cgcatctaaa tactccgaag ctgctgcgaa   1800
cccggagaat cgagatgtgc tggaaagctt ctagcgagcg gctaaattag catgaaaggc   1860
tatgagaaat tctggagacg gcttgttgaa tcatggcgtt ccattcttcg acaagcaaag   1920
cgttccgtcg cagtagcagg cactcattcc gaaaaaaact cggagattcc taagtagcga   1980
tggaaccgga ataatataat aggcaataca ttgagttgcc tcgacggttg caatgcaggg   2040
gtactgagct tggacataac tgttccgtac cccacctctt ctcaaccttt ggcgtttccc   2100
tgattcagcg tacccgtaca agtcgtaatc actattaacc cagactgacc ggacgtgttt   2160
tgcccttcat ttggagaaat aatgtcattg cgatgtgtaa tttgcctgct tgaccgactg   2220
```

```
gggctgttcg aagcccgaat gtaggattgt tatccgaact ctgctcgtag aggcatgttg    2280
tgaatctgtg tcgggcagga cacgcctcga aggttcacgg caagggaaac caccgatagc    2340
agtgtctagt agcaacctgt aaagccgcaa tgcagcatca ctggaaaata caaaccaatg    2400
gctaaaagta cataagttaa tgcctaaaga agtcatatac cagcggctaa taattgtaca    2460
atcaagtggc taaacgtacc gtaatttgcc aacggcttgt ggggttgcag aagcaacggc    2520
aaagccccac ttccccacgt ttgtttcttc actcagtcca atctcagctg gtgatccccc    2580
aattgggtcg cttgtttgtt ccggtgaagt gaaagaagac agaggtaaga atgtctgact    2640
cggagcgttt tgcatacaac caagggcagt gatggaagca agtgaaatgt tgacattcaa    2700
ggagtattta gccagggatg cttgagtgta tcgtgtaagg aggtttgtct gccgatacga    2760
cgaatactgt atagtcactt ctgatgaagt ggtccatatt gaaatgtaaa gtcggcactg    2820
aacaggcaaa agattgagtt gaaactgcct aagatctcgg gccctcgggc cttcggcctt    2880
tgggtgtaca tgtttgtgct ccgggcaaat gcaaagtgtg gtaggatcga acacactgct    2940
gcctttacca agcagctgag ggtatgtgat aggcaaatgt tcaggggcca ctgcatggtt    3000
tcgaatagaa agagaagctt agccaagaac aatagccgat aaagatagcc tcattaaacg    3060
gaatgagcta gtaggcaaag tcagcgaatg tgtatatata aaggttcgag gtccgtgcct    3120
ccctcatgct ctccccatct actcatcaac tcagatcctc caggagactt gtacaccatc    3180
ttttgaggca cagaaaccca atagtcaacc atcacaagtt tgtacaaaaa agcaggctcc    3240
gcggccgccc ccttcaccaa gatgcagttc ttcgccgtcg ccctcttcgc caccagcgcc    3300
ctggctgctg tctgccctac cggcctcttc tccaaccctc tgtgctgtgc caccaacgtc    3360
ctcgacctca ttggcgttga ctgcaagacc cgtatgttga attccaatct ctgggcatcc    3420
tgacattgga cgatacagtt gacttacacg atgctttaca gctaccatcg ccgtcgacac    3480
tggcgccatc ttccaggctc actgtgccag caagggctcc aagcctcttt gctgcgttgc    3540
tcccgtggta agtagtgctc gcaatggcaa agaagtaaaa agacatttgg gcctgggatc    3600
gctaactctt gatatcaagg ccgaccaggc tctcctgtgc cagaaggcca tcggcacctt    3660
ctaaagcaat ggcttgcttt actgccggca gtctttgaga actaagggtg ggcgcgccga    3720
cccagctttc ttgtacaaag tggtgatcgc gccagctccg tgcgaaagcc tgacgcaccg    3780
gtagattctt ggtgagcccg tatcatgacg gcggcgggag ctacatggcc ccgggtgatt    3840 tattttttt gtatctactt ctgaccctt tcaaatatac ggtcaactca tctttcactg    3900
gagatgcggc ctgcttggta ttgcgatgtt gtcagcttgg caaattgtgg ctttcgaaaa    3960
cacaaaacga ttccttagta gccatgcatt ttaagataac ggaatagaag aaagaggaaa    4020
ttaaaaaaaa aaaaaaaaca aacatcccgt tcataacccg tagaatcgcc gctcttcgtg    4080
tatcccagta ccagtttatt ttgaatagct cgcccgctgg agagcatcct gaatgcaagt    4140
aacaaccgta gaggctgaca cggcaggtgt tgctagggag cgtcgtgttc tacaaggcca    4200
gacgtcttcg cggttgatat atatgtatgt ttgactgcag gctgctcagc gacgacagtc    4260
aagttcgccc tcgctgcttg tgcaataatc gcagtgggga agccacaccg tgactcccat    4320
ctttcagtaa agctctgttg gtgttttatca gcaatacacg taatttaaac tcgttagcat    4380
ggggctgata gcttaattac cgtttaccag tgccatggtt ctgcagcttt ccttggcccg    4440
taaaattcgg cgaagccagc caatcaccag ctaggcacca gctaaaccct ataattagtc    4500
tcttatcaac accatccgct cccccgggat caatgaggag aatgaggggg atgcggggct    4560
```

```
aaagaagcct acataacccct catgccaact cccagtttac actcgtcgag ccaacatcct    4620
gactataagc taacacagaa tgcctcaatc ctgggaagaa ctggccgctg ataagcgcgc    4680
ccgcctcgca aaaaccatcc ctgatgaatg gaaagtccag acgctgcctg cggaagacag    4740
cgttattgat tcccaaaga aatcggggat cctttcagag gccgaactga agatcacaga    4800
ggcctccgct gcagatcttg tgtccaagct ggcggccgga gagttgacct cggtggaagt    4860
tacgctagca ttctgtaaac gggcagcaat cgcccagcag ttagtagggt cccctctacc    4920
tctcagggag atgtaacaac gccaccttat gggactatca agctgacgct ggcttctgtg    4980
cagacaaact gcgcccacga gttcttccct gacgccgctc tcgcgcaggc aagggaactc    5040
gatgaatact acgcaaagca aagagaccc gttggtccac tccatggcct ccccatctct    5100
ctcaaagacc agcttcgagt caaggtacac cgttgcccct aagtcgttag atgtccctt    5160
ttgtcagcta acatatgcca ccagggctac gaaacatcaa tgggctacat ctcatggcta    5220
aacaagtacg acgaagggga ctcggttctg acaaccatgc tccgcaaagc cggtgccgtc    5280
ttctacgtca agacctctgt cccgcagacc ctgatggtct gcgagacagt caacaacatc    5340
atcgggcgca ccgtcaaccc acgcaacaag aactggtcgt gcggcggcag ttctggtggt    5400
gagggtgcga tcgttgggat tcgtggtggc gtcatcggtg taggaacgga tatcggtggc    5460
tcgattcgag tgccggccgc gttcaacttc ctgtacggtc taaggccgag tcatgggcgg    5520
ctgccgtatg caaagatggc gaacagcatg gagggtcagg agacggtgca cagcgttgtc    5580
gggccgatta cgcactctgt tgagggtgag tccttcgcct cttccttctt ttcctgctct    5640
ataccaggcc tccactgtcc tcctttcttg ctttttatac tatatacgag accggcagtc    5700
actgatgaag tatgttagac ctccgcctct tcaccaaatc cgtcctcggt caggagccat    5760
ggaaatacga ctccaaggtc atccccatgc cctggcgcca gtccgagtcg acattattg    5820
cctccaagat caagaacggc gggctcaata tcggctacta caacttcgac ggcaatgtcc    5880
ttccacaccc tcctatcctg cgcggcgtgg aaaccaccgt cgccgcactc gccaaagccg    5940
gtcacaccgt gaccccgtgg acgccataca agcacgattt cggccacgat ctcatctccc    6000
atatctacgc ggctgacggc agcgccgacg taatgcgcga tatcagtgca tccggcgagc    6060
cggcgattcc aaatatcaaa gacctactga acccgaacat caaagctgtt aacatgaacg    6120
agctctggga cacgcatctc cagaagtgga attaccagat ggagtacctt gagaaatggc    6180
gggaggctga agaaaaggcc gggaaggaac tggacgccat catcgcgccg attacgccta    6240
ccgctgcggt acgcatgac cagttccggt actatgggta tgcctctgtg atcaacctgc    6300
tggatttcac gagcgtggtt gttccggtta cctttgcgga taagaacatc gataagaaga    6360
atgagagttt caaggcggtt agtgagcttg atgccctcgt gcaggaagag tatgatccgg    6420
aggcgtacca tgggcaccg gttgcagtgc aggttatcgg acggagactc agtgaagaga    6480
ggacgttggc gattgcagag gaagtgggga agttgctggg aaatgtggtg actccatagc    6540
taataagtgt cagatagcaa tttgcacaag aaatcaatac cagcaactgt aaataagcgc    6600
tgaagtgacc atgccatgct acgaaagagc agaaaaaaac ctgccgtaga accgaagaga    6660
tatgacacgc ttccatctct caaaggaaga atcccttcag ggttgcgttt ccagt        6715
```

<210> SEQ ID NO 35
<211> LENGTH: 4600
<212> TYPE: DNA
<213> ORGANISM: Artificial Sequence
<220> FEATURE:
<223> OTHER INFORMATION: synthetic pTrex8R(Hfb2) plasmid

<400> SEQUENCE: 35

```
attaaggcca tttaggccgt tgctggcgtt tttccatagg ctccgccccc ctgacgagca     60
tcacaaaaat cgacgctcaa gtcagaggtg gcgaaacccg acaggactat aaagatacca    120
ggcgtttccc cctggaagct ccctcgtgcg ctctcctgtt ccgaccctgc cgcttaccgg    180
atacctgtcc gcctttctcc cttcgggaag cgtggcgctt tctcatagct cacgctgtag    240
gtatctcagt tcggtgtagg tcgttcgctc caagctgggc tgtgtgcacg aaccccccgt    300
tcagcccgac cgctgcgcct tatccggtaa ctatcgtctt gagtccaacc cggtaagaca    360
cgacttatcg ccactggcag cagccactgg taacaggatt agcagagcga ggtatgtagg    420
cggtgctaca gagttcttga agtggtggcc taactacggc tacactagaa ggacagtatt    480
tggtatctgc gctctgctga agccagttac cttcggaaaa agagttggta gctcttgatc    540
cggcaaacaa accaccgctg gtagcggtgg ttttttttgtt tgcaagcagc agattacgcg    600
cagaaaaaaa ggatctcaag aagatccttt gatcttttct acggggtctg acgctcagtg    660
gaacgaaaac tcacgttaag gcctgcaggg ccgattttgg tcatgagatt atcaaaaagg    720
atcttcacct agatcctttt aaattaaaaa tgaagtttta aatcaatcta agtatatat    780
gagtaaactt ggtctgacag ttaccaatgc ttaatcagtg aggcacctat ctcagcgatc    840
tgtctatttc gttcatccat agttgcctga ctccccgtcg tgtagataac tacgatacgg    900
gagggcttac catctggccc cagtgctgca atgataccgc gagacccacg ctcaccggct    960
ccagatttat cagcaataaa ccagccagcc ggaagggccg agcgcagaag tggtcctgca   1020
actttatccg cctccatcca gtctattaat tgttgccggg aagctagagt aagtagttcg   1080
ccagttaata gtttgcgcaa cgttgttgcc attgctacag gcatcgtggt gtcacgctcg   1140
tcgtttggta tggcttcatt cagctccggt tcccaacgat caaggcgagt tacatgatcc   1200
cccatgttgt gcaaaaaagc ggttagctcc ttcggtcctc cgatcgttgt cagaagtaag   1260
ttggccgcag tgttatcact catggttatg gcagcactgc ataattctct tactgtcatg   1320
ccatccgtaa gatgcttttc tgtgactggt gagtactcaa ccaagtcatt ctgagaatag   1380
tgtatgcggc gaccgagttg ctcttgcccg gcgtcaatac gggataatac cgcgccacat   1440
agcagaactt taaaagtgct catcattgga aaacgttctt cggggcgaaa actctcaagg   1500
atcttaccgc tgttgagatc cagttcgatg taacccactc gtgcacccaa ctgatcttca   1560
gcatctttta ctttcaccag cgtttctggg tgagcaaaaa caggaaggca aaatgccgca   1620
aaaaagggaa taagggcgac acggaaatgt tgaatactca tactcttcct ttttcaatat   1680
tattgaagca tttatcaggg ttattgtctc atggccattt aggcctctag agttgtgaag   1740
tcggtaatcc cgctgtatag taatacgagt cgcatctaaa tactccgaag ctgctgcgaa   1800
cccggagaat cgagatgtgc tggaaagctt ctagcgagcg gctaaattag catgaaaggc   1860
tatgagaaat tctggagacg gcttgttgaa tcatggcgtt ccattcttcg acaagcaaag   1920
cgttccgtcg cagtagcagg cactcattcc cgaaaaaact cggagattcc taagtagcga   1980
tggaaccgga ataatataat aggcaataca ttgagttgcc tcgacggttg caatgcaggg   2040
gtactgagct tggacataac tgttccgtac cccacctctt ctcaacctttt ggcgtttccc   2100
tgattcagcg tacccgtaca agtcgtaatc actattaacc cagactgacc ggacgtgttt   2160
tgcccttcat ttggagaaat aatgtcattg cgatgtgtaa tttgcctgct tgaccgactg   2220
gggctgttcg aagcccgaat gtaggattgt tatccgaact ctgctcgtag aggcatgttg   2280
```

```
tgaatctgtg tcgggcagga cacgcctcga aggttcacgg caagggaaac caccgatagc    2340
agtgtctagt agcaacctgt aaagccgcaa tgcagcatca ctggaaaata caaaccaatg    2400
gctaaaagta cataagttaa tgcctaaaga agtcatatac cagcggctaa taattgtaca    2460
atcaagtggc taaacgtacc gtaatttgcc aacggcttgt ggggttgcag aagcaacggc    2520
aaagccccac ttccccacgt tgtttcttc actcagtcca atctcagctg gtgatccccc     2580
aattgggtcg cttgtttgtt ccggtgaagt gaaagaagac agaggtaaga atgtctgact    2640
cggagcgttt tgcatacaac caagggcagt gatggaagac agtgaaatgt tgacattcaa    2700
ggagtattta gccagggatg cttgagtgta tcgtgtaagg aggtttgtct gccgatacga    2760
cgaatactgt atagtcactt ctgatgaagt ggtccatatt gaaatgtaaa gtcggcactg    2820
aacaggcaaa agattgagtt gaaactgcct aagatctcgg gccctcgggc cttcggcctt    2880
tgggtgtaca tgtttgtgct ccgggcaaat gcaaagtgtg gtaggatcga acacactgct    2940
gcctttacca agcagctgag ggtatgtgat aggcaaatgt tcaggggcca ctgcatggtt    3000
tcgaatagaa agagaagctt agccaagaac aatagccgat aaagatagcc tcattaaacg    3060
gaatgagcta gtaggcaaag tcagcgaatg tgtatatata aaggttcgag gtccgtgcct    3120
ccctcatgct ctccccatct actcatcaac tcagatcctc caggagactt gtacaccatc    3180
ttttgaggca cagaaaccca atagtcaacc atcacaagtt tgtacaaaaa agcaggctcc    3240
gcggccgccc ccttcaccaa gatgcagttc ttcgccgtcg ccctcttcgc caccagcgcc    3300
ctggctgctg tctgccctac cggcctcttc tccaaccctc tgtgctgtgc caccaacgtc    3360
ctcgacctca ttggcgttga ctgcaagacc cgtatgttga attccaatct ctgggcatcc    3420
tgacattgga cgatacagtt gacttacacg atgctttaca gctaccatcg ccgtcgacac    3480
tggcgccatc ttccaggctc actgtgccag caagggctcc aagcctcttt gctgcgttgc    3540
tcccgtggta agtagtgctc gcaatggcaa agaagtaaaa agacatttgg gcctgggatc    3600
gctaactctt gatatcaagg ccgaccaggc tctcctgtgc cagaaggcca tcggcacctt    3660
ctaaagcaat ggcttgcttt actgccggca gtctttgaga actaagggtg ggcgcgccga    3720
cccagctttc ttgtacaaag tggtgatcgc gccagctccg tgcgaaagcc tgacgcaccg    3780
gtagattctt ggtgagcccg tatcatgacg gcggcgggag ctacatggcc ccgggtgatt    3840
tatttttttt gtatctactt ctgacccttt tcaaatatac ggtcaactca tctttcactg    3900
gagatgcggc ctgcttggta ttgcgatgtt gtcagcttgg caaattgtgg ctttcgaaaa    3960
cacaaaacga ttccttagta gccatgcatt ttaagataac ggaatagaag aaagaggaaa    4020
ttaaaaaaaa aaaaaaaaca aacatcccgt tcataaccog tagaatcgcc gctcttcggc    4080
tagctagtta cgcttgttta tttacgacaa gatctagaag attcgagata gaataataat    4140
aataacaaca atttgcctct tctttccacc tttcagtct  tactctccct tctgacattg     4200
aacgcctcaa tcagtcagtc gccttgtact tggcacggta atcctccgtg ttcttgatat    4260
cctcaggggt agcaaagccc ttcatgccat cgataatgtc atccagagtg aggatggcaa    4320
agatggggat gccgtactcc ttcctcagct cgccaatggc actcggtcca ggcttggagt    4380
cgtcgccatc cgcagcgggg agcttctcca tgcggtccag ggccacgacg atgccggcga    4440
cgatgccgcc ctccttggtg atcttctcaa tggcgtccct cttggcggtg ccggcggtga    4500
tgacgtcgtc gacaatcagg accctcttgc ccttgagcga agcgccgacg atgttgccgc    4560
cctcgccgtg gtccttggcc tccttgcggt caaacgagta                          4600
```

THERMOSTABLE TRICHODERMA CELLULASE

INCORPORATION BY REFERENCE

This application is a divisional of U.S. patent application Ser. No. 13/276,467, filed Oct. 19, 2011, which claims priority to U.S. provisional application Ser. No. 61/394,946 filed Oct. 20, 2010 and European patent application No. 10188285.0 filed Oct. 20, 2010.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

SEQUENCE LISTING

The sequence listing submitted via EFS, in compliance with 37 C.F.R. §1.52(e), is incorporated herein by reference. The sequence listing text file submitted via EFS contains the file "31508-US-DIV_ST25.txt" created on Aug. 20, 2015, which is 40,960 bytes in size.

FIELD OF THE INVENTION

The invention relates to *Trichoderma*, e.g., *T. reesei*, host cells with a modification comprising or consisting essentially of a disruption or deletion as whereby expression of the thermostable fungal cellulase enzyme, e.g., endoglucanase V (EGV) is prevented or reduced, e.g., *Trichoderma*, e.g., *T. reesei*, host cells with a modification comprising or consisting essentially of one or more deletion or disruption in nucleotides involved in expression of EGV, e.g., disruption or deletion of the gene encoding or the coding region for or the promoter or regulatory elements for expression of this cellulase. Such host cells are particularly useful for expressing thermostable polypeptides free from unwanted cellulase activity. The invention advantageously relates to *Trichoderma*, e.g., *T. reesei*, that comprises and expresses an exogenous nucleic acid molecule encoding a protein of interest, e.g., a nucleic acid molecule encoding a hydrophobin, e.g., hydrophobin II, and with a modification that comprises or consists essentially of one or more deletion or disruption of nucleotide(s) involved in expression of EGV, whereby the protein of interest, e.g., hydrophobin, such as hydrophobin II, is expressed with EGV expression prevented or reduced. For example, the *Trichoderma* modification can consist essentially of deletion or disruption of egl5.

BACKGROUND OF THE INVENTION

Cellulose and hemicellulose are the most abundant plant materials produced by photosynthesis. They can be degraded and used as an energy source by numerous microorganisms (e.g., bacteria, yeast and fungi) that produce extracellular enzymes capable of hydrolysis of the polymeric substrates to monomeric sugars (Aro et al. (2001) *J. Biol. Chem.* 276:24309-14).

Cellulases are enzymes that hydrolyze cellulose (β-1,4-glucan or β-D-glucosidic linkages) resulting in the formation of glucose, cellobiose, cellooligosaccharides, and the like. Cellulases have been traditionally divided into three major classes: endoglucanases (EC 3.2.1.4) ("EG"), exoglucanases or cellobiohydrolases (EC 3.2.1.91; "CBH") and β-glucosidases (β-D-glucoside glucohydrolase; EC 3.2.1.21; "BG") (Knowles et al. (1987) *TIBTECH* 5:255-61; and Schulein (1988) *Methods Enzymol.* 160:234-43). Endoglucanases act mainly on the amorphous parts of the cellulose fibre to hydrolyze internal β-1,4-glucosidic bonds in regions of low crystallinity. Cellobiohydrolases hydrolyze cellobiose from the reducing or non-reducing end of cellulose and are able to degrade crystalline cellulose (Nevalainen and Penttila (1995) *Mycota* 303-319). The presence of a cellobiohydrolase (CBH) in a cellulase system is believed to be required for efficient solubilization of crystalline cellulose (Suurnakki et al. (2000) *Cellulose* 7:189-209). β-glucosidase acts to liberate D-glucose units from cellobiose, cellooligosaccharides, and other glucosides (Freer (1993) *J. Biol. Chem.* 268:9337-42). β-glucosidases have also been shown to catalyze the hydrolysis of alkyl and/or aryl beta-D-glucosides such as methy β-D-glucoside and p-nitrophenyl glucoside as well as glycosides containing only carbohydrate residues, such as cellobiose.

Cellulases are known to be produced by a large number of bacteria, yeast and fungi. Certain fungi produce complete cellulase systems that include exo-cellobiohydrolases or CBH-type cellulases, endoglucanases or EG-type cellulases and β-glucosidases or BG-type cellulases. Other fungi and bacteria express little or no CBH-type cellulases. *Trichoderma reesei* (also referred to as *Hypocrea jecorina*) expresses a large number of cellulases, including two CBHs, i.e., CBHI (Cel7a) and CBHII (Cel6a), at least eight EGs, i.e., EGI (Cel7b), EGII (Cel5a), EGIII (Cel12a), EGIV (Cel61a), EGV (Cel45a), EGVI (Cel74a), EGVII (Cel61b), and EGVIII (Cel5b), and at least five BGs, i.e., BG1 (Cel3a), BG2 (Cel1a), BG3 (Cel3b), BG4 (Cel3c) and BG5 (Cel1b). EGIV, EGVI, and EGVIII also have xyloglucanase activity.

In some cases, it is desirable to use whole cellulase broths obtained from *T. reesei* as a source of celluloses, e.g., for biomass conversion, textile processing, paper and pulp treatment, and the like. In other cases, *T. reesei* serves as an excellent host organism for the expression of engineered cellulases, cellulases from other organisms, or different enzymes or other proteins entirely (e.g., amylases, proteases, lipases, structural proteins, and the like). Particularly in these latter cases, it may be desirable to express proteins of interest in the absence of endogenous *T. reesei* cellulases. While this may be accomplished by deleting endogenous *T. reesei* cellulase genes, the large number of these genes makes such an approach time consuming and labor intensive.

Citation or identification of any document in this application is not an admission that such document is available as prior art to the present invention.

SUMMARY OF THE INVENTION

The invention provides compositions, e.g., modified cells, including such cells engineered to express a protein of interest, such as hydrophobin, e.g., hydrophobin II, and methods, relating to a thermostable cellulase enzyme found in *Trichoderma*, e.g., *T. reesei*.

In one aspect, the invention provides a *Trichoderma*, e.g., *T. reesei*, host cell comprising or consisting essentially of a modification to substantially reduce or prevent the production of a thermostable EGV polypeptide.

In a further aspect the invention provides a *Trichoderma*, e.g., *T. reesei*, host cell comprises or consists essentially of a modification to substantially reduce or prevent the production of a thermostable EGV polypeptide wherein the modification consists essentially of one or more deletion or disruption in nucleotide(s) involved in expression of EGV, e.g., disruption or deletion of the gene encoding or the coding region or the promoter or regulatory elements for expression of this cellulase.

In one of the embodiments, the *Trichoderma*, e.g., *T. reesei*, host cell comprises or consists essentially of a modification to substantially reduce or prevent the production of a thermostable EGV polypeptide wherein the modification comprises or consists essentially of deletion or disruption of egl5.

In some embodiments, the *Trichoderma*, e.g., *T. reesei*, host cell comprises or consists essentially of a disrupted egl5.

In some embodiments, the *Trichoderma*, e.g., *T. reesei*, host cell comprises or consists essentially of a deleted egl5.

In particular embodiments, egl5 is deleted by homologous recombination. It also can be disrupted by homologous recombination.

In some embodiments, the *Trichoderma*, e.g., *T. reesei*, host cell is produced by modifying a parental host cell comprising a functional egl5.

In some embodiments, the *Trichoderma*, e.g., *T. reesei*, host cell comprises or consists essentially of one or more endogenous functional genes or nucleic acid molecules encoding a thermolabile enzyme whereby the thermolabile enzyme is expressed; for example, the thermolabile enzyme can be a cellulase, a hemi-cellulase, or a protease, or any two or all three of these enzymes. In some embodiments, the *Trichoderma*, e.g., *T. reesei*, can express one or more additional proteins which can be a exo-cellobiohydrolase, an endoglucanase, or a β-glucosidase, or any two or all three of these proteins.

In some embodiments, the *Trichoderma*, e.g., *T. reesei*, host cell further comprises a functional gene of interest or nucleotides encoding and allowing for expression of a protein of interest.

In some embodiments, the gene of interest encodes or the protein of interest is a thermostable polypeptide; for example, a hydrophobin, such as hydrophobin II.

In another aspect, the invention provides a method for making a thermostable protein of interest in a *Trichoderma*, e.g., *T. reesei*, host cell, comprising: introducing a nucleic acid molecule encoding the thermostable protein of interest into a *Trichoderma*, e.g., *T. reesei*, host cell under conditions whereby the protein of interest is expressed in vivo, e.g., wherein the nucleic acid molecule of interest is operably linked to a promoter or regulatory elements for expression; and wherein the *Trichoderma*, e.g., *T. reesei*, host cell comprises or consists essentially of a modification to substantially reduce or prevent the production of a thermostable EGV polypeptide wherein the modification consists essentially one or more deletion or disruption in nucleotide(s) involved in expression of EGV, e.g., disruption or deletion of the gene encoding or the coding region or the promoter or regulatory elements for expression of this cellulase; for instance, wherein the modification comprises or consists essentially of deletion or disruption of egl5. The thermostable protein of interest can be a hydrophobin, e.g., hydrophobin II. The *Trichoderma*, e.g., *T. reesei*, can additionally comprise and one or more gene(s) encoding additional functional protein(s), or one or more nucleic acid molecule(s) encoding additional functional protein(s) under conditions whereby the one or more additional functional protein(s) are expressed in vivo, e.g., wherein the one or more nucleic acid molecule(s) are operably linked to promoter(s) and/or regulatory element(s) for expression. The method can further comprise subjecting the expression products of the cell, including the protein of interest and any expressed additional functional protein(s) in the expression products, to an elevated temperature sufficient to substantially inactivate the additional proteins; wherein the elevated temperature is insufficient to inactivate the thermostable protein of interest and would be insufficient to inactivate EGV cellulase; wherein the thermostable protein of interest is produced in active or functional form substantially in the absence of activity from the additional proteins.

In another aspect, the invention provides a method for making a thermostable protein of interest, e.g., a hydrophobin such as hydrophobin II, comprising: subjecting expression products obtained from the *Trichoderma*, e.g., *T. reesei*, host cells to an elevated temperature, wherein: the *Trichoderma*, e.g., *T. reesei*, host cell comprises or consists essentially of a modification to substantially reduce or prevent the production of a thermostable EGV polypeptide wherein the modification consists essentially one or more deletion or disruption in nucleotide(s) involved in expression of EGV, e.g., disruption or deletion of the gene encoding or the coding region or the promoter or regulatory elements for expression of this cellulase; for instance, wherein the modification comprises or consists essentially of deletion or disruption of egl5; and the *Trichoderma*, e.g., *T. reesei*, can additionally comprise and one or more gene(s) encoding additional functional protein(s), or one or more nucleic acid molecule(s) encoding additional functional protein(s) under conditions whereby the one or more additional functional protein(s) are expressed in vivo, e.g., wherein the one or more nucleic acid molecule(s) are operably linked to promoter(s) and/or regulatory element(s) for expression; wherein, the elevated temperature is sufficient to inactivate the one or more additional functional proteins, if present, but is insufficient to inactivate the thermostable protein of interest or EGV; thereby producing the thermostable of protein of interest in active or functional form in the absence of activity from the additional functional proteins The foregoing methods can additionally comprise incubating the modified *Trichoderma*, e.g., *T. reesei*, host cell in a medium suitable for producing the protein of interest and the additional functional protein(s), if present.

The foregoing methods can also comprise isolating the expression products (or protein mixture) from the modified *Trichoderma*, e.g., *T. reesei*, host cell prior to the step of subjecting the protein of interest and the additional functional protein(s), if present, to the elevated temperature.

In the case of any of the methods, in some embodiments, egl5 is disrupted in host cells that otherwise would naturally comprise egl5.

In the case of any of the methods, in some embodiments, egl5 is deleted in host cells that otherwise naturally comprise egl5.

Thus, in the case of any of the methods, in some embodiments, the disrupted or deleted egl5 is endogenous.

Thus, the methods can additionally comprise deleting or disrupting egl5 or otherwise modifying *Trichoderma*, e.g., *T. reesei*, to substantially reduce or prevent the production of a thermostable EGV polypeptide wherein the modification consists essentially one or more deletion or disruption in nucleotide(s) involved in expression of EGV, e.g., disruption or deletion of the gene encoding or the coding region or the promoter or regulatory elements for expression of this cellulase.

In the case of any of the methods, in some embodiments, egl5 is deleted by homologous recombination. It also can be disrupted by homologous recombination.

In the case of any of the methods, in some embodiments, the one or more additional proteins are thermolabile proteins. In some embodiments, the one or more additional proteins can be a cellulase, a hemi-cellulase, or a protease, or any two or all three of these enzymes. In some embodiments, the one or more additional proteins can be a exo-cellobiohydrolase, an endoglucanase, or a β-glucosidase, or any two or all three of these proteins.

In the case of any of the methods, in some embodiments, the protein of interest is thermostable by virtue of being reversibly heat-denaturable.

In the case of any of the methods, in particular embodiments, the protein of interest is a hydrophobin, e.g., hydrophobin II.

In the case of any of the methods, in some embodiments, the elevated temperature is a temperature of 90° C. or more. In an advantageous embodiment, the elevated temperature may be less than about 100° C.

In the case of any of the methods, in some embodiments, exposure to the elevated temperature is for a time of 5 minutes or more.

In the case of any of the methods, in some embodiments, exposure to the elevated temperature is for a time of 60 minutes or more.

In yet a further aspect, a thermostable or reversibly heat-denaturable protein produced by any of these methods is provided.

In a related aspect, the invention provides a fermentation broth composition obtained from filamentous fungus host cells, for example, *Trichoderma*, e.g., *T. reesei* and comprising a hydrophobin, e.g., hydrophobin II, wherein the fermentation broth is substantially free of cellulase and/or mannanase activity. For example, a fermentation broth substantially free of cellulase and/or mannanase activity obtained or obtainable from any of the foregoing methods. Thus, in some embodiments, the hydrophobin, e.g., hydrophobin II, is produced in the presence of thermolabile cellulase and/or mannanase, and subjected to an elevated temperature to inactivate the cellulase and/or mannanase polypeptides.

In some embodiments, the hydrophobin, e.g., hydrophobin II, is produced in host cells such as *Trichoderma*, e.g., *T. reesei*, comprising or consisting essentially of a modification to substantially reduce or prevent the production of cellulase and/or mannanase wherein the modification consists essentially of one or more deletion or disruption in nucleotide(s) involved in expression of cellulase and/or mannanase, e.g., disruption or deletion of the gene encoding or the coding region or the promoter or regulatory elements for expression of cellulase and/or mannanase, whereby fermentation broth from producing (and containing) the hydrophobin is substantially free of cellulase and/or mannanase activity.

In some embodiments, the hydrophobin, e.g., hydrophobin II is produced in host cells such as *Trichoderma*, e.g., *T. reesei*, comprising or consisting essentially of a modification whereby the host cells lack gene(s) or nucleic acid molecule(s) encoding cellulase and/or mannanase, whereby fermentation broth from producing (and containing) the hydrophobin is substantially free of cellulase and/or mannanase activity.

In the fermentation broth embodiments, the fermentation broth may be concentrated and may further comprise any number of host cell proteins other than a cellulase and/or mannanase.

In any of the embodiments of the present invention, the polypeptide of interest may be thermostable, heat sensitive or thermolabile.

The present invention method also relates to controlling activity of the polypeptide of interest expressed by the modified *Trichoderma* host cells of the present invention, wherein the polypeptide of interest is heat sensitive or thermolabile, wherein said method may comprise subjecting the heat sensitive or thermolabile polypeptide of interest and the endogenous polypeptide to an elevated temperature, wherein the elevated temperature may be sufficient to inactivate the endogenous polypeptide and the heat sensitive or thermolabile polypeptide. In an advantageous embodiment, the endogenous polypeptide may be a cellulose. The method may further comprise, prior to subjecting the heat sensitive or thermolabile polypeptide of interest to the elevated temperature, contacting the polypeptide of interest with a compound upon which the polypeptide of interest acts. The method may further comprise, prior to subjecting the heat sensitive or thermolabile polypeptide of interest to the elevated temperature, contacting the polypeptide of interest with one or more compounds upon which the cellulose and the polypeptide of interest act.

The present invention method also relates to a method for controlling activity of the polypeptide of interest in the fermentation broth of the present invention, wherein the polypeptide of interest may be heat sensitive or thermolabile, wherein the method may comprise subjecting the fermentation broth to an elevated temperature sufficient to inactivate the endogenous polypeptide and the heat-sensitive or thermolabile polypeptide. In an advantageous embodiment, the endogenous polypeptide may be a cellulose. The method may further comprise, prior to subjecting the fermentation broth to the elevated temperature, contacting the fermentation broth with a compound of interest upon which the polypeptide of interest acts. The method may further comprise, prior to subjecting the fermentation broth to the elevated temperature, contacting the fermentation broth with one or more compounds upon which the cellulase and the polypeptide of interest act.

The present invention also relates to a method for controlling the activity of a cellulase present in a composition obtained from the modified *Trichoderma* host cells, wherein the composition may comprise at least one cellulase enzyme other than EGV, and the method may comprise subjecting the composition to an elevated temperature sufficient to inactivate the polypeptide of interest, and wherein following subjecting the composition to an elevated temperature the composition is substantially free of cellulase activity. The polypeptide of interest may be heat sensitive or thermolabile. In another embodiment, the polypeptide may be heat tolerant or thermostable. The subjecting the composition to an elevated temperature may be performed in a foodstuff or beverage. In another embodiment, the elevated temperature may be less than about 100 degrees C. In another embodiment, the composition obtained from the modified *Trichoderma* host cells may be a hydrophobin-comprising fermentation broth.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 USC §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

The terms "consists essentially of" and "consisting essentially of" are to particularly avoid the claims from reading on embodiments disclosed or suggested by the prior art, alone or in any combination, as it has been unexpectedly found that deletion or disruption in nucleotides involved in expression of EGV, e.g., disruption or deletion of the gene encoding or the coding region for this cellulose, such as deletion or disruption as to egl5, aids in expression of and/or obtaining a thermostable exogenous polypeptide, e.g., hydrophobin, such as hydrophobin II.

These and other embodiments are disclosed or are obvious from and encompassed by, the following Detailed Description, including the accompanying Figures.

BRIEF DESCRIPTION OF THE DRAWINGS

The following Detailed Description, given by way of example, but not intended to limit the invention solely to the specific embodiments described, may best be understood in conjunction with the accompanying drawings, in which:

FIG. 7 is the nucleotide sequence of a 3.5 kb DNA fragment carrying a fragment of the sucA gene fused with the hexokinase promoter (SEQ ID NO: 1).

FIG. 8 is the nucleotide sequence of pF1X, a small plasmid comprising an origin of replication and an ampicillin resistance gene from pUC19 and a bacteriophage fl origin of replication (SEQ ID NO: 2).

FIG. 9A and FIG. 9B are the deduced nucleotide sequence of the disrupted gene (i.e., "disruption cassette"), based on the known chromosomal DNA sequences of egl5 and pyr2 genes (SEQ ID NO: 3).

FIG. 10 is the nucleotide sequence of egl5 (SEQ ID NO: 32).

FIG. 11 is the amino acid sequence of EGV (SEQ ID NO: 33).

FIG. 13A is the nucleotide sequence of pTrex3gM(Hfb2).

FIG. 13B is the nucleotide sequence of pTrex8R(Hfb2).

DETAILED DESCRIPTION

Figure 1:
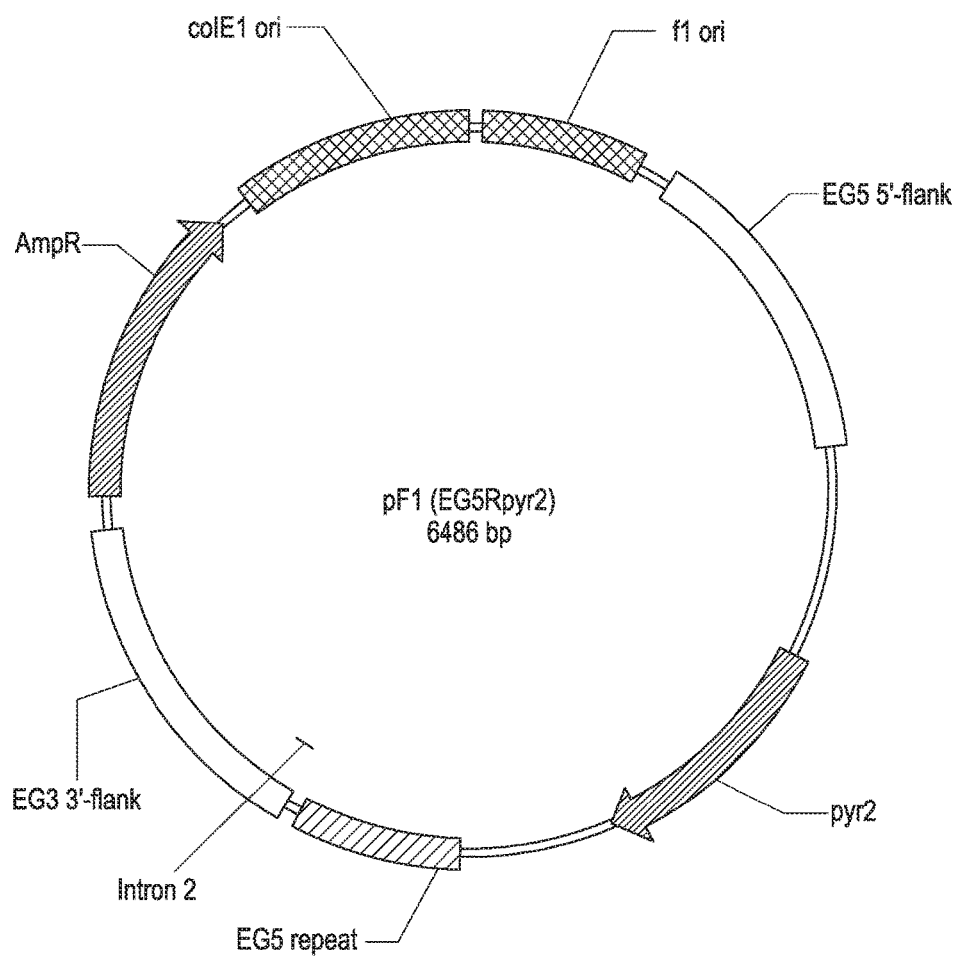
FIG. 1 is a plasmid map of pFl(EG5RPyr).

Prior to describing the present compositions and methods in detail, the following terms are defined for clarity. Terms not defined should be accorded their ordinary meanings as used in the relevant art.

As used herein, a "cellulase" is an enzymes that hydrolyzes β-1,4-glucan or β-D-glucosidic linkages, resulting in, e.g., the formation of glucose, cellobiose, cellooligosaccharides, and the like from cellulose. Cellulases include, e.g., endoglucanases, exoglucanases, β-glucosidases, and the like.

As used herein, an "endoglucanases (EG)" is a cellulase that acts mainly on the amorphous parts of the cellulose fibre to hydrolyze internal β-1,4-glucosidic bonds in regions of low crystallinity.

As used herein, the terms "hemicellulase" and "xylanase" are used interchangeably to refer generally to enzymes capable of hydrolyzing glycosidic bonds in polysaccharides comprising 5-carbon sugars. Such enzymes include, e.g., mannanases, arabinanases, glucuronidases, acetylxylan esterases, arabinofuranosidases, xylosidases, and the like.

As used herein, "*Trichoderma reesei*" (or *T. reesei*) refers to a filamentous fungus of the phylum Ascomycota. This organism was previously known as *Hypocrea jecorina*.

As used herein, the phrase "*T. reesei* EGV cellulase" refers to a polypeptide having the amino acid sequence of SEQ ID NO: 33 or a related polypeptide. A related polypeptide has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99%, or more, amino acid sequence identity with SEQ ID NO: 33, has endoglucanase activity on a cellulose substrate, and is thermostable using the assays described, herein. "EGV" may be referred to, herein, as "EG5."

As used herein, the phrase "*T. reesei* egl5 gene" or "egl5" refers to a nucleic acid that encodes EGV cellulase, or a related polypeptide, as described herein. The nucleotide sequence of an exemplary egl5 is shown as SEQ ID NO: 32. An amino acid sequence for EGV is shown in SEQ ID NO: 33.

As used herein, the term "thermostable," with respect to a polypeptide, refers to the ability of a polypeptide to retain biological activity after being subjected to a preselected elevated temperature for a preselected period of time. The biological activity may be an enymatic activity, a binding activity, a surface active property, or any other activity or property characteristic of the polypeptide. A polypeptide is considered thermostable if is maintains at least one-half of its original activity following exposure to the preselected elevated temperature for the preselected period of time. In broad terms, the preselected temperature and time are those required to substantially inactivate *T. reesei* cellulases other than EGV. These conditions can readily be established by assaying for cellulase activity in a *T. reesei* host cell comprising or consisting essentially of an egl5 deletion.

In some case, a protein is considered to be thermostable if it retains at least one-half (i.e., at least 50%) of its biological activity following exposure to a temperature of at least about 70° C., at least about 75° C., at least about 80°

C., at least about 85° C., at least about 90° C., or even at least about 95° C., for a time of at least about 3 minutes, at least about 5 minutes, at least about 10 minutes, at least about 15 minutes, at least about 20 minutes, at least about 30 minutes, at least about 45 minutes, or even at least about 60 minutes. In one example, the preselected temperature is about 90° C. or greater and the preselected time is about 5 minutes or greater. In another example, the preselected temperature is about 90° C. or greater and the preselected time is about 60 minutes or greater. Thermostable polypeptides include polypeptides that are reversibly denatured at an elevated temperatures, such that at least one-half (i.e., at least 50%) of their biological activity is restored following exposure as described.

As used herein, the terms "heat-labile," "non-thermostable," and "thermolabile," with respect to a polypeptide, are used interchangeably to refer to the inability of a polypeptide to retain biological activity after being subjected to a preselected elevated temperature for a preselected period of time. The biological activity may be an enymatic activity, a binding activity, a surface-active property, or any other activity or property characteristic of the polypeptide. A polypeptide is considered heat-labile if is loses at least 90%, at least 95%, at least 97%, at least 99%, or even essentially 100% of its original activity following exposure to the preselected elevated temperature for the preselected period of time. Such temperatures and times are described immediately above, and elsewhere in the present description. No restrictions are placed on the number or types of heat-labile polypeptides. Examples include but are not limited to cellulases, hemicellulases, proteases, lipases, amylases, esterases, perhydrolases, phytases, laccases, and other commercially-relevant enzymes, binding proteins, and structural proteins.

As used herein, the phrase "protein of interest" refers to a polypeptide, other than EGV, that is desired to be expressed in "*T. reesei*. Such a protein may be an enzyme, a binding protein, a surface-active protein, a structural protein, or the like. A protein of interest may be thermostable or thermolabile. Where specified, it is thermostable.

As used herein, the phrase "substantially free of an activity" (or similar phrases) means that a specified activity is either undetectable in an admixture of polypeptides, or present in an amount that would not interfere with the intended purpose of the admixture.

As used herein, the terms "polypeptide" and "protein" are used interchangeably to refer to polymers of any length comprising amino acid residues linked by peptide bonds. The conventional one-letter or three-letter code for amino acid residues is used herein. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, functionally and/or structurally similar proteins are considered to be "related proteins." Such proteins may be derived from organisms of different genera and/or species, or even different classes of organisms (e.g., bacteria and fungus). Related proteins also encompass homologs determined by primary sequence analysis, determined by secondary or tertiary structure analysis, or determined by immunological cross-reactivity.

As used herein, the term "derivative polypeptide/protein" refers to a protein which is derived from a protein by addition of one or more amino acids to either or both the N- and C-terminal end(s), substitution of one or more amino acids at one or a number of different sites in the amino acid sequence, deletion of one or more amino acids at either or both ends of the protein or at one or more sites in the amino acid sequence, and/or insertion of one or more amino acids at one or more sites in the amino acid sequence. The preparation of a protein derivative may be achieved by modifying a DNA sequence which encodes for the native protein, transformation of that DNA sequence into a suitable host, and expression of the modified DNA sequence to form the derivative protein.

Related (and derivative) proteins include "variant proteins." Variant proteins differ from a reference/parent protein, e.g., a wild-type protein, by substitutions, deletions, and/or insertions at small number of amino acid residues. The number of differing amino acid residues may be one or more, for example, 1, 2, 3, 4, 5, 6, 7, 8, 9, 10, 15, 20, 30, 40, 50, or more amino acid residues. Variant proteins share at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99%, or more, amino acid sequence identity with a reference protein. A variant protein may also differ from a reference protein in selected motifs, domains, epitopes, conserved regions, and the like.

As used herein, the term "analogous sequence" refers to a sequence within a protein that provides similar function, tertiary structure, and/or conserved residues as the protein of interest (i.e., typically the original protein of interest). For example, in epitope regions that contain an alpha-helix or a beta-sheet structure, the replacement amino acids in the analogous sequence preferably maintain the same specific structure. The term also refers to nucleotide sequences, as well as amino acid sequences. In some embodiments, analogous sequences are developed such that the replacement amino acids result in a variant enzyme showing a similar or improved function. In some embodiments, the tertiary structure and/or conserved residues of the amino acids in the protein of interest are located at or near the segment or fragment of interest. Thus, where the segment or fragment of interest contains, for example, an alpha-helix or a beta-sheet structure, the replacement amino acids preferably maintain that specific structure.

As used herein, the term "homologous protein" refers to a protein that has similar activity and/or structure to a reference protein. It is not intended that homologs necessarily be evolutionarily related. Thus, it is intended that the term encompass the same, similar, or corresponding enzyme(s) (i.e., in terms of structure and function) obtained from different organisms. In some embodiments, it is desirable to identify a homolog that has a quaternary, tertiary and/or primary structure similar to the reference protein. In some embodiments, homologous proteins induce similar immunological response(s) as a reference protein. In some embodiments, homologous proteins are engineered to produce enzymes with desired activity(ies).

The degree of homology between sequences may be determined using any suitable method known in the art (see, e.g., Smith and Waterman (1981) *Adv. Appl. Math.* 2:482; Needleman and Wunsch (1970) *J. Mol. Biol.*, 48:443; Pearson and Lipman (1988) *Proc. Natl. Acad. Sci. USA* 85:2444;

programs such as GAP, BESTFIT, FASTA, and TFASTA in the Wisconsin Genetics Software Package (Genetics Computer Group, Madison, Wis.); and Devereux et al. (1984) *Nucleic Acids Res.* 12:387-395).

For example, PILEUP is a useful program to determine sequence homology levels. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Dooittle, (Feng and Doolittle (1987) *J. Mol. Evol.* 35:351-360). The method is similar to that described by Higgins and Sharp (Higgins and Sharp (1989) *CABIOS* 5:151-153). Useful PILEUP parameters including a default gap weight of 3.00, a default gap length weight of 0.10, and weighted end gaps. Another example of a useful algorithm is the BLAST algorithm, described by Altschul et al. (Altschul et al. (1990) *J. Mol. Biol.* 215:403-410; and Karlin et al. (1993) *Proc. Natl. Acad. Sci. USA* 90:5873-5787). One particularly useful BLAST program is the WU-BLAST-2 program (See, Altschul et al. (1996) *Meth. Enzymol.* 266:460-480). Parameters "W," "T," and "X" determine the sensitivity and speed of the alignment. The BLAST program uses as defaults a word-length (W) of 11, the BLOSUM62 scoring matrix (See, Henikoff and Henikoff (1989) *Proc. Natl. Acad. Sci. USA* 89:10915) alignments (B) of 50, expectation (E) of 10, M'5, N'-4, and a comparison of both strands.

As used herein, the phrases "substantially similar" and "substantially identical," in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (i.e., wild-type) sequence. Sequence identity may be determined using known programs such as BLAST, ALIGN, and CLUSTAL using standard parameters. (See, e.g., Altschul, et al. (1990) *J. Mol. Biol.* 215:403-410; Henikoff et al. (1989) *Proc. Natl. Acad. Sci. USA* 89:10915; Karin et al. (1993) *Proc. Natl. Acad. Sci USA* 90:5873; and Higgins et al. (1988) *Gene* 73:237-244). Software for performing BLAST analyses is publicly available through the National Center for Biotechnology Information. Also, databases may be searched using FASTA (Pearson et al. (1988) *Proc. Natl. Acad. Sci. USA* 85:2444-2448). One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, "wild-type" and "native" genes or proteins are those found in nature. The terms "wild-type sequence," and "wild-type gene/protein" are used interchangeably herein, to refer to a sequence that is native or naturally occurring in a host cell.

As used herein, "deletion of a gene," refers to its removal from the genome of a host cell.

As used herein, "disruption of a gene" refers broadly to any genetic or chemical manipulation that substantially prevents expression of a function gene product, e.g., a protein, in a host cell. Exemplary methods of disruption include complete or partial deletion of any portion of a gene (including a polypeptide-coding sequence, a promoter, an enhancer, or another regulatory element, or mutagenesis of the same (including substitutions, insertions, deletions, and combinations, thereof), to substantially prevent expression of a function gene product.

As used herein, "a functional gene" is a gene capable of being used by cellular components to produce an active gene product, typically a protein. "Functional" genes are the antithesis of "disrupted" genes, which are modified such that they cannot be used by cellular components to produce an active gene product. Exemplary functional genes include but are not limited to cellulases other than EGV, hemi-cellulases, proteases, amylases, lipases, perhydrolases, esterases, pectate lyases, pectinases, laccases, oxidases, reductases, amidases, and other enzymes, structural proteins, surface active proteins, binding proteins, and the like.

As used herein, *T. reesei* host cells have been "modified to prevent the production of a thermostable EGV cellulase" if they have been genetically or chemically altered to prevent the production of an EGV polypeptide that exibits thermostable cellulase activity, e.g., as determined using the assays described, herein. Such modifications include, but are not limited to, deletion of the egl5, disruption of the egl5, modification of the egl5 such that the encoded EGV polypeptide is no longer thermostable, modification to the egl5 such that the encoded EGV polypeptide no longer exibits cellulase activity, modification of the egl5 such that the encoded EGV polypeptide is no longer secreted, modifications of promoter or regulatory elements such that EGV is not expressed, and combinations, thereof.

As used herein, a "functional polypeptide/protein" is a protein that posses an activity, such as an enzymatic activity, a binding activity, a surface-active property, or the like, and which has not been mutagenized, truncated, or otherwise modified to abolish (or essentially eliminate) the activity. Functional polypeptides may be themostable or thermolabile, as specified.

As used, herein, an "unwanted activity" is an activity (e.g., an enzymatic activity, a binding activity, a surface-active property, or the like), which is not desired in a protein preparation produced from *T. reesei* host cells. Unwanted activities typically occur in protein preparations that further comprise a protein of interest having a desired or desirable activity.

As used herein, a "fermentation broth composition" refers to cell growth medium that contains a protein of interest, such as hydrophobin. The cell growth medium may include cells and/or cell debris, and may be concentrated. An exemplary fermentation broth composition is hydrophobin-containing, ultrafiltration-concentrated fermentation broth.

As used herein, a "mannanase mannose unit (MMU)" is the amount of mannanase per mg of hydrophobin required to produce 1 µmol of reducing end equivalents (including but not limited to D-Mannose) per minute at pH 7.0 and at 50° C. in the presence of 0.24% locust bean gum (LBG).

As used herein, an "endoglucanase unit (EGU)" is the amount of endogluconase per mg of hydrophobin required to produce 1 µmol of reducing sugars per minute.

As used herein, a "protease unit (PU)" corresponds to the amount of cysteine protease per mg of hydrophobin required to hydrolyse 1 µmol N-benzoyl-L-arginine ethyl ester (BAEE) per minute at pH 6.2 and 25° C.

As used herein, "treating" a food or other material to affect a change in the material means contacting the food or other material with a protein preparation produced from *T. reesei* host cells, wherein one or more proteins present in the protein preparation acts on a component of the food or other material to bring about a chemical change as the result of, e.g., an enzymatic activity, a binding activity, a surface-active property, or the like. Examples of treatment include contacting a baked food product with an amylase to hydrolyze amylopectin, contacting a food product with a lipase to generate emulsifiers, and contacting a food product with hydrophobin to alter the texture.

As used herein, the singular articles "a," "an," and "the" encompass the plural referents unless the context clearly dictates otherwise. All references cited herein are hereby incorporated by reference in their entirety.

The following abbreviations/acronyms have the following meanings unless otherwise specified:

EC enzyme commission
kDa kiloDalton
kb kilobase
MW molecular weight
w/v weight/volume
w/w weight/weight
v/v volume/volume
wt % weight percent
° C. degrees Centigrade
$H_2O$ water
$H_2O_2$ hydrogen peroxide
$dH_2O$ or DI deionized water
$dIH_2O$ deionized water, Milli-Q filtration
g or gm gram
µg microgram
mg milligram
kg kilogram
lb pound
µL and µl microliter
mL and ml milliliter
mm millimeter
nm nanometer
µm micrometer
M molar
mM millimolar
µM micromolar
µmol micromole
U unit
ppm parts per million
sec and " second
min and ' minute
hr hour
EtOH ethanol
eq. equivalent
N normal
PCR polymerase chain reaction
DNA deoxyribonucleic acid
FOA fluoroorotic acid
UV ultraviolet
$A_{540}$ absorbance measured at a wavelength of 540 nm
CMC carboxymethyl cellulose
rpm revolutions per minute
Δ relating to a deletion
MMU mannanase mannose unit
EGU endoglucanase unit
PU protease unit
4MUC 4-methylumbelliferyl β-D-cellobioside
4MUM 4-methylumbelliferyl β-D-mannopyranoside
NPC/mL µmole o-nitrophenol liberated/min/mL
MU/L µmole o-nitrophenol liberated/min/mL The present compositions and methods are based, in part, on the discovery that the *Trichoderma reesei* egl5 gene encodes a thermostable cellulase enzyme, i.e., EGV. In contrast, other known cellulases expressed by *T. reesei* are heat labile. The discovery that the product of egl5 is thermostable has far-reaching implication for the production of both endogenous and exogenous polypeptides in by *T. reesei*, in the absence of unwanted enzymatic activities, including cellulase activity.

Mention is made of PCT WO 2005/093073 ("the 073 PCT"). The 073 PCT pertains to *T. reesei* that express exogenous fusion proteins. Mention is also made WO 2005/001036 ("the 036 PCT"). The 036 PCT relates to the identification and isolation of certain genes in *T. reesei*. Mention is further made of WO 98/15619 ("the 619 PCT"). The 619 PCT concerns the expression of EGVI by *Trichoderma longibrachiatum*. None of the 073 PCT, the 036 PCT and the 619 PCT, either individually or in any combination, teaches or suggests preventing or reducing the expression in *Trichoderma*, such as *T. reesei*, of endogenous thermostable cellulases such as EGV, and especially does not teach or suggest preventing or reducing the expression in *Trichoderma*, such as *T. reesei*, of endogenous thermostable cellulases such as EGV and the expression by the *Trichoderma*, e.g., *T. reesei* of an exogenous thermostable polypeptide, such as a hydrophobin, e.g., hydrophobin II.

In one aspect, a method for expressing a thermostable polypeptide in *Trichoderma*, e.g., *T. reesei*, is provided, comprising or consisting essentially of the steps of disrupting egl5 in *T. reesei* host cells, expressing a thermostable polypeptide in the *Trichoderma* host cells, and exposing the resulting whole-cell lysate, cell broth, or partially-purified protein preparation to an elevated temperature, thereby eliminating substantially all heat-labile enzymatic activities from the protein preparation. In some embodiments, the heat-labile enzymatic activities are cellulase activities. One significant advantage of this method is that egl5 can be disrupted in the *Trichoderma* host cells used to express the thermostable protein of interest, while other genes encoding heat-labile enzymes can be left intact, avoiding the need to make multiple deletions in *Trichoderma* host cells. Exemplary heat-labile enzymes are proteases, cellulases, and xylanases.

In a related aspect, a *Trichoderma*, e.g., *T. reesei*, host cell having or consisting essentially of a disrupted egl5 is provided, the host cell being suitable for expressing heat stable polypeptides free of unwanted enzymatic activity. As above, *Trichoderma* genes that encode heat-labile enzymes can be left intact in the host cell, since the expression product of these genes can be inactivated by heat. In this manner, the *Trichoderma* host cell may include any number of intact genes encoding heat labile cellulases, so long as egl5 is disrupted.

In a further related aspect, a *Trichoderma*, e.g., *T. reesei*, host cell having or consisting essentially of a disrupted egl5 is provided, the host cell being suitable for expressing heat-labile polypeptides, wherein essentially all enzymatic activity can be inactivated by heat at a preselected time following expression. As before, the *Trichoderma* host cell may include any number of intact genes encoding heat labile enzymes, so long as the egl5 is disrupted.

In another aspect, the *Trichoderma* host cell modified to substantially reduce or prevent the production of a thermostable endoglucananse V (EGV) polypeptide wherein the modification comprises or consists essentially of disrupting or deleting a gene encoding EGV from the *Trichoderma* host cell wherein the gene encoding EGV is egl5 is provided.

In a related aspect, a composition comprising a hydrophobin polypeptide in the presence of reduced amounts, or substantially in the absence of, cellulase and/or mannanase activity is provided.

In some embodiments, the hydrophobin polypeptide is obtained from filamentous fungus host cells. Such hydrophobin compositions are well suited for use in applications where cellulose and mannose are present, and the enzymatic hydrolysis of these complex sugars is undesirable. In some cases, the hydrophobin polypeptide is produced in the presence of thermolabile cellulase and/or mannanase polypeptides, and subjected to an elevated temperature to inactivate the cellulase and/or mannanase polypeptides.

In some cases, the hydrophobin polypeptide is produced in host cells having or consisting essentially of disrupted genes encoding cellulase and/or mannanase polypeptides, such that active cellulase and/or mannanase polypeptides are not produced in the host cells.

In yet other cases, the hydrophobin polypeptide is produced in host cells lacking gene(s) or nucleic acid molecule(s) encoding cellulase and/or mannanase polypeptides.

The egl5 gene referred to herein corresponds to Genbank Accession No. Z33381 (Saloheimo, A. et al. (1994) *Mol. Microbiol.* 13:219-28). The nucleotide sequence of egl5 is set forth in FIG. 10 and is designated as SEQ ID N: 32:

The corresponding amino acid sequence of the EGV polypeptide is set forth in FIG. 10 and is designated as SEQ ID NO: 33:

EGV is an endo-1,4-beta-glucanase that belongs to the Carbohydrate Active Enzymes (CAZy) Family 45 glycosyl hydrolases and has the Enzyme Classification (EC) number (EC 3.2.1.4). These enzymes were formerly known as Family K cellulases/xylanases. An important feature of EGV, which distinguishes the enzyme from other known *T. reesei* cellulases, is that EGV is thermostable.

EGV polypeptides according to the present compositions and methods are cellulases that have a similar structure and function compared to the EGV cellulase having the amino acid sequence of SEQ ID NO: 33. Similar structure means at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99%, or more, primary amino acid sequence identity with SEQ ID NO: 33. Similar function means thermostable endo-1,4-beta-glucanase activity. In this context, themostability refers to the ability of the cellulase to retain at least one-half (i.e., at least 50%) of its original activity following exposure to a temperature of about 90° C. or greater for a time of about 5 minutes or longer.

One aspect of the compositions and methods is a host cell comprising a deletion or disruption of egl5, which precludes the expression of a functional enzyme.

Another aspect of the compositions and methods is a host cell comprising or consisting essentially of a deletion or disruption of egl5, which precludes the expression of a functional enzyme. Deletion refers to the removal of egl5 from the genome of the host cell, which can be accomplished by, e.g., homologous recombination or chemical mutagenesis. Homologous recombination is generally preferred since it is a targeted method. Disruption of egl5 refers broadly to any genetic or chemical manipulation of *T. reesei* host cells that substantially prevents expression of enzymatically active EGV cellulase. Exemplary methods of disruption include complete deletion of egl5, deletion of a portion of the genome that includes egl5, partial deletion (including truncation) of egl5, complete or partial deletion of the egl5 promoter, enhancer, or other genetic control elements, mutagenesis of the egl5 coding sequence, promoter, enhancer, or other genetic control elements, or any other genetic modification that precludes the expression of a functional egl5 gene product (i.e., EGV). Such disruptions may also be accomplished by, e.g., homologous recombination or chemical mutagenesis. For the purposes of the present compositions and methods, disruption of the egl5 gene also includes genetic modifications that abolish or reduce the thermostability of the EGV polypeptide.

In the process of deleting or disrupting egl5, any number of selectable markers may be introduced into a host cells to enable the selection of mutated host cells on solid or liquid media, to allow selection by cells sorting (e.g., FACS analyis), or to facilitate screening by PCR or Southern blot analysis. Additional host cell genes may also be deleted or disrupted. In some cases, it may be desirable to introduce a gene of interest at the site of deletion or disruption of egl5. In this manner, the present compositions and methods contemplate using the egl as a site for homologous recombination for introducing a nucleic acid sequence encoding a thermostable polypeptide into *T. reesei* host cells.

Genes of interest encode proteins of interest, which are desirable to express in *Trichoderma* in the absence of cellulase activity. In some cases, genes of interest encode thermostable polypeptides. Such thermostable polypeptides may be expressed in the absence of cellyulase activity by expressing them in a host cell in which egl5 has been deleted or disrupted, subjecting a host cell lysate or medium from these host cells to thermal stress to heat-inactivate cellulases expressed by the host cell, and recovering the thermostable polypeptide substantially free of cellulase activity.

Thermostable polypeptides include enzymes, structural proteins, nucleic acid binding proteins, receptors, and the like. Such proteins may be from thermophilic organisms, including but not limited to, *Pyrococcus furiosus, Thermus aquaticus, Thermus thermophilus, Thermus thermophilus, Thermus flavus, Thermoanaerobacterium thermosulfurigenes, Bacillus thermoproteolyticus, Thermotoga maritime, Thermomyces lanuginosus, Bacillus thermoproteolyticus,* and *Bacillus stearothermophilus*. Exemplary thermophilic proteins include citrate synthase, rubredoxin, glutamate dehydrogenase, and methionine aminopeptidase from *Pyrococcus furiosus*, EF-TU and EF-TU-TS from *Thermus aquaticus* and *Themius thermophilus*, inorganic pyrophosphatase and manganese superoxide dismutase from *Thermus thermophilus*, lactate dehydrogenase, 3-phosphoglycerate kinase, adenylate kinase, and phosphofructokinase from *Bacillus stearothermophilus*, malate dehydrogenase from *Thermus flavus*, cyclodextrin from *Thermoanaerobacterium thermosulfurigenes*, thermolysin, neutral protease, and ferredoxin from *Bacillus thermoproteolyticus*, cheY from *Thermotoga maritime*, and endo-1,4-beta xylanase from *Thermomyces lanuginosus*.

Further thermostable polypeptides include amylases, pullulanases, xylanases, chitinases, proteases, lipases, polymerases, and even cellulases. Note that while thermophilic cellulases were known in the art, it was heretofore unknown that EGV was the only thermostable cellulase expressed in *T. reesei*, at least in such quantities as to produce a significant amount of cellulase activity in whole cell lysates, broths, or partially purified cell protein preparations from *T. reesei*. Thus, the present compositions and methods can be used to produce exogenous thermostable cellulases in *T. reesei* host cells, which exogenous thermostable cellulases are substantially free of unwanted *T. reesei* cellulase activity.

Yet further thermostable polypeptides include structural polypeptides, transcription factors, chaperonins, and polypeptide inhibitors, to name only a few. An exemplary group of proteins that may be produced using the present compositions and methods are the hydrophobins, a class of cysteine-rich polypeptides expressed by filamentous fungi. Hydrophobins are small (~100 amino acids) polypeptides known for their ability to self-assemble and form amphipathic proteins. They may form a hydrophobic coating on the surface of objects, including cells and man-made materials. First discovered in *Schizophyllum* commune in 1991, hydrophobins have now been recognized in a number of filamentous fungi. Based on differences in hydropathy and other biophysical properties, hydrophobins are categorized as being class I or class II.

Suitable hydrophobins are any class I or class II hydrophobin known in the art, for example, hydrophobin from an *Agaricus* spp. (e.g., *Agaricus bisporus*), an *Agrocybe* spp. (e.g., *Agrocybe aegerita*), an *Ajellomyces* spp., (e.g., *Ajellomyces capsulatus, Ajellomyces dermatitidis*), an *Aspergillus* spp. (e.g., *Aspergillus arvii, Aspergillus brevipes, Aspergillus clavatus, Aspergillus duricaulis, Aspergillus ellipticus, Aspergillus flavus, Aspergillus fumigatus, Aspergillus fumisynnematus, Aspergillus lentulus, Aspergillus niger, Aspergillus unilateralis, Aspergillus viridinutans*), a *Beauveria* spp. (e.g., *Beauveria bassiana*), a *Claviceps* spp. (e.g., *Claviceps fusiformis*), a *Coccidioides* spp., (e.g., *Coccidioides posadasii*), a *Cochliobolus* spp. (e.g., *Cochliobolus heterostrophus*), a *Crinipellis* spp. (e.g., *Crinipellis perniciosa*), a *Cryphonectria* spp. (e.g., *Cryphonectria parasitica*), a *Davidiella* spp. (e.g., *Davidiella tassiana*), a *Dicxyonema* spp. (e.g., *Dictyonema glabratum*), an *Emericella* spp. (e.g., *Emericella nidulans*), a *Flammulina* spp. (e.g., *Flammulina velutipes*), a *Fusarium* spp. (e.g., *Fusarium culmorum*), a *Gibberella* spp. (e.g., *Gibberella moniliformis*), a *Glomerella* spp. (e.g., *Glomerella graminicola*), a *Grifola* spp. (e.g., *Grifola frondosa*), a *Heterobasidion* spp. (e.g., *Heterobasidion annosum*), a *Hypocrea* spp. (e.g., *Hypocrea jecorina, Hypocrea lixii, Hypocrea virens*), a *Laccaria* spp. (e.g., *Laccaria bicolor*), a *Lentinula* spp. (e.g., *Lentinula edodes*), a *Magnaporthe* spp. (e.g., *Magnaporthe oryzae*), a *Marasmius* spp. (e.g., *Marasmius cladophyllus*), a *Moniliophthora* spp. (e.g., *Moniliophthora perniciosa*), a *Neosartorya* spp. (e.g., *Neosartorya aureola, Neosartorya fennelliae, Neosartorya fischeri, Neosartorya glabra, Neosartorya hiratsukae, Neosartorya nishimurae, Neosartorya otanii, Neosartorya pseudofischeri, Neosartorya quadricincta, Neosartorya spathulata, Neosartotya spinosa, Neosartorya stramenia, Neosartorya udagawae*), a *Neurospora* spp. (e.g., *Neurospora crassa, Neurospora discreta, Neurospora intermedia, Neurospora sitophila, Neurospora tetrasperma*), a *Ophiostoma* spp. (e.g., *Ophiostoma novo-ulmi, Ophiostoma quercus*), a *Paracoccidioides* spp. (e.g., *Paracoccidioides brasiliensis*), a *Passalora* spp. (e.g., *Passalora fulva*), *Paxillus filamentosus Paxillus involutus*), a *Penicillium* spp. (e.g., *Penicillium camemberti, Penicillium chrysogenum, Penicillium marneffei*), a *Phlebiopsis* spp. (e.g., *Phlebiopsis gigantea*), a *Pisolithus* (e.g., *Pisolithus tinctorius*), a *Pleurotus* spp., (e.g., *Pleurotus ostreatus*), a *Podospora* spp. (e.g., *Podospora anserina*), a *Postia* spp. (e.g., *Postia placenta*), a *Pyrenophora* spp. (e.g., *Pyrenophora tritici-repentis*), a *Schizophyllum* spp. (e.g., *Schizophyllum* commune), a *Talaromyces* spp. (e.g., *Talaromyces stipitatus*), a *Trichoderma* spp. (e.g., *Trichoderma asperellum, Trichoderma atroviride, Trichoderma viride, Trichodenna reesii* [formerly *Hypocrea jecorina*]), a *Tricholoma* spp. (e.g., *Tricholoma terreum*), a *Uncinocarpus* spp. (e.g., *Uncinocarpus reesii*), a *Verticillium* spp. (e.g., *Verticillium dahliae*), a *Xanthodactylon* spp. (e.g., *Xanthodactylon flammeum*), a *Xanthoria* spp. (e.g., *Xanthoria calcicola, Xanthoria capensis, Xanthoria ectaneoides, Xanthoria flammea, Xanthoria karrooensis, Xanthoria ligulata, Xanthoria parietina, Xanthoria turbinata*), and the like. Hydrophobins are reviewed in, e.g., Sunde, M. et al. (2008) *Micron* 39:773-84; Linder, M. et al. (2005) *FEMS Microbiol. Rev.* 29:877-96; and Wösten, H. et al. (2001) *Ann. Rev. Microbiol.* 55:625-46.

Alternatively or additionally, proteins of interest may be mesophilic proteins that are minimally denatured at temperatures required to inactivate cellulases other than EGV. Proteins of interest may also be engineered proteins selected for their thermostability. Proteins of interest may also be those that are reversibly denatured at temperatures required to inactivate cellulases other than EGV, such that active or structurally intact proteins are recovered following exposure to elevated temperatures The polypeptide of interest, especially a thermostable polypeptide of interest may be recovered as discussed in WO/2011/019686, advantageously in accordance with the invention thereof, such as the techniques of Example 1 thereof.

In some embodiments, the present compositions and methods allow proteins of interest to be produced substantially in the absence of detectable enzymatic activities, including cellulase, mannanase, and/or protease activity. In other embodiments, proteins of interest are produced in the presence of small but detectable amounts of detectable cellulase, mannanase, and/or protease activity. For example, in particular embodiments, proteins of interest are produced in the presence of an endoglucanase activity of less than about 0.1 EGU, or even less than about 0.05 EGU, less than about 0.10 MMU, less than about 0.05 MMU, less than about 0.025 MMU, less than about 0.02 MMU, less than about 0.015 MMU, or even less than about 0.01 MMU, and/or a detectable cysteine protease activity of less than about 1.3 PU, or even less than about 0.5 PU. Where the protein of interest is, for example, hydrophobin intended for a food application, such amounts of contaminating activities are generally not detrimental.

Generally, proteins of interest may include any number of amino acid substitutions, insertions, and/or deletions, or chemical modifications, so long as the proteins retain thermostability or retain the ability to reversibly denature in response to thermal stress. Preferred proteins of interest retain at least about one-half (i.e., 50%) of their activity, binding ability, or native structure (depending on the type of protein) following exposure to a temperature of at least about 70° C., at least about 75° C., at least about 80° C., at least about 85° C., at least about 90° C., or even at least about 95° C., for a time of at least about 3 minutes, at least about 5 minutes, at least about 10 minutes, at least about 15 minutes, at least about 20 minutes, or even at least about 30 minutes. In a particular case, the proteins of interest retain at least about 50% of their activity, binding ability, or native structure following exposure to a temperature of at least about 90° C. for a time of at least about 5 minutes.

Genes of interest or nucleic acid molecules of interest may be introduced into *Trichoderma* cell using any known methods, including homologous recombination, transfection using transient expression vectors, stable integrating expression vectors, or artificial chromosomes, infection/transduction with viruses, and the like. In some cases, it may be desirable to introduce a gene of interest at the site of egl5, which is to be disrupted. In some cases, there may be more than one gene or nucleic acid molecule of interest.

In one aspect, the present compositions and methods allow the expression of thermostable proteins, such as hydrophobin, using a *Trichoderma*, e.g., *T. reesei*, host cell deleted or disrupted with respect to egl5 but optionally encoding other cellulase-genes. Following expression of the thermostable protein, a whole cell lysate, broth, or partially purified cell protein preparation from *Trichoderma* is incubated at a temperature sufficient to inactivate heat labile enzymes, producing the protein of interest in the absence of unwanted enzymatic activity, including but not limited to unwanted cellulase [including endoglucanase (other than EGV), exoglucanase, cellobiohydrolase, β-glucosidase, carboxymethyl cellulase, and the like], hemicellulase (including xylanase, mannanase, arabinanase, glucuronidase, acetylxylan esterase, arabinofuranosidase, xylosidases, and the like), protease, lipase, amylase, esterase, perhydrolase, phytase, laccase, and other commercially-relevant enzyme activities, all while avoiding the need to disrupt a number of different heat-labile enzyme-encoding genes in the host cell. This greatly simplifies the expression of genes or nucleic acid molecules of interest in *Trichoderma*.

In another aspect, the present compositions and methods allow the expression of thermostable proteins, such as hydrophobin, e.g., hydrophobin II, using a *Trichoderma* host cell deleted or disrupted essentially with respect to egl5 but optionally expressing other cellulases or encoding other cellulase-genes. Following expression of the thermostable protein, a whole cell lysate, broth, or partially purified cell protein preparation from *Trichoderma* is incubated at a temperature sufficient to inactivate heat labile enzymes, producing the protein of interest in the absence of unwanted enzymatic activity, including but not limited to unwanted cellulase [including endoglucanase (other than EGV), exoglucanase, cellobiohydrolase, β-glucosidase, carboxymethyl cellulase, and the like], hemicellulase (including xylanase, mannanase, arabinanase, glucuronidase, acetylxylan esterase, arabinofuranosidase, xylosidases, and the like), protease, lipase, amylase, esterase, perhydrolase, phytase, laccase, and other commercially-relevant enzyme activities, all while avoiding the need to disrupt a number of different heat-labile enzyme-encoding genes in the host cell.

In another aspect, the present compositions and methods allow the expression of thermostable proteins, such as hydrophobin, using a *Trichoderma* host cell modified to substantially reduce or prevent the production of a thermostable endoglucananse V (EGV) polypeptide wherein the modification comprises or consists essentially of deleting a nucleic acid molecule encoding or providing expression of EGV from the *Trichoderma* host cell, wherein the nucleic acid molecule encoding EGV is egl5, is provided.

In another aspect, the present compositions and methods provide a composition obtained from a host cell, in which hydrophobin, e.g., hydrophobin II is present, with an absence of cellulase and/or mannanase activity. Such a composition may be obtained by producing hydrophobin, e.g., hydrophobin II in a host cell, such as filamentous fungus cells, such as, *Trichoderma*, e.g., *T. reesei*, that also produces thermolabile cellulase and/or mannanase polypeptides, and then subjecting the proteins produced by the host cell to an elevated temperature to inactivate the cellulase and/or mannanase polypeptides. Alternatively, hydrophobin may be produced in a host cell such as, *Trichoderma*, e.g., *T. reesei*, having deleted and/or disrupted nucleic acid molecule(s) encoding or responsible for expression of cellulase and/or mannanase polypeptides, or lacking nucleic acid molecule(s) encoding cellulase and/or mannanase polypeptides. Such compositions are useful in applications requiring hydrophobin, e.g., hydrophobin II, where the presence of cellulase and/or mannanase activity is undesirable.

These and other aspects and embodiments of the present compositions and method will be apparent to the skilled person in view of the present description.

Indeed, mention is made that the skilled person can practice the instant invention in combination with the inventions of each or both of U.S. application Ser. No. 61/469,067 filed 29 Mar. 2011 and Ser. No. 61/475,933 filed 15 Apr. 2011, both of which are incorporated herein by reference. Specifically, the skilled person can, in conjunction with the instant invention, use the method for purifying hydrophobin II of U.S. application Ser. No. 61/475,933 filed 15 Apr. 2011 at any point after hydrophobin II is expressed in the practice of the present invention, including before or after a heat treatment; and, that method for purifying may comprise adding a C1-C3 alcohol, e.g., isopropanol, to a hydrophobin solution to generate a first precipitate, decanting a supernatant from the C1-C3 alcohol/hydrophobin solution and adding the C1-C3 alcohol to the supernatant, to generate a second precipitate, wherein the second precipitate may be purified hydrophobin II. And, one may use the precipitation agent techniques of U.S. application Ser. No. 61/469,067 filed 29 Mar. 2011 during the expression of hydrophobin II when the instant invention is practiced.

The present invention method also relates to controlling activity of the polypeptide of interest expressed by the modified *Trichoderma* host cells of the present invention, wherein the polypeptide of interest is heat sensitive or thermolabile, wherein said method may comprise subjecting the heat sensitive or thermolabile polypeptide of interest and the endogenous polypeptide to an elevated temperature, wherein the elevated temperature may be sufficient to inactivate the endogenous polypeptide and the heat sensitive or thermolabile polypeptide. In an advantageous embodiment, the endogenous polypeptide may be a cellulose. The method may further comprise, prior to subjecting the heat sensitive or thermolabile polypeptide of interest to the elevated temperature, contacting the polypeptide of interest with a compound upon which the polypeptide of interest acts. The method may further comprise, prior to subjecting the heat sensitive or thermolabile polypeptide of interest to the elevated temperature, contacting the polypeptide of interest with one or more compounds upon which the cellulose and the polypeptide of interest act.

The present invention method also relates to a method for controlling activity of the polypeptide of interest in the fermentation broth of the present invention, wherein the polypeptide of interest may be heat sensitive or thermolabile, wherein the method may comprise subjecting the fermentation broth to an elevated temperature sufficient to inactivate the endogenous polypeptide and the heat-sensitive or thermolabile polypeptide. In an advantageous embodiment, the endogenous polypeptide may be a cellulose. The method may further comprise, prior to subjecting the fermentation broth to the elevated temperature, contacting the fermentation broth with a compound of interest upon which the polypeptide of interest acts. The method may further comprise, prior to subjecting the fermentation broth to the elevated temperature, contacting the fermentation broth with one or more compounds upon which the cellulase and the polypeptide of interest act.

A compound upon which the polypeptide of interest and/or a cellulase acts may be any compound which directly or indirectly interacts with the polypeptide of interest and/or a cellulase. The compound of interest may be a compound that binds directly to the polypeptide of interest and/or a cellulase, i.e., a cis-acting compound. In one embodiment, the compound of interest may be a substrate of the polypeptide of interest and/or a cellulase, such as, for example, a cellulose, a hemicelluloses, a lignin, a pectin or a derivative thereof. Examples include, but are not limited to, cellulose acetate, cellulose triacetate, cellulose propionate, cellulose acetate propionate, cellulose acetate butyrate, nitrocellulose (cellulose nitrate), cellulose sulfate, methylcellulose, ethylcellulose, ethyl methyl cellulose, hydroxyethyl cellulose, hydroxypropyl cellulose (HPC), hydroxyethyl methyl cellulose, hydroxypropyl methyl cellulose (HPMC), ethyl hydroxyethyl cellulose and carboxymethyl cellulose (CMC). In another embodiment, the compound of interest may be a compound that indirectly interacts with the polypeptide of interest and/or a cellulase, i.e., a trans-acting compound.

The present invention also relates to a method for controlling the activity of a cellulase present in a composition obtained from the modified *Trichoderma* host cells, wherein the composition may comprise at least one cellulase enzyme other than EGV, and the method may comprise subjecting the composition to an elevated temperature sufficient to inactivate the polypeptide of interest, and wherein following subjecting the composition to an elevated temperature the composition is substantially free of cellulase activity. The polypeptide of interest may be heat sensitive or thermolabile. In another embodiment, the polypeptide may be heat tolerant or thermostable. The subjecting the composition to an elevated temperature may be performed in a foodstuff or beverage. In another embodiment, the elevated temperature may be less than about 100 degrees C. The elevated temperature of the present invention is not meant to encompass baking, frying, pasturization, or other heat treatments, which destroy thermostable cellulases. In another embodiment, the composition obtained from the modified *Trichoderma* host cells may be a hydrophobin-comprising fermentation broth.

The following examples are intended to further illustrate, but not limit, the compositions and methods.

EXAMPLES

Example 1. Construction of a *T. reesei* Strain with a Disrupted pyr2 Gene

A fragment of sucA from *Aspergillus niger* was amplified by PCR using primers oANSUCA5 and oANSUCA3. Similarly, the hexokinase gene promoter was amplified from the chromosome of *T. reesei* using primers oHXK5 and oHXK3. The amplified sucA DNA fragment was restricted with EcoRI and AscI. The amplified DNA fragment carrying the hexokinase promoter was digested with HindIII and EcoRI. The two digested fragments were incubated together in a ligation reaction along with plasmid pTrex3(AGL51M) (see WO 08/118382, incorporated herein by reference) digested with HindIII and AscI. The resulting vector, pTHXK (SUCA) was digested with HindIII and BamHI and a 3.5 kb DNA fragment carrying a fragment of the sucA gene fused with the hexokinase promoter was isolated by agarose gel electrophoresis. The nucleotide sequence of this fragment is provided in FIG. 7 and is herein designated SEQ ID NO: 1:

pF1X is a small plasmid comprising an origin of replication and an ampicillin resistance gene from pUC19 and a bacteriophage fl origin of replication. Its complete nucleotide sequence is provided in FIG. 8 and is herein designated as SEQ ID NO: 2:

The pyr2 gene of *T. reesei* was amplified using primers oPYR2 51 and oPYR2 31. The resulting fragment was digested with SfiI and NotI and incubated in a ligation reaction along with pF1X digested with the same enzymes. The resulting plasmid was designated pF1X(pyr2hxksuc). The *E. coli* strain XL1-Blue MRF' was transformed with pF1X(pyr2hxksuc) and transfected with the helper phage M13K07 (Invitrogen). The DNA from the phagemid form of pF1X(pyr2hxksuc) was isolated using standard methods (see, e.g., instructions from Invitrogen).

The phagemid DNA was dissolved in H-restriction enzyme buffer at about 1 mg/ml concentration and annealed to the two oligonucleotides oPYR2F_3M and oPYR2_5P, both present a concentration of 5 μM, by heating the solution to 75° C. and letting it cool to room temperature slowly. The resulting, partially double-stranded DNA was digested with BamHI and the larger of the two resulting DNA fragments from this digest purified by agarose gel electrophoresis.

The larger BamHI DNA fragment was used to transform a quad-deleted (Δcbh1, Δcbh2, Δeg1 and Δeg2) strain (i.e., "Quad;" U.S. Pat. No. 5,650,322) of *T. reesei* by spore electroporation (see, e.g., Miasnikov, A. and Kim, S. (2009) Abstracts of the 25th Fungal Genetics conference at Asilomar. p. 232). Transformants were selected for their ability to grow on sucrose minimal medium (sucrose, 5 g/l; $KH_2PO_4$, 5 g/l; $(NH_4)_2SO_4$, 6.6 g/l; $MgCl_2$, 1 g/l; $MgSO_4$, 0.1 g/l; $CaCl_2$, 0.25 g/l; $FeSO_4$, 5.0 mg/l; $MnSO_4$, 1.6 mg/l; $ZnSO_4$, 1.4 mg/l; uridine, 100 mg/l). Transformants that grew on sucrose were sub-cultured on plates containing the same medium with 1 g/l fluoroorotic acid (FOA). Chromosomal DNA was isolated from the transformant (coded DURA) that demonstrated the best growth in the presence of FOA. This DNA was analyzed by PCR using primer pairs (i) oPYR2FD_R1 and oSUC2_D1 and (ii) oPYR2FU_D1 and oSUC2_R1. In both cases, PCR products of the expected size (2.4 and 1.8 kb, respectively) were observed. Strain DURA did not grow on sucrose minimal medium lacking uridine, confirming that the pyr2 gene is disrupted in this strain.

The sequences of the primers referred to in this Example are described in Table 1.

TABLE 1

Primers used for disruption of the pyr2 gene

| Name | Oligo Sequence (5'→3') | SEQ ID NO |
|---|---|---|
| oANSUCA5 | GGAATTCAAACATGTCGCCTTCCATGCAG ACGCGGGCCTC | 4 |
| oANSUCA3 | GTTGGCGCGCCTGGATCCCGAAACTTCAC CTGCTAC | 5 |
| oHXK5 | CGATAAGCGATTGGCGAGCGAGCTTTG | 6 |
| oHXK3 | GGTGAATTCTGGCGGGGTAGCTGTTGAAA AGTG | 7 |
| oPYR2 51 | GTTTCGGCCATTTAGGCCGGATCCACACC TTGCTCCTGTCGCATGCGTATCTGG | 8 |
| oPYR2 31 | GTTTGCGGCCGCGGATCCTGCTCAGCACA ATGTCCAGAAACTCCTGGTG | 9 |

TABLE 1-continued

Primers used for disruption of the pyr2 gene

| Name | Oligo Sequence (5'→3') | SEQ ID NO |
|---|---|---|
| oPYR2F_3M | GCCGGATCCACACCTTGCTCCTGTCGCATG | 10 |
| oPYR2_5P | GCAGGATCCGCGGCCGCAAACTCATCAATG | 11 |
| oPYR2FD_R1 | GCGTGGTTTCAGCAGCCCACTGGTGAGTG | 12 |
| oSUC2_D1 | GCCAGACTGCAATTCCGTCAACAATAACG | 13 |
| oPYR2FU_D1 | AGCCGGCACGGATCTGAGTGGGCAGTTTG | 14 |
| oSUC2_R1 | GGTTTGGAGGTGCGACATTGTAGTCGATG | 15 |

Example 2. Disruption of the egl5 Gene

The *T. reesei* egl5 gene was amplified by PCR using *T. reesei* chromosomal DNA as a template and the primers oEG5_5 and oEG5_3. The amplified DNA fragment was digested with restriction endonucleases SfiI and NotI and cloned into pF1X digested with the same enzymes, resulting in plasmid pF1X(EG5). Another fragment of *T. reesei* chromosomal DNA, located further upstream of the egl5 coding region (subsequently referred to as "repeat region"), was similarly amplified using the primers oEG5R_5 and oEG5R_3. The amplified fragment was digested with SpeI and SalI and cloned into pF1X(EG5) digested with AvaII and XhoI, generating plasmid pF1X(EG5R).

Figure 2:
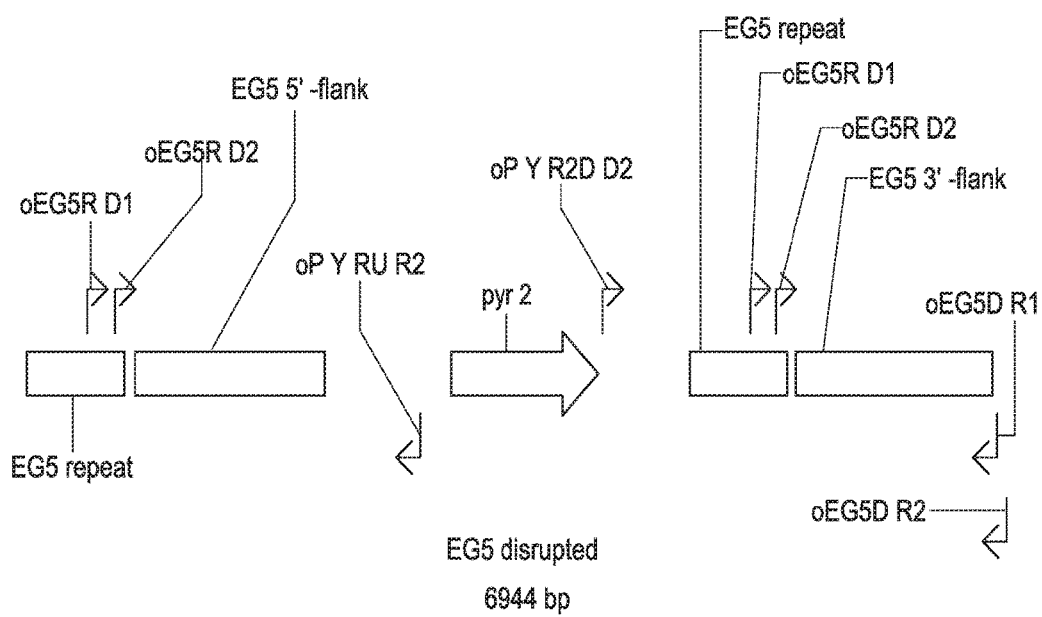
FIG. 2 is a map of a portion of the *T. reesei* chromosome following disruption of the egl5.

The last step of constructing of the egl5 disruption cassette was to amplify the *T. reesei* pyr2 gene by PCR using the primers oPYR2_55 and oPYR2_35 and chromosomal DNA of the quad-deleted *T. reesei* strain (supra) as the template, digest the amplified DNA fragment with XhoI and SpeI, and incubate the digested fragmentin a ligation reaction along with XhoI and XbaI-digested pFl(EG5R). The final plasmid, designated pFIX(EG5RPyr2) carried the *T. reesei* egl5 gene disrupted with both a functional copy of the pyr2 gene and the egl5 5'-repeat region (FIG. 1). The DNA sequence of the disrupted gene (i.e., "disruption cassette") was deduced based on the known chromosomal DNA sequences of egl5 and pyr2 genes, the aforedescribed construction scheme, and multiple restriction endonuclease analyses. This sequence is provided in FIG. 9 (which is comprised of FIGS. 9A and 9B) and is herein designated as SEQ ID NO: 3:

The disruption cassette was amplified by PCR using pF1X(EG5RPyr2) as a template and the primers oEG5f and oEG5r. The PCR product was used to transform the *T. reesei* strain DURA (described in Example 1) to impart uridine prototrophy. The chromosomal DNA was isolated from a number of transformants and analyzed by PCR using the primer pairs: oEG5R_D1 and oEG5D_R1, oEG5R_D2 and oEG5DR2, oEG5R_D2 and oPYR2U_R2, and oPYR2D_D2 and oEG5D_R2. Three transformants (i.e., DURA ΔEG5 18, DURA ΔEG5 22, and DURA ΔEG5 23) yielded PCR products of the expected sizes with all four primer pairs (i.e., 1.2 kb, 1.15 kb, 1.4 kb, and 1.5 kb, respectively; FIG. 2). These three strains were selected for biochemical characterization of their cellulase activity.

The sequences of the primers referred to in this Example are described in Table 2.

TABLE 2

Primers used for making and analyzing the egl5 gene disruption

| Name | Oligo Sequence (5'→>3') | SEQ ID NO: |
|---|---|---|
| oEG5_5 | GTTGCGGCCGCAATTCAGATATTCCAAATCATCTTGCAC | 16 |
| oEG5_3 | GTGGCCATTTAGGCCATGGGATCGTACGGCATAATACATC | 17 |
| oEG5R_5 | GTTACTAGTCTCGAGTTTTCTAGAGCCGACGAGTATCGTGGGCAATTGC | 18 |
| oEG5R_3 | GTTGTCGACGTCGTGCAAGATGATTTGGAATATC | 19 |
| oPYR2_55 | AGTACTAGTCAATTGCTCGAGTTTATAAGTGACAACATGC | 20 |
| oPYR2_35 | TTGCAATTGACTAGTGGATCCAACGCCGGCTATTAGGCCATAAG | 21 |
| oEG5f | AATTAATGAAGCAAAATAGAGTATTTTCAC | 22 |
| oEG5r | GATCGTACGGCATAATACATCGGCCAAATG | 23 |
| oEG5D_RI | CCTAGATCCGGGAATTCCCATGGGATCGTAC | 24 |
| oEG5D_R2 | CTGACAGCGAGCTACCTTACATGTACATAAG | 25 |
| oEG5R_DI | GGCGCATCATATCAAGAAACAGAATGATACTC | 26 |
| oEG5R_D2 | CACAAGAAGACCCACGTCAGAGAAGACAAAG | 27 |
| oEG5FU_DI | GGAAGAAGCCATGCTCAAGCGCATTTCTAC | 28 |
| oEG5FU_D2 | ATCGCCACGCCAATGACCCAGCAGTTTCTC | 29 |
| oPYR2D_D2 | GAAAAGGTGGAAAGAAGAGGCAAATTGTTG | 30 |
| oPYR2U_R2 | GAGTTTTCACATGGAAGTCAAAGCGTACAG | 31 |

Example 3. Cellulose Activity in *T. reesei* Control and egl5 Deletion Strains Based on Detection of Reducing Sugars

*T. reesei* strains Quad (as a control), and independently isolated transformants DURA ΔEG5 18, DURA ΔEG5 22, and DURA ΔEG5 23, were grown for 6 days at 28° C. in shake-flasks using a minimal medium with 1.6% glucose-sophorose mixture as the carbon and energy source. Mycelia were separated by filtration through a 0.22 γm membrane and the culture supernatants were concentrated about 100-fold by ultra-filtration using a 10 kDa-cutoff membrane.

Figure 3:
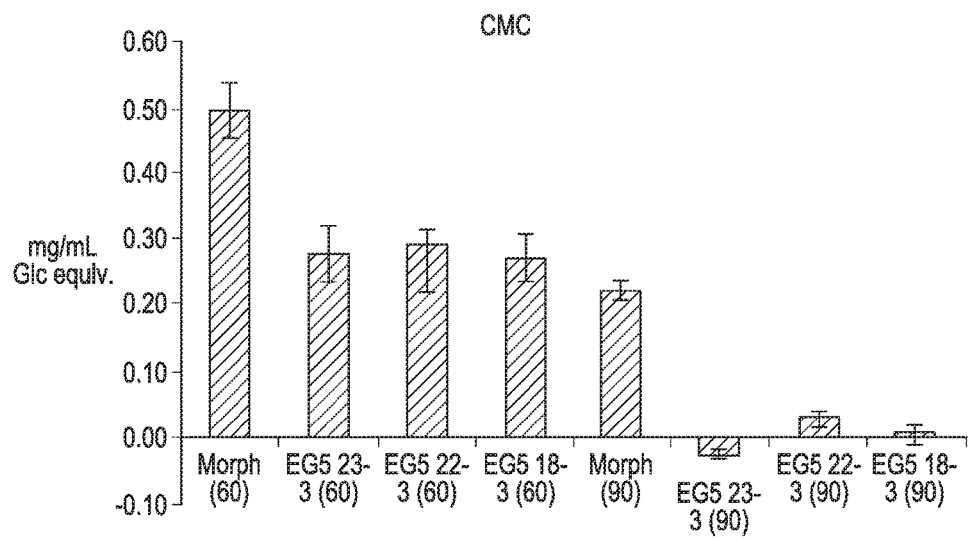
FIG. 3 is a graph showing the amount of cellulase activity present in the in the supernatants of control and egl5-deletion *T. reesei* cultures, with and without heat treatment.
Figure 4:
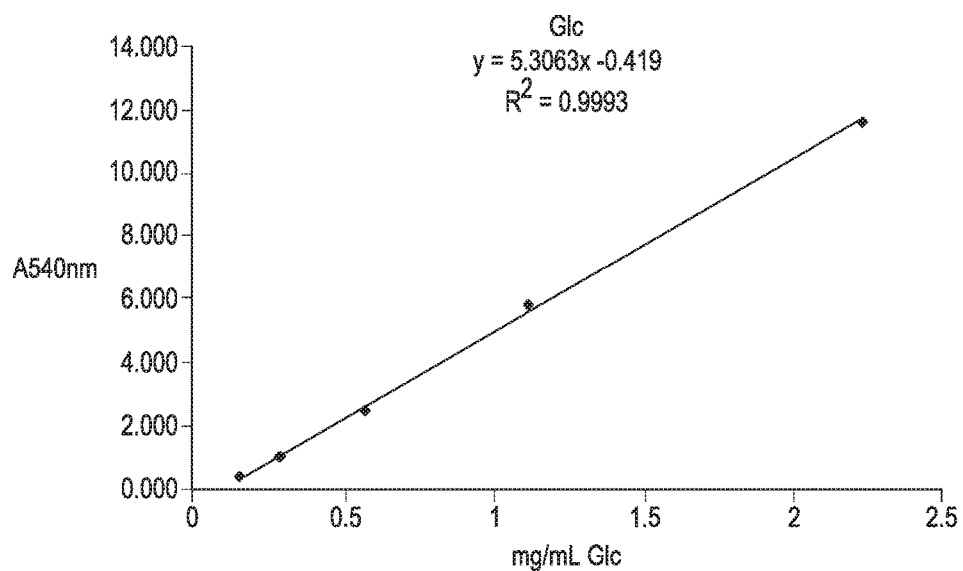
FIG. 4 is a graph showing a glucose standard curve.

Concentrated culture supernatants (100 μl) were diluted with water (100 μl) and heated to 60° C. or 90° C. for 60 minutes in an Eppendorf Thermomixer R PCR machine. Heat-treated supernatants (10 μL) were then mixed with 195 μl polysaccharide substrate (0.5% carboxymethyl cellulose, 50 mM sodium citrate, pH 5.45) in a 96 well plate. The plate was covered with aluminum seal film and incubated at 40° C. for 16 hours with shaking at 400 rpm. A portion of the resulting cellulase reaction mixture (75 μL) was mixed with 75 μL DNS reagent (1% 3,5-dinitrosalicylic acid, 1% NaOH, 0.2% phenol, 0.05% sodium metabisulfite, and 10% sodium potassium tartrate) in a 96 well PCR plate and incubated at 99° C. for 10 minutes in an Eppendorf Thermomixer R PCR machine. DNS is used to measure the amounts of reducing sugars. The absorbance at 540 nm of the resulting DNS reaction (100 μL) was measured in a clear-bottom 96 well plate (Molecular Devices SpectraMax M2 UV plate reader). The activity was reported as the concentration of glucose (Glc) equivalents released (FIG. 3). The $A_{540}$ readings were corrected for background and correlated with glucose equivalents from a glucose standard curve (FIG. 4).

No cellulase activity was detected in any of the three *T. reesei* strains with the deleted egl5 gene. The control Quad strain retained about one half of its original cellulase activity after being subjected to heat treatment at 90° C. Results based on three replicates are shown in Table 3.

The experiment demonstrates that deletion of the egl5 gene from a *T. reesei* strain that includes other functional cellulase genes (i.e., other than egl5), permits all cellulase activity in cell materials to be abolished by exposure to an elevated temperature. The use of an elevated temperature to abolish all cellulase activity is not possible when a from a *T. reesei* strain includes a functional egl5 gene, because the EGV cellulase gene product is thermostable.

TABLE 3

Cellulase activity in heat-treated supernatants (DNS assay)

| Sample/strain | Heat treat temp. (° C.) | $A_{540}$ (average) | $A_{540}$ (standard devation) |
|---|---|---|---|
| Quad | 60 | 0.49 | 0.04 |
| DURA ΔEG5 23 | 60 | 0.28 | 0.04 |
| DURA ΔEG5 22 | 60 | 0.29 | 0.02 |
| DURA ΔEG5 18 | 60 | 0.27 | 0.03 |
| Quad | 90 | 0.22 | 0.02 |
| DURA ΔEG5 23 | 90 | −0.03 | 0.01 |
| DURA ΔEG5 22 | 90 | 0.03 | 0.01 |
| DURA ΔEG5 18 | 90 | 0.01 | 0.02 |

Example 4. Cellulase Activity Assay Based on Changes in Viscosity

Figure 5:
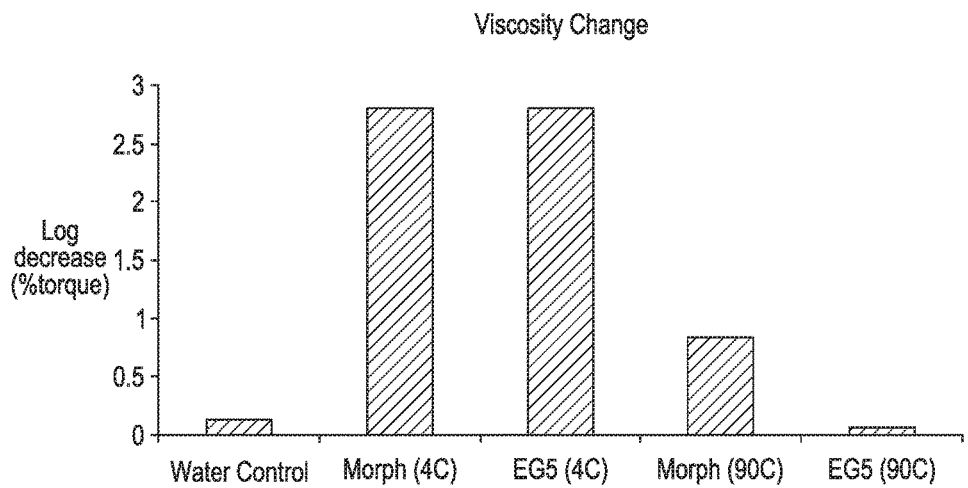
FIG. 5 is a graph showing the loss of heat-stable cellulase activity in the supernatant from a ΔEG5 strain compared to a control strain.

Polysaccharide substrate [300 mL, 1.0% carboxymethyl cellulose (CMC), 50 mM sodium citrate (pH 5.45)] was added to 400 mL glass beakers and initial viscosity was measured (Brookfield Viscometer DV-II Pro, spindle 62, 10 rpm). In preparation for addition to these CMC solutions/suspensions, concentrated culture supernatants (220 μL) from *T. reesei* control or egl5-deletion strains were incubated at either 4° C. or 90° C. for 60 minutes in an Eppendorf Thermomixer R PCR machine. Portions of the heat-treated supernatants (100 μL) were added to the CMC solutions/suspensions and stirred at 150 rpm at 22° C. for 16 hours. The final viscosities of the reactions were measured as above. The results are shown in Table 4 and FIG. 5. Activity was reported as the log fold change in % torque at 10 rpm.

Incubation of the CMC solution/suspension with culture supernatant from the Quad (control) strain lead to a significant decrease in viscosity independent of heat-treatment. Culture supernatant from the DURA ΔEG5 18 strain also produced a significant reduction in the viscosity of the CMC solution/suspension but not after heat-treatment at 90° C. These result suggested that EGV was the only heat-stable cellulase present in *T. reesei* cells, and that deletion of the egl5 gene in *T. reesei* allowed heat inactivation of all cellulase enzymes present in a *T. reesei* culture supernatant.

TABLE 4

Cellulase activity based on a viscosity assay

| Sample | Pre-incubation temperature (° C.) | % torque (initial) | % torque (final) | Fold decrease |
|---|---|---|---|---|
| Water control | | 63 | 47 | 1.34 |
| Quad (4° C.) | 4 | 64 | 0.1 | 640.00 |
| DURA ΔEG5 18 | 4 | 63 | 0.1 | 630.00 |
| Quad | 90 | 62 | 9 | 6.89 |
| DURA ΔEG5 18 | 90 | 62 | 53 | 1.17 |

Example 5. Excision of the pyr2 Marker from egl5 Disrupted Strains

Figure 6:
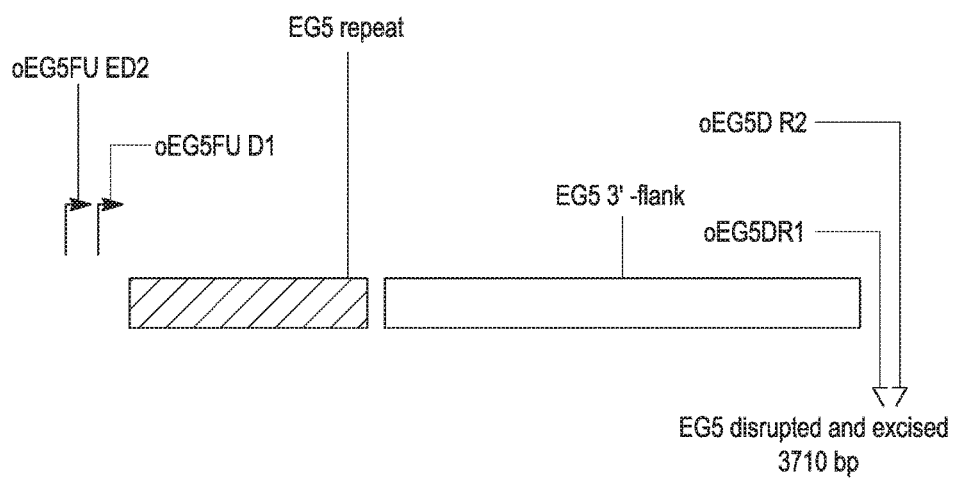
FIG. 6 is a map of a portion of the *T. reesei* chromosome following disruption of the egl5 and excision of the pyr2 marker.

Strains DURA ΔEG5 18, DURA ΔEG5 22, and DURA ΔEG5 23 were allowed to sporulate and the spore suspensions were plated onto the sucrose minimal medium supplemented with uridine and FOA. A few FOA resistant clones were selected from the progeny of each of the three strains, and their chromosomal DNA isolated and analyzed by PCR using primer pairs (i) oEG5FU_D1 and oEG5D_R1 and (ii) oEG5FU_D2 and oEG5D_R2 (as described in Table 2). Chromosomal DNA obtained from the large majority of analyzed clones produced PCR products of the size expected (i.e., about 1.6-1.7 kb) following a homologous recombination between the two "repeat regions" in the chromosomes of DURA ΔEG5 18, DURA ΔEG5 22, and DURA ΔEGS 23 (FIG. 6).

Example 6. Cellulase and Mannanse Activity Assays

The following assays were used to measure cellulase activity and mannanse activity in hydrophobin preparations:
Cellulase Assay Cellulase activity was determined using 4-methylumbellifery β-D-cellobioside (4MUC, SigmaAldrich, M6018) as a substrate in 100 mM sodium acetate buffer, pH 5.5. A standard cellulase composition (i.e., EG3 cellulase, Genencor) was used as a reference. Serial dilutions of the sample composition (e.g., a hydrophobin-comprising fermentation broth) and the standard cellulase composition were prepared and incubated with 4MUC reagent for 1 hr at 40° C. in a plate incubator with shaking at 400 rpm.

Fluorescence was read on a SpectraMax fluorescence plate reader using the following parameters: excitation=360 nm, emission=460 nm, auto cutoff=455 nm. The amount of fluorescent signal produced by the experimental samples was correlated with the amount of fluorescent signal produced by the standard cellulase composition and reported as NPC/mL=μmole o-nitrophenol liberated/min/mL (a standard measure of cellulase activity).

Mannanase Assay

Mannanase activity was determined using 4-methylumbelliferyl β-D-mannopyranoside (4MUM, SigmaAldrich, M0905) as a substrate in 100 mM sodium acetate buffer, pH 5.5. A standard mannanase composition (Genencor) was used as a reference. Serial dilutions of the sample composition (e.g., a hydrophobin-comprising fermentation broth) and the standard mannanase composition are prepared and incubated with 4MUM reagent for 1 hr at 40° C. in a plate incubator with shaking at 400 rpm.

Fluorescence was read on a SpectraMax fluorescence plate reader using the following parameters: excitation=360 nm, emission=460 nm, auto cutoff=455 nm. The amount of fluorescent signal produced by the experimental samples was correlated with amount of fluorescent signal produced by the standard mannanase composition and reported as MU/L=µmole o-nitrophenol liberated/min/mL.

Assay of Hydrophobin Produced as Described

Residual cellulase and mannanase activities in a hydrophobin-containing fermentation broth composition produced as described, were tested by incubating samples with 4-methylumbelliferyl β-D-cellobioside (cellulase) or 4-methylumbelliferyl β-D-annopyranoside (mannanase), as described, and comparing these values to those obtained using the EG3 cellulase standard or Mannanase standard (Genencor). The data (shown in Table 5) are expressed as activity per mL (or L) of solution or as activity per gram of hydrophobin. In this fermentation broth composition, cells were removed by microfiltration and the proteins were concentrated by ultrafiltration; however, no purification steps were performed to alter the ratio of hydrophobin to other proteins, such as residual mannanases and cellulase.

TABLE 5

Residual mannanase and cellulase activity in a fermentation broth composition

| Sample | NCP/mL | MU/L | NCP/g HFB | MU/g HFB |
|---|---|---|---|---|
| Concentrate #1 | 2282.504 | 139.646 | 13077.401 | 0.800 |
| Concentrate #2 | 929.546 | 14.347 | 4786.125 | 0.074 |
| Heat-treated concentrate #2 | 0.241 | 1.936 | 1.494 | 0.012 |

As shown in the Table, the levels of residual mannanase activity, and particularly and cellulase were significantly reduced following heat treatment.

Example 7. HFB2 Expression in an egl5-Deleted Strain

Construction of pTrex8R(Hfb2) and pTrex3gM(Hfb2)

Figure 12:
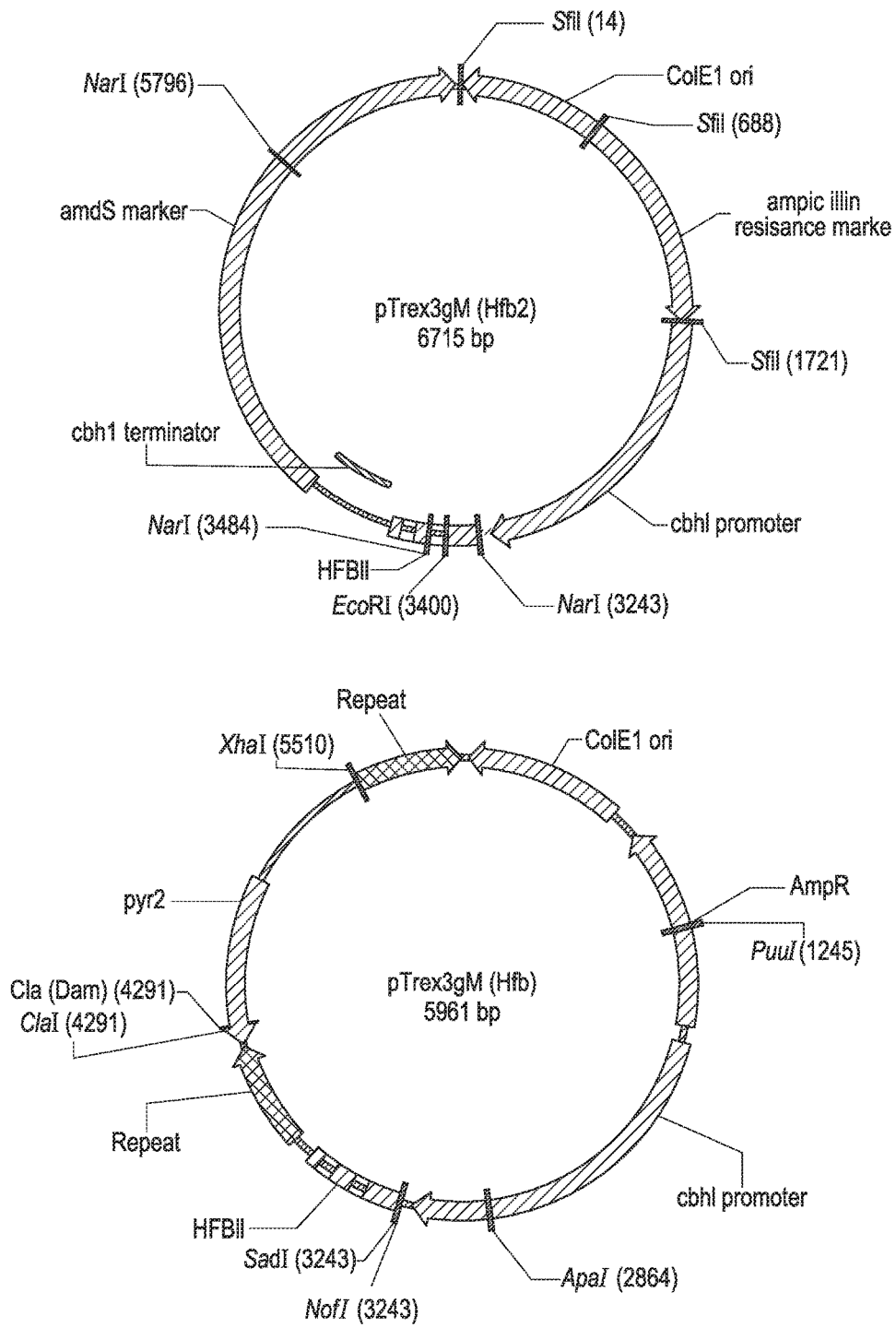
FIG. 12 are functional and partial restriction maps of vectors pTrex3gM(Hfb2) and pTrex8R(Hfb2).

Two vectors were both designed to drive the expression of HFB2 from its native coding sequence under control of a strong cbhI promoter. The expression cassettes of the two vectors are identical, the only difference between these two molecules is that pTrex3gM(Hfb2) has amdS gene as the selectable marker while pTrex8R(Hfb2) has pyr2. Both vectors were constructed by LR-Gateway® cloning procedure using a chromosomal copy of hfb2 gene cloned in pENTR TOPO/D vector and destination vectors pTrex3gM and pTrex8R. Table 6 provides a complete list of functional elements in plasmids pTrex8R(hfb2) and pTrex3gM(hfb2). Any sequences not listed in Table 6 are short fragments of DNA used for genetic engineering purposes like restriction sites or sequences generated by LR-Gateway® reaction. Functional and partial restriction maps of plasmids pTrex8R (Hfb2) and pTrex3gM(Hfb2) are provided in FIG. 12. Their complete nucleotide sequences are listed in FIG. 13.

TABLE 3

Functional elements comprising the plasmids pTrex8R(hfb2) and pTrex3gM(hfb2)

| | pTrex3gM(Hfb2) | | pTrex8R(Hfb2) | |
|---|---|---|---|---|
| Functional element | Start | End | Start | End |
| ColE1 replication origin | 18 | 681 | 18 | 681 |
| ampicillin resistance marker | 689 | 1725 | 689 | 1725 |

TABLE 3-continued

Functional elements comprising the plasmids pTrex8R(hfb2) and pTrex3gM(hfb2)

| | pTrex3gM(Hfb2) | | pTrex8R(Hfb2) | |
|---|---|---|---|---|
| Functional element | Start | End | Start | End |
| cbh1 promoter | 1734 | 3185 | 1734 | 3185 |
| hfb2 coding sequence | 3262 | 3664 | 3262 | 3664 |
| cbh1 terminator | 3754 | 4078 | 3754 | 4078 |
| amdS marker | 4091 | 6713 | — | — |
| pyr2 marker | — | — | 4091 | 5961 |

Transformation of *T. reesei* DUD5 with the HFB2 Expression Cassettes

The transformation was done in two successive stages. Firstly, strain DUD5 was transformed with an isolated large SfiI fragment of plasmid pTrex8R(hfb2) to uridine prototrophy using the standard protoplast transformation technique. Three clones (DUD5 HFB#176, #194 and #228) were selected after screening the culture media of a random set of transformants for high level of expression of HFB2. These isolates were further transformed with a large SfiI fragment of the plasmid pTrex3gM(hfb2) to acetamide assimilation phenotype. After a second round of screening (again, by growing the individual transformants in liquid culture under conditions inducing cbhI promoter and analyzing the culture media by SDS PAGE) clones DUD5 HFB2 B, DUD5 HFB2 D, DUD5 HFB2 K and DUD5 HFB2 N were selected as the best HFB2 producers.

The invention is further described by the following numbered paragraphs:

1. A *Trichoderma* host cell modified to substantially reduce or prevent the production of a thermostable EGV polypeptide.

2. The *Trichoderma* host cell of paragraph 1, comprising a disrupted egl5 gene.

3. The *Trichoderma* host cell of paragraph 1 or 2, comprising a deleted egl5 gene.

4. The *Trichoderma* host cell of any of the preceding paragraphs, wherein the egl5 gene is deleted by homologous recombination.

5. The *Trichoderma* host cell of any of the preceding paragraphs, produced by modifying a parental host cell comprising a functional egl5 gene.

6. The *Trichoderma* host cell of any of the preceding paragraphs, further comprising one or more endogenous functional genes encoding a thermolabile enzyme.

7. The *Trichoderma* host cell of any of the preceding paragraphs, further comprising one or more functional genes encoding a thermolabile enzyme selected from the group consisting of a cellulase, a hemi-cellulase, and a protease.

8. The *Trichoderma* host cell of any of the preceding paragraphs, further comprising a functional gene encoding a thermolabile cellulase or hemi-cellulase.

9. The *Trichoderma* host cell of any of the preceding paragraphs, further comprising a functional gene of interest.

10. The *Trichoderma* host cell of paragraph 9, wherein the gene of interest encodes a thermostable polypeptide.

11. The *Trichoderma* host cell of paragraph 10, wherein the thermostable polypeptide is a hydrophobin.

12. A method for making a thermostable protein of interest in the *Trichoderma* host cell, comprising:
   introducing a gene encoding the thermostable protein of interest into a *Trichoderma* host cell having a disrupted egl5 gene and one or more endogenous genes encoding additional functional proteins;

incubating the host cell in a medium suitable for producing the protein of interest and additional functional proteins; and subjecting the protein of interest and additional functional proteins to an elevated temperature sufficient to substantially inactivate the additional proteins;

wherein the elevated temperature is insufficient to inactivate the thermostable protein of interest and would be insufficient to inactivate EGV cellulase produced by a functional egl5 gene;

wherein the thermostable protein of interest is produced in active or functional form substantially in the absence of activity from the additional proteins.

13. A method for making a thermostable protein of interest in a *Trichoderma* host cell, comprising:

producing the thermostable protein of interest and one or more additional functional proteins in *Trichoderma* host cells comprising a gene encoding the protein of interest, a disrupted egl5 gene, and a gene or genes encoding the one or more additional functional proteins;

subjecting a protein mixture obtained from the host cells to an elevated temperature that is sufficient to substantially inactivate the one or more additional functional proteins but insufficient to inactive the thermostable protein of interest and EGV cellulase produced by a functional egl5 gene;

wherein the thermostable protein of interest is produced in active or functional form substantially in the absence of activity from the additional functional proteins.

14. A method for making a thermostable protein of interest in a *Trichoderma* host cell, comprising: subjecting a protein mixture obtained from the *Trichoderma* host cells comprising a gene encoding the thermostable protein of interest, a disrupted egl5 gene, and one or more genes encoding additional functional proteins to an elevated temperature to inactivate the one or more additional functional proteins; thereby producing the thermostable or protein of interest in active or functional form in the absence of activity from the additional functional proteins.

15. The method of any of paragraphs 12-14, wherein the egl5 gene is disrupted in host cells naturally comprising an egl5 gene.

16. The method of any of paragraphs 12-15, wherein the egl5 gene is deleted in host cells naturally comprising an egl5 gene.

17. The method of any of paragraphs 12-16, wherein the egl5 gene is deleted by homologous recombination.

18. The method of any of paragraphs 12-17, wherein the one or more additional proteins are thermolabile proteins.

19. The method any of paragraphs 12-18, wherein the one or more additional proteins are selected from the group consisting a cellulase, a hemi-cellulase, and a protease.

20. The method of any of paragraphs 12-18, wherein the one or more additional proteins are selected from the group consisting of an exo-cellobiohydrolase, an endoglucanase, and a β-glucosidase.

21. The method of any of paragraphs 12-20, wherein the protein of interest is thermostable by virtue of being reversibly heat-denaturable.

22. The method of any of paragraphs 12-20, wherein the protein of interest is a hydrophobin.

23. The method of any of paragraphs 12-22, wherein the elevated temperature is a temperature of 90° C. or more.

24. The method of any of paragraphs 12-23, wherein exposure to the elevated temperature is for a time of 5 minutes or more.

25. The method of any of paragraphs 12-23, wherein exposure to the elevated temperature is for a time of 60 minutes or more.

26. A thermostable or reversibly heat-denaturable protein produced by the method of any of paragraphs 12-25.

27. A fermentation broth composition obtained from filamentous fungus host cells and comprising a hydrophobin polypeptide, said fermentation broth being substantially free of cellulase and/or mannanase activity.

28. The fermentation broth composition of paragraph 27, wherein the hydrophobin polypeptide is produced in the presence of thermolabile cellulase and/or mannanase polypeptides, and subjected to an elevated temperature to inactivate the cellulase and/or mannanase polypeptides.

29. The fermentation broth composition of paragraph 27, wherein the hydrophobin polypeptide is produced in host cells having disrupted genes encoding cellulase and/or mannanase polypeptides.

30. The fermentation broth composition of paragraph 27, wherein the hydrophobin polypeptide is produced in host cells lacking genes encoding cellulase and/or mannanase polypeptides.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for making a thermostable polypeptide of interest in a *Trichoderma* host cell modified by substantially reducing or preventing production of a thermostable endoglucananse V (EGV) by the *Trichoderma* host cell, and further modified to express a thermostable polypeptide of interest wherein at least one non-thermostable non-mutated endogenous polypeptide and the exogenous thermostable polypeptide of interest is each expressed in vivo by the *Trichoderma* host cell, and said method comprising:

incubating the modified host cell in a medium suitable for the modified host cell to produce the thermostable polypeptide of interest and the non-thermostable non-mutated endogenous polypeptide, whereby each of the endogenous polypeptide and the thermostable polypeptide of interest each is expressed by the modified host cell; and subjecting the thermostable polypeptide of interest and the non-thermostable non-mutated endogenous polypeptide to an elevated temperature, wherein the elevated temperature is sufficient to substantially inactivate the non-thermostable non-mutated endogenous polypeptide, but insufficient to inactivate the thermostable polypeptide of interest and EGV if it were present;

whereby the thermostable polypeptide of interest is produced in active or functional form substantially in the absence of activity from the non-thermostable non-mutated endogenous polypeptide.

2. The method of claim 1 further comprising isolating a protein mixture from the modified *Trichoderma* host cell prior to the step of subjecting the polypeptide of interest and the endogenous polypeptide to the elevated temperature.

3. The method claim 1 wherein the modified host cell expresses an exo-cellobiohydrolase, an endoglucanase, a β-glucosidase, or combinations thereof.

4. The method of claim 1, wherein the thermostable polypeptide of interest is reversibly heat-denaturable.

5. The method of claim 1, wherein the elevated temperature is a temperature of about 90° C. or more.

6. The method of claim 1, wherein exposure to the elevated temperature is for a time of about 5 minutes or more.

7. The method of claim 1, wherein exposure to the elevated temperature is for a time of about 60 minutes or more.

8. The method of claim 1, wherein the modification comprises one or more deletion or disruption in nucleotides involved in expression of EGV.

9. The method of claim 8, wherein the disruption or deletion comprises deletion or disruption of the gene encoding or the coding region for or the promoter or regulatory elements for expression of EGV.

10. The method of claim 9, wherein the deletion or disruption comprises deletion or disruption of egl5.

11. The method of claim 1, wherein the endogenous polypeptide comprises a cellulase, a hemi-cellulase, a protease, or combinations thereof.

12. The method of claim 1, wherein the *Trichoderma* is *T. reesei*.

13. The method of claim 1, wherein the polypeptide of interest is hydrophobia II.

* * * * *